(12) United States Patent
Lei et al.

(10) Patent No.: US 9,868,724 B2
(45) Date of Patent: Jan. 16, 2018

(54) COMPOUNDS

(71) Applicant: GLAXOSMITHKLINE INTELLECTUAL PROPERTY DEVELOPMENT LIMITED, Middlesex (GB)

(72) Inventors: Hui Lei, Shanghai (CN); Xin Ma, Shanghai (CN); Feng Ren, Shanghai (CN); Xichen Lin, Shanghai (CN); Robert W. Marquis, Jr., Collegeville, PA (US)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 15/314,107

(22) PCT Filed: May 26, 2015

(86) PCT No.: PCT/CN2015/079755
§ 371 (c)(1),
(2) Date: Nov. 28, 2016

(87) PCT Pub. No.: WO2015/180614
PCT Pub. Date: Dec. 3, 2015

(65) Prior Publication Data
US 2017/0101399 A1    Apr. 13, 2017

(30) Foreign Application Priority Data

May 28, 2014 (WO) ................ PCT/CN2014/078701

(51) Int. Cl.
*C07D 417/14* (2006.01)
*C07D 405/14* (2006.01)
*C07D 405/06* (2006.01)
*C07D 241/04* (2006.01)

(52) U.S. Cl.
CPC ......... *C07D 405/06* (2013.01); *C07D 241/04* (2013.01); *C07D 405/14* (2013.01); *C07D 417/14* (2013.01)

(58) Field of Classification Search
CPC ... C07D 405/06; C07D 405/14; C07D 417/14
See application file for complete search history.

(56) References Cited

U.S. PATENT DOCUMENTS

| | | | |
|---|---|---|---|
| 8,604,069 B2 | 12/2013 | Maeba et al. | |
| 9,150,508 B2 | 10/2015 | Birault et al. | |
| 9,242,972 B2 | 1/2016 | Birault et al. | |
| 9,428,452 B2 | 8/2016 | Birault et al. | |
| 9,540,318 B2 | 1/2017 | Birault et al. | |
| 2015/0299121 A1 | 10/2015 | Han et al. | |
| 2016/0257664 A1 | 9/2016 | Birault et al. | |
| 2016/0304478 A1 | 10/2016 | Birault et al. | |
| 2017/0081278 A1 | 3/2017 | Birault et al. | |
| 2017/0101399 A1 | 4/2017 | Lei et al. | |
| 2017/0121313 A1 | 5/2017 | Deng et al. | |
| 2017/0197978 A1 | 7/2017 | Deng et al. | |

FOREIGN PATENT DOCUMENTS

| | | | |
|---|---|---|---|
| WO | WO 2007/022257 A2 | 2/2007 | |
| WO | WO 2007/070626 A2 | 6/2007 | |
| WO | WO 2007/078839 A2 | 7/2007 | |
| WO | WO 2007/089336 A2 | 8/2007 | |
| WO | WO 2012/027965 A1 | 3/2012 | |
| WO | WO 2012/028100 A1 | 3/2012 | |
| WO | WO 2012/100732 A1 | 8/2012 | |
| WO | WO 2012/100734 A1 | 8/2012 | |
| WO | WO 2012/145254 A2 | 10/2012 | |
| WO | WO 2012/139775 A1 | 11/2012 | |
| WO | WO 2012/147916 A1 | 11/2012 | |
| WO | WO 2012/158784 A2 | 11/2012 | |
| WO | WO 2013036912 A2 | 3/2013 | |
| WO | WO 2013/045431 A1 | 4/2013 | |
| WO | WO 2013/160418 A1 | 10/2013 | |
| WO | WO 2013/160419 A1 | 10/2013 | |
| WO | WO 2013/171729 A2 | 11/2013 | |
| WO | WO 2014/086894 | * 6/2014 | ........... C07D 403/12 |
| WO | WO 2014/086894 A1 | 6/2014 | |
| WO | WO 2014086894 | 6/2014 | |
| WO | WO 2015/061515 A1 | 4/2015 | |
| WO | WO 2015/061686 A2 | 4/2015 | |
| WO | WO 2015/180612 | 12/2015 | |
| WO | WO 2015/180613 | 12/2015 | |

OTHER PUBLICATIONS

Silverman. The Organic Chemistry of Drug Design and Action, 25-34 (2004).
Leipe et al. Arthritis & Rheumatism vol. 62, No. 10, Oct. 2010, pp. 2876-2885.
Rutz et al. Cytokine & Growth Factor Reviews 30 (2016) 1-17.
Xue et al. Scientific Reports, pp. 1-17 (2016) available on line at www.nature.com/scientificreports/.

* cited by examiner

*Primary Examiner* — Erich A Leeser
(74) *Attorney, Agent, or Firm* — Dara L. Dinner; Edward R. Gimmi; William R. Majarian

(57) ABSTRACT

The present invention relates to novel retinoid-related orphan receptor gamma (RORγ) modulators and their use in the treatment of diseases mediated by RORγ.

21 Claims, No Drawings

COMPOUNDS

This application is a 371 of International Application No. PCT/CN2015/079755, filed 26 May 2015, claims benefit to PCT Application PCT/CN2014/078701 filed 28 May 2014

The present invention relates to novel retinoid-related orphan receptor gamma (RORγ) modulators and their use in the treatment of diseases mediated by RORγ.

BACKGROUND OF THE INVENTION

Retinoid-related orphan receptors (RORs) are transcription factors which belong to the steroid hormone nuclear receptor superfamily (Jetten & Joo (2006) *Adv. Dev. Biol.* 16:313-355). The ROR family consists of three members, ROR alpha (RORα), ROR beta (RORβ) and ROR gamma (RORγ), each encoded by a separate gene (RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ have been identified: RORγ1 and RORγt (also known as RORγ2). RORγ is a term used to describe both RORγ1 and/or RORγt.

While RORγ1 is expressed in a variety of tissues including thymus, muscle, kidney and liver, RORγt is exclusively expressed in the cells of the immune system. RORγt has been identified as a key regulator of Th17 cell differentiation. Th17 cells are a subset of T helper cells which produce IL-17 and other proinflammatory cytokines. Th17 cells have been shown to have key functions in several mouse autoimmune disease models including experimental autoimmune encephalomyelitis (EAE) and collagen-induced arthritis (CIA). In addition, Th17 cells or their products have been shown to be associated with the pathology of a variety of human inflammatory and autoimmune disorders including multiple sclerosis, rheumatoid arthritis, psoriasis, ankylosing spondylitis, Crohn's disease and asthma (Jetten (2009) *Nucl. Recept. Signal.* 7: e003; Manel et al. (2008) *Nat. Immunol.* 9:641-649; Miossec & Kolls (2012) *Nat. Rev. Drug. Discov.* 10:763-776). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman (2008) *J. Exp. Med.* 205:1517-1522; Leung et al. (2010) *Cell. Mol. Immunol.* 7:182-189). There is evidence that Th17 cells are activated during the disease process and are responsible for recruiting other inflammatory cells types, especially neutrophils, to mediate pathology in the target tissues (Korn et al. (2009) *Annu. Rev. Immunol.* 27:485-517).

RORγt plays a critical role in the pathogenic responses of Th17 cells (Ivanov et al. (2006) *Cell* 126:1121-1133). RORγt deficient mice show very little Th17 cells. In addition, RORγt deficiency resulted in amelioration of EAE. Further support for the role of RORγt in the pathogenesis of autoimmune or inflammatory diseases can be found in the following references: Jetten & Joo (2006) *Adv. Dev. Biol.* 16:313-355; Meier et al. (2007) *Immunity* 26:643-654; Aloisi & Pujol-Borrell (2006) *Nat. Rev. Immunol.* 6:205-217; Jager et al. (2009) *J. Immunol.* 183:7169-7177; Serafini et al. (2004) *Brain Pathol.* 14:164-174; Magliozzi et al. (2007) *Brain* 130:1089-1104; Barnes (2008) *Nat. Rev. Immunol.* 8:183-192; Miossec & Kolls (2012) *Nat. Rev. Drug. Discov.* 10:763-776.

In light of the role RORγ plays in the pathogenesis of diseases, it is desirable to prepare compounds that modulate RORγ activity, which can be used in the treatment of diseases mediated by RORγ.

SUMMARY OF THE INVENTION

The invention is directed to novel RORγ modulators and their use in the treatment of diseases mediated by RORγ. Specifically, the invention is directed to compounds according to Formula I.

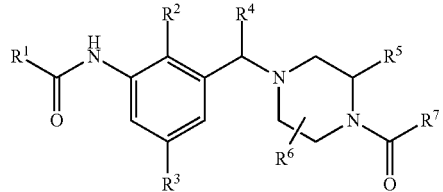

Formula I wherein $R^1$ to $R^7$ are defined below, and to pharmaceutically-acceptable salts thereof.

In another aspect, this invention provides for the use of the compounds of Formula I for the treatment of diseases mediated by RORγ. Examples of such diseases include autoimmune or inflammatory diseases such as multiple sclerosis, rheumatoid arthritis, psoriasis and ankylosing spondylitis. In yet another aspect, the invention is directed to methods of treating such diseases.

DETAILED DESCRIPTION OF THE INVENTION

Terms and Definitions

"Alkyl" refers to a monovalent saturated hydrocarbon chain having the specified number of member atoms. For example, $C_1$-$C_6$ alkyl refers to an alkyl group having from 1 to 6 member atoms. Alkyl groups may be optionally substituted with one or more substituent as defined herein. Alkyl groups may be straight or branched. Representative branched alkyl groups have one, two, or three branches. Examples of alkyl include methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a saturated hydrocarbon ring having the specified number of member atoms. Cycloalkyl groups are monocyclic ring systems or are fused or bridged bicyclic ring systems. For example, C3-C7 cycloalkyl refers to a cycloalkyl group having from 3 to 7 member atoms. Cycloalkyl groups may be optionally substituted with one or more substituent as defined herein. Examples of cycloalkyl include cyclopropyl, cyclobutyl, cyclopentyl, and cyclohexyl.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct species in vitro or in vivo.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems or are fused or bridged bicyclic ring systems. Monocyclic heteroaryl rings have from 5 to 7 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Examples of heteroaryl include pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, furopyridinyl, and naphthyridinyl. As used herein, "5 to 6 membered monocyclic heteroaryl" represents a group or moiety comprising an aromatic monovalent monocyclic radical, containing 5 or 6 ring atoms, including at least one carbon atom and 1 to 4 heteroatoms independently selected from nitrogen, oxygen, and sulfur. Selected 5-membered monocyclic heteroaryl groups contain one nitrogen, oxygen, or sulfur ring heteroatom, and optionally contain 1, 2, or 3 additional nitrogen ring atoms. Selected 6-membered monocyclic heteroaryl groups contain 1, 2, or 3 nitrogen ring heteroatoms. Illustrative examples of 5 to 6 membered monocyclic heteroaryl groups useful in the present invention include, but are not limited to pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, and tetrazolyl.

"Heteroatom" refers to a nitrogen, sulphur, or oxygen atom.

"Heterocycloalkyl" refers to a saturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups are monocyclic ring systems or are fused, spiro, or bridged bicyclic ring systems. Monocyclic heterocycloalkyl rings have from 4 to 7 member atoms. Bicyclic heterocycloalkyl rings have from 7 to 11 member atoms. Examples of heterocycloalkyl include pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,3-oxathiolanyl, 1,3-dithianyl, azetidinyl, oxetanyl, azabicylo[3.2.1]octyl, and oxabicylo[2.2.1]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituent as defined.

"RORγ" refers to all isoforms encoded by the RORC gene which include RORγ1 and RORγt.

"RORγ modulator" refers to a chemical compound that inhibits, either directly or indirectly, the activity of RORγ. RORγ modulators include antagonists and inverse agonists of RORγ.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom.

Compounds

The present invention provides a compound of Formula I or a pharmaceutically acceptable salt thereof.

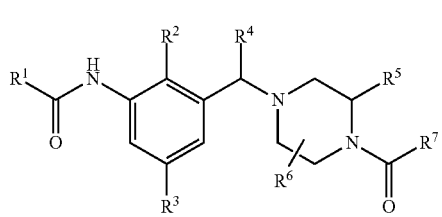

Formula I wherein:
R$^1$ is:
  5 to 6 membered monocyclic heteroaryl optionally substituted with i) C$_1$-C$_5$ alkyl optionally substituted with CF$_3$ or CN, ii) CH$_2$F; or iii) one to two substituents independently selected from the group consisting of halo, methyl, methoxy and CN; wherein said 5 to 6 membered monocyclic heteroaryl is selected from the group consisting of pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, and tetrazolyl, or N-oxides thereof; or
phenyl substituted with one to two substituents independently selected from the group consisting of: CN, halo and methyl;
$R^2$ is $C_1$-$C_3$ alkyl;
$R^3$ is halo;
$R^4$ is H;
$R^5$ is $C_1$-$C_3$ alkyl;
$R^6$ is H or methyl; and
$R^7$ is tetrahydrofuranyl or tetrahydropyranyl, wherein said tetrahydrofuranyl or tetrahydropyranyl is optionally substituted with methyl.

In one embodiment, the invention relates to the compounds of Formula I, wherein:
$R^1$ is:
5 to 6 membered monocyclic heteroaryl optionally substituted with i) $C_1$-$C_5$ alkyl optionally substituted with $CF_3$ or CN, ii) $CH_2F$; or iii) one to two substituents independently selected from the group consisting of halo, methyl, methoxy and CN; or
phenyl substituted with one to two substituents independently selected from the group consisting of: CN, halo and methyl;
$R^2$ is $C_1$-$C_3$ alkyl;
$R^3$ is halo;
$R^4$ is H;
$R^5$ is $C_1$-$C_3$ alkyl;
$R^6$ is H or methyl; and
$R^7$ is tetrahydrofuranyl or tetrahydropyranyl, wherein said tetrahydrofuranyl or tetrahydropyranyl is optionally substituted with methyl.

In one embodiment, the invention relates to the compounds of Formula I, wherein $R^1$ is:
thiazolyl or pyridinyl optionally substituted with i) $C_1$-$C_5$ alkyl optionally substituted with $CF_3$ or CN, ii) $CH_2F$; or iii) one to two substituents independently selected from the group consisting of halo, methyl, methoxy and CN; or
phenyl substituted with one to two substituents independently selected from the group consisting of: CN, halo and methyl.

In one embodiment, the invention relates to the compounds of Formula I, wherein $R^1$ is phenyl substituted with one or two substituents selected from CN and halo. In one embodiment, this invention also relates to compounds of any of the above embodiments, wherein $R^1$ is phenyl substituted with CN. In one embodiment, this invention also relates to compounds of any of the above embodiments, wherein $R^1$ is phenyl substituted with CN and F.

In one embodiment, this invention also relates to compounds of any of the above embodiments, wherein $R^1$ is 6 membered monocyclic heteroaryl substituted with two substituents independently selected from the group consisting of methyl, halo, CN and methoxy. In one embodiment, this invention also relates to compounds of any of the above embodiments, wherein $R^1$ is pyridinyl substituted with two substituents independently selected from the group consisting of methyl, halo, CN and methoxy. In one embodiment, this invention also relates to compounds of any of the above embodiments, wherein $R^1$ is pyridinyl substituted with two substituents independently selected from the group consisting of methyl, F, and CN. In one embodiment, this invention also relates to compounds of any of the above embodiments, wherein $R^1$ is pyridinyl substituted with methyl and F. In one embodiment, this invention also relates to compounds of any of the above embodiments, wherein $R^1$ is pyridinyl substituted with methyl and Cl. In one embodiment, this invention also relates to compounds of any of the above embodiments, wherein $R^1$ is pyridinyl substituted with methyl and CN. In one embodiment, this invention also relates to compounds of any of the above embodiments, wherein $R^1$ is pyridinyl substituted with CN and F.

In one embodiment, this invention also relates to compounds of any of the above embodiments, wherein $R^2$ is methyl.

In one embodiment, this invention also relates to compounds of any of the above embodiments, wherein $R^3$ is Cl.

In one embodiment, this invention also relates to compounds of any of the above embodiments, wherein $R^5$ is methyl. In one embodiment, this invention also relates to compounds of any of the above embodiments, wherein $R^5$ is ethyl.

In one embodiment, this invention also relates to compounds of any of the above embodiments, wherein $R^6$ is H.

In one embodiment, this invention also relates to compounds of any of the above embodiments, wherein $R^7$ is tetrahydrofuranyl optionally substituted with methyl. In one embodiment, this invention also relates to compounds of any of the above embodiments, wherein $R^7$ is tetrahydrofuranyl. In one embodiment, this invention also relates to compounds of any of the above embodiments, wherein $R^7$ is tetrahydropyranyl. In one embodiment, this invention also relates to compounds of any of the above embodiments, wherein $R^7$ is methyltetrahydrofuranyl.

In one embodiment, the invention relates to compounds of Formula (I), wherein $R^1$ is pyridinyl substituted with i) methyl and CN or ii) methyl and Cl, $R^2$ is methyl, $R^3$ is Cl, $R^4$ is H, $R^5$ is methyl, $R^6$ is H and $R^7$ is tetrahydrofuranyl.

In one embodiment, the invention relates to compounds of Formula (I), wherein $R^1$ is pyridinyl substituted with methyl and F, $R^2$ is methyl, $R^3$ is Cl, $R^4$ is H, $R^5$ is methyl, $R^6$ is H and $R^7$ is tetrahydrofuranyl.

In another embodiment, the invention relates to compounds of Formula (I), wherein $R^1$ is phenyl substituted with CN, $R^2$ is methyl, $R^3$ is Cl, $R^4$ is H, $R^5$ is methyl, $R^6$ is H, and $R^7$ is tetrahydrofuranyl or tetrahydropyranyl.

In another embodiment, the invention relates to compounds of Formula (I), wherein $R^1$ is phenyl substituted with CN and F, $R^2$ is methyl, $R^3$ is Cl, $R^4$ is H, $R^5$ is methyl, $R^6$ is H, and $R^7$ is tetrahydrofuranyl.

In one embodiment, the compound of Formula I is selected from:
(S)—N-(5-chloro-2-methyl-3-((3-methyl-4-(tetrahydro-2H-pyran-4-carbonyl)piperazin-1-yl)methyl)phenyl)-3-cyanobenzamide;
3-cyano-N-(5-fluoro-2-methyl-3-(((S)-3-methyl-4-((R)-tetrahydrofuran-2-carbonyl)piperazin-1-yl)methyl)phenyl)benzamide;
3-cyano-N-(5-fluoro-2-methyl-3-(((S)-3-methyl-4-((S)-tetrahydrofuran-2-carbonyl)piperazin-1-yl)methyl)phenyl)benzamide;
(S)-3-cyano-N-(5-fluoro-2-methyl-3-((3-methyl-4-(tetrahydro-2H-pyran-4-carbonyl)piperazin-1-yl)methyl)phenyl)benzamide;
3-cyano-N-(5-fluoro-2-methyl-3-(((3S)-3-methyl-4-(tetrahydrofuran-2-carbonyl)piperazin-1-yl)methyl)phenyl)benzamide;
3-cyano-N-(5-fluoro-2-methyl-3-(((3S)-3-methyl-4-(tetrahydrofuran-3-carbonyl)piperazin-1-yl)methyl)phenyl)benzamide;
N-(5-chloro-2-methyl-3-(((3S)-3-methyl-4-(tetrahydrofuran-2-carbonyl)piperazin-1-yl)methyl)phenyl)-3-cyanobenzamide;

N-(5-chloro-2-methyl-3-(((3S)-3-methyl-4-(tetrahydrofuran-3-carbonyl)piperazin-1-yl)methyl)phenyl)-3-cyanobenzamide;

(S)—N-(5-chloro-2-methyl-3-((3-methyl-4-(tetrahydro-2H-pyran-4-carbonyl)piperazin-1-yl)methyl)phenyl)-6-ethylnicotinamide;

N-(5-chloro-2-methyl-3-(((S)-3-methyl-4-((S)-tetrahydrofuran-2-carbonyl)piperazin-1-yl)methyl)phenyl)-6-ethylnicotinamide;

N-(5-chloro-2-methyl-3-(((S)-3-methyl-4-((S)-tetrahydrofuran-2-carbonyl)piperazin-1-yl)methyl)phenyl)-3-cyano-4-methylbenzamide;

N-(5-chloro-2-methyl-3-(((S)-3-methyl-4-((R)-tetrahydrofuran-2-carbonyl)piperazin-1-yl)methyl)phenyl)-3-cyano-4-methylbenzamide;

(S)—N-(5-chloro-2-methyl-3-((3-methyl-4-(tetrahydro-2H-pyran-4-carbonyl)piperazin-1-yl)methyl)phenyl)-6-methylnicotinamide;

N-(5-chloro-2-methyl-3-(((S)-3-methyl-4-((R)-tetrahydrofuran-2-carbonyl)piperazin-1-yl)methyl)phenyl)-6-ethylnicotinamide;

N-(5-chloro-2-methyl-3-(((S)-3-methyl-4-((R)-tetrahydrofuran-2-carbonyl)piperazin-1-yl)methyl)phenyl)-2-cyanoisonicotinamide;

N-(5-chloro-2-methyl-3-(((S)-3-methyl-4-((S)-tetrahydrofuran-2-carbonyl)piperazin-1-yl)methyl)phenyl)-2-cyanoisonicotinamide;

(S)—N-(5-chloro-2-methyl-3-((3-methyl-4-(tetrahydro-2H-pyran-4-carbonyl)piperazin-1-yl)methyl)phenyl)-6-cyano-5-methylnicotinamide;

N-(5-chloro-2-methyl-3-(((S)-3-methyl-4-((R)-tetrahydrofuran-2-carbonyl)piperazin-1-yl)methyl)phenyl)-6-cyano-5-methylnicotinamide;

N-(5-chloro-2-methyl-3-(((S)-3-methyl-4-((S)-tetrahydrofuran-2-carbonyl)piperazin-1-yl)methyl)phenyl)-6-cyano-5-methylnicotinamide;

N-(5-chloro-2-methyl-3-(((S)-3-methyl-4-((R)-tetrahydrofuran-2-carbonyl)piperazin-1-yl)methyl)phenyl)-6-cyano-5-fluoronicotinamide;

N-(5-chloro-2-methyl-3-(((S)-3-methyl-4-((S)-tetrahydrofuran-2-carbonyl)piperazin-1-yl)methyl)phenyl)-6-cyano-5-fluoronicotinamide;

N-(5-chloro-2-methyl-3-(((S)-3-methyl-4-((R)-tetrahydrofuran-2-carbonyl)piperazin-1-yl)methyl)phenyl)-3-cyano-5-fluorobenzamide;

N-(5-chloro-2-methyl-3-(((S)-3-methyl-4-((S)-tetrahydrofuran-2-carbonyl)piperazin-1-yl)methyl)phenyl)-3-cyano-5-fluorobenzamide;

N-(5-chloro-2-methyl-3-(((S)-3-methyl-4-((R)-tetrahydrofuran-2-carbonyl)piperazin-1-yl)methyl)phenyl)-3-cyanobenzamide;

N-(5-chloro-2-methyl-3-(((S)-3-methyl-4-((R)-tetrahydrofuran-3-carbonyl)piperazin-1-yl)methyl)phenyl)-3-cyanobenzamide;

N-(5-chloro-2-methyl-3-(((S)-3-methyl-4-((S)-tetrahydrofuran-2-carbonyl)piperazin-1-yl)methyl)phenyl)-3-cyanobenzamide;

N-(5-chloro-2-methyl-3-(((S)-3-methyl-4-((S)-tetrahydrofuran-3-carbonyl)piperazin-1-yl)methyl)phenyl)-3-cyanobenzamide;

N-(5-chloro-2-methyl-3-(((S)-3-methyl-4-((R)-tetrahydrofuran-2-carbonyl)piperazin-1-yl)methyl)phenyl)-3-cyano-4-fluorobenzamide;

N-(5-chloro-2-methyl-3-(((S)-3-methyl-4-((S)-tetrahydrofuran-2-carbonyl)piperazin-1-yl)methyl)phenyl)-3-cyano-4-fluorobenzamide;

N-(5-chloro-2-methyl-3-(((S)-3-methyl-4-((R)-tetrahydrofuran-2-carbonyl)piperazin-1-yl)methyl)phenyl)-5-fluoro-6-methylnicotinamide;

N-(5-chloro-2-methyl-3-(((S)-3-methyl-4-((S)-tetrahydrofuran-2-carbonyl)piperazin-1-yl)methyl)phenyl)-5-fluoro-6-methylnicotinamide;

N-(5-chloro-2-methyl-3-(((S)-3-methyl-4-((R)-tetrahydrofuran-2-carbonyl)piperazin-1-yl)methyl)phenyl)-5-cyano-6-methylnicotinamide;

N-(5-chloro-2-methyl-3-(((S)-3-methyl-4-((S)-tetrahydrofuran-2-carbonyl)piperazin-1-yl)methyl)phenyl)-5-cyano-6-methylnicotinamide;

N-(5-chloro-2-methyl-3-(((S)-3-methyl-4-((R)-2-methyltetrahydrofuran-2-carbonyl)piperazin-1-yl)methyl)phenyl)-3-cyanobenzamide;

N-(5-chloro-2-methyl-3-(((S)-3-methyl-4-((S)-2-methyltetrahydrofuran-2-carbonyl)piperazin-1-yl)methyl)phenyl)-3-cyanobenzamide;

N-(5-chloro-2-methyl-3-(((S)-3-methyl-4-((R)-tetrahydrofuran-3-carbonyl)piperazin-1-yl)methyl)phenyl)-6-methylnicotinamide;

N-(5-chloro-2-methyl-3-(((S)-3-methyl-4-((S)-tetrahydrofuran-3-carbonyl)piperazin-1-yl)methyl)phenyl)-6-methylnicotinamide;

N-(5-chloro-2-methyl-3-(((S)-3-methyl-4-((R)-2-methyltetrahydrofuran-2-carbonyl)piperazin-1-yl)methyl)phenyl)-6-methylnicotinamide;

N-(5-chloro-2-methyl-3-(((S)-3-methyl-4-((S)-2-methyltetrahydrofuran-2-carbonyl)piperazin-1-yl)methyl)phenyl)-6-methylnicotinamide;

N-(5-chloro-2-methyl-3-(((S)-3-methyl-4-((S)-tetrahydro-2H-pyran-3-carbonyl)piperazin-1-yl)methyl)phenyl)-3-cyanobenzamide;

N-(5-chloro-2-methyl-3-(((S)-3-methyl-4-((R)-tetrahydro-2H-pyran-3-carbonyl)piperazin-1-yl)methyl)phenyl)-3-cyanobenzamide;

N-(5-chloro-2-methyl-3-(((S)-3-methyl-4-((R)-tetrahydro-2H-pyran-2-carbonyl)piperazin-1-yl)methyl)phenyl)-3-cyanobenzamide;

N-(5-chloro-2-methyl-3-(((S)-3-methyl-4-((S)-tetrahydro-2H-pyran-2-carbonyl)piperazin-1-yl)methyl)phenyl)-3-cyanobenzamide;

N-(5-chloro-2-methyl-3-(((S)-3-methyl-4-((R)-tetrahydro-2H-pyran-3-carbonyl)piperazin-1-yl)methyl)phenyl)-5-fluoronicotinamide;

N-(5-chloro-2-methyl-3-(((S)-3-methyl-4-((S)-tetrahydro-2H-pyran-3-carbonyl)piperazin-1-yl)methyl)phenyl)-5-fluoronicotinamide;

N-(5-chloro-2-methyl-3-(((S)-3-methyl-4-((S)-tetrahydro-2H-pyran-2-carbonyl)piperazin-1-yl)methyl)phenyl)-5-fluoronicotinamide;

N-(5-chloro-2-methyl-3-(((S)-3-methyl-4-((R)-tetrahydro-2H-pyran-2-carbonyl)piperazin-1-yl)methyl)phenyl)-5-fluoronicotinamide;

N-(5-chloro-2-methyl-3-(((S)-3-methyl-4-((R)-tetrahydro-2H-pyran-3-carbonyl)piperazin-1-yl)methyl)phenyl)-2-methylthiazole-5-carboxamide;

N-(5-chloro-2-methyl-3-(((S)-3-methyl-4-((S)-tetrahydro-2H-pyran-3-carbonyl)piperazin-1-yl)methyl)phenyl)-2-methylthiazole-5-carboxamide;

N-(5-chloro-2-methyl-3-(((S)-3-methyl-4-((S)-tetrahydro-2H-pyran-2-carbonyl)piperazin-1-yl)methyl)phenyl)-2-methylthiazole-5-carboxamide;

N-(5-chloro-2-methyl-3-(((S)-3-methyl-4-((R)-tetrahydro-2H-pyran-2-carbonyl)piperazin-1-yl)methyl)phenyl)-2-methylthiazole-5-carboxamide;

N-(5-chloro-2-methyl-3-(((S)-3-methyl-4-((S)-tetrahydro-2H-pyran-3-carbonyl)piperazin-1-yl)methyl)phenyl)-6-methylnicotinamide;
N-(5-chloro-2-methyl-3-(((S)-3-methyl-4-((R)-tetrahydro-2H-pyran-3-carbonyl)piperazin-1-yl)methyl)phenyl)-6-methylnicotinamide;
N-(5-chloro-2-methyl-3-(((S)-3-methyl-4-((R)-tetrahydro-2H-pyran-2-carbonyl)piperazin-1-yl)methyl)phenyl)-6-methylnicotinamide;
N-(5-chloro-2-methyl-3-(((S)-3-methyl-4-((S)-tetrahydro-2H-pyran-2-carbonyl)piperazin-1-yl)methyl)phenyl)-6-methylnicotinamide;
N-(5-chloro-2-methyl-3-(((S)-3-methyl-4-((R)-tetrahydrofuran-3-carbonyl)piperazin-1-yl)methyl)phenyl)-5-fluoro-6-methylnicotinamide;
N-(5-chloro-2-methyl-3-(((S)-3-methyl-4-((S)-tetrahydrofuran-3-carbonyl)piperazin-1-yl)methyl)phenyl)-5-fluoro-6-methylnicotinamide;
N-(5-chloro-2-methyl-3-(((S)-3-methyl-4-((R)-tetrahydrofuran-2-carbonyl)piperazin-1-yl)methyl)phenyl)-3-fluorobenzamide;
N-(5-chloro-2-methyl-3-(((S)-3-methyl-4-((S)-tetrahydrofuran-2-carbonyl)piperazin-1-yl)methyl)phenyl)-3-fluorobenzamide;
3-chloro-N-(5-chloro-2-methyl-3-(((S)-3-methyl-4-((S)-tetrahydrofuran-2-carbonyl)piperazin-1-yl)methyl)phenyl)benzamide;
N-(5-chloro-2-methyl-3-(((S)-3-methyl-4-((R)-tetrahydrofuran-2-carbonyl)piperazin-1-yl)methyl)phenyl)-3-fluoro-4-methylbenzamide;
N-(5-chloro-2-methyl-3-(((S)-3-methyl-4-((S)-tetrahydrofuran-2-carbonyl)piperazin-1-yl)methyl)phenyl)-3-fluoro-4-methylbenzamide;
N-(5-chloro-2-methyl-3-(((S)-3-methyl-4-((S)-tetrahydrofuran-2-carbonyl)piperazin-1-yl)methyl)phenyl)-3,5-difluorobenzamide;
N-(5-chloro-2-methyl-3-(((S)-3-methyl-4-((R)-tetrahydrofuran-2-carbonyl)piperazin-1-yl)methyl)phenyl)-3,5-difluorobenzamide;
3-chloro-N-(5-chloro-2-methyl-3-(((S)-3-methyl-4-((R)-tetrahydrofuran-2-carbonyl)piperazin-1-yl)methyl)phenyl)benzamide;
N-(5-chloro-2-methyl-3-(((S)-3-methyl-4-((R)-tetrahydrofuran-2-carbonyl)piperazin-1-yl)methyl)phenyl)-3-fluoro-5-methylbenzamide;
N-(5-chloro-2-methyl-3-(((S)-3-methyl-4-((S)-tetrahydrofuran-2-carbonyl)piperazin-1-yl)methyl)phenyl)-3-fluoro-5-methylbenzamide;
N-(5-chloro-2-methyl-3-(((S)-3-methyl-4-((R)-tetrahydrofuran-2-carbonyl)piperazin-1-yl)methyl)phenyl)-5,6-dimethylnicotinamide;
N-(5-fluoro-2-methyl-3-(((S)-3-methyl-4-((R)-tetrahydrofuran-2-carbonyl)piperazin-1-yl)methyl)phenyl)-5,6-dimethylnicotinamide;
N-(5-chloro-3-(((S)-3-ethyl-4-((R)-tetrahydrofuran-2-carbonyl)piperazin-1-yl)methyl)-2-methylphenyl)-5-fluoro-6-methylnicotinamide;
5-chloro-N-(5-chloro-2-methyl-3-(((S)-3-methyl-4-((R)-tetrahydrofuran-2-carbonyl)piperazin-1-yl)methyl)phenyl)nicotinamide;
5-fluoro-N-(5-fluoro-2-methyl-3-(((S)-3-methyl-4-((R)-tetrahydrofuran-2-carbonyl)piperazin-1-yl)methyl)phenyl)-6-methylnicotinamide;
N-(5-chloro-2-methyl-3-(((S)-3-methyl-4-((R)-tetrahydrofuran-3-carbonyl)piperazin-1-yl)methyl)phenyl)-5,6-dimethylnicotinamide;
N-(5-chloro-2-methyl-3-(((S)-3-methyl-4-((S)-tetrahydrofuran-3-carbonyl)piperazin-1-yl)methyl)phenyl)-5,6-dimethylnicotinamide;
5-chloro-N-(5-fluoro-2-methyl-3-(((S)-3-methyl-4-((S)-tetrahydrofuran-3-carbonyl)piperazin-1-yl)methyl)phenyl)-6-methylnicotinamide;
5-chloro-N-(5-fluoro-2-methyl-3-(((S)-3-methyl-4-((R)-tetrahydrofuran-3-carbonyl)piperazin-1-yl)methyl)phenyl)-6-methylnicotinamide;
(S)—N-(5-chloro-2-methyl-3-((3-methyl-4-(tetrahydro-2H-pyran-4-carbonyl)piperazin-1-yl)methyl)phenyl)-6-cyanonicotinamide;
(S)—N-(5-chloro-2-methyl-3-((3-methyl-4-(tetrahydro-2H-pyran-4-carbonyl)piperazin-1-yl)methyl)phenyl)-2-cyanoisonicotinamide;
(S)—N-(5-chloro-2-methyl-3-((3-methyl-4-(tetrahydro-2H-pyran-4-carbonyl)piperazin-1-yl)methyl)phenyl)-5-cyano-6-methylnicotinamide;
(S)—N-(5-chloro-2-methyl-3-((3-methyl-4-(tetrahydro-2H-pyran-4-carbonyl)piperazin-1-yl)methyl)phenyl)-3-cyano-4-methylbenzamide;
N-(5-chloro-2-methyl-3-(((S)-3-methyl-4-((R)-tetrahydrofuran-2-carbonyl)piperazin-1-yl)methyl)phenyl)-6-(fluoromethyl)nicotinamide;
N-(5-chloro-2-methyl-3-(((S)-3-methyl-4-((S)-tetrahydrofuran-2-carbonyl)piperazin-1-yl)methyl)phenyl)-6-(fluoromethyl)nicotinamide;
(S)—N-(5-chloro-2-methyl-3-((3-methyl-4-(tetrahydro-2H-pyran-4-carbonyl)piperazin-1-yl)methyl)phenyl)-6-methoxynicotinamide;
(S)—N-(5-chloro-2-methyl-3-((3-methyl-4-(tetrahydro-2H-pyran-4-carbonyl)piperazin-1-yl)methyl)phenyl)-5-fluoro-6-methylnicotinamide;
5-chloro-N-(5-fluoro-2-methyl-3-(((S)-3-methyl-4-((R)-tetrahydrofuran-2-carbonyl)piperazin-1-yl)methyl)phenyl)-6-methylnicotinamide;
5-chloro-N-(5-fluoro-2-methyl-3-(((S)-3-methyl-4-((S)-tetrahydrofuran-2-carbonyl)piperazin-1-yl)methyl)phenyl)-6-methylnicotinamide;
N-(5-chloro-3-(((S)-3-ethyl-4-((R)-tetrahydrofuran-2-carbonyl)piperazin-1-yl)methyl)-2-methylphenyl)-6-methylnicotinamide;
5-chloro-N-(5-chloro-2-methyl-3-(((S)-3-methyl-4-((S)-tetrahydrofuran-2-carbonyl)piperazin-1-yl)methyl)phenyl)-6-methylnicotinamide;
5-chloro-N-(5-chloro-2-methyl-3-(((S)-3-methyl-4-((R)-tetrahydrofuran-2-carbonyl)piperazin-1-yl)methyl)phenyl)-6-methylnicotinamide;
N-(5-chloro-2-methyl-3-(((S)-3-methyl-4-((S)-tetrahydrofuran-2-carbonyl)piperazin-1-yl)methyl)phenyl)-5,6-dimethylnicotinamide;
N-(5-chloro-2-methyl-3-(((S)-3-methyl-4-((R)-tetrahydrofuran-3-carbonyl)piperazin-1-yl)methyl)phenyl)-5-cyano-6-methylnicotinamide;
N-(5-chloro-2-methyl-3-(((S)-3-methyl-4-((S)-tetrahydrofuran-3-carbonyl)piperazin-1-yl)methyl)phenyl)-5-cyano-6-methylnicotinamide;
N-(5-chloro-2-methyl-3-(((S)-3-methyl-4-((R)-tetrahydrofuran-3-carbonyl)piperazin-1-yl)methyl)phenyl)-5-methoxy-6-methylnicotinamide;
N-(5-chloro-2-methyl-3-(((S)-3-methyl-4-((S)-tetrahydrofuran-3-carbonyl)piperazin-1-yl)methyl)phenyl)-5-methoxy-6-methylnicotinamide;
N-(5-chloro-2-methyl-3-(((R)-3-methyl-4-((R)-tetrahydrofuran-2-carbonyl)piperazin-1-yl)methyl)phenyl)-5-fluoro-6-methylnicotinamide;

N-(5-chloro-2-methyl-3-(((R)-3-methyl-4-((S)-tetrahydro-furan-2-carbonyl)piperazin-1-yl)methyl)phenyl)-5-fluoro-6-methylnicotinamide;

N-(5-chloro-2-methyl-3-(((R)-3-methyl-4-((S)-tetrahydro-furan-3-carbonyl)piperazin-1-yl)methyl)phenyl)-5-fluoro-6-methylnicotinamide;

N-(5-chloro-2-methyl-3-(((R)-3-methyl-4-((R)-tetrahydro-furan-3-carbonyl)piperazin-1-yl)methyl)phenyl)-5-fluoro-6-methylnicotinamide; and 5-((5-chloro-2-methyl-3-(((S)-3-methyl-4-((R)-tetrahydro-furan-3-carbonyl)piperazin-1-yl)methyl)phenyl)carbamoyl)-3-fluoro-2-methylpyridine 1-oxide;

or a pharmaceutically acceptable salt thereof.

In another embodiment, the compound of Formula I is selected from:

(S)—N-(5-chloro-2-methyl-3-((3-methyl-4-(tetrahydro-2H-pyran-4-carbonyl)piperazin-1-yl)methyl)phenyl)-3-cyanobenzamide;

N-(5-chloro-2-methyl-3-(((S)-3-methyl-4-((R)-tetrahydro-furan-2-carbonyl)piperazin-1-yl)methyl)phenyl)-3-cyano-5-fluorobenzamide;

N-(5-chloro-2-methyl-3-(((S)-3-methyl-4-((S)-tetrahydro-furan-2-carbonyl)piperazin-1-yl)methyl)phenyl)-3-cyano-5-fluorobenzamide;

N-(5-chloro-2-methyl-3-(((S)-3-methyl-4-((R)-tetrahydro-furan-2-carbonyl)piperazin-1-yl)methyl)phenyl)-3-cyanobenzamide;

N-(5-chloro-2-methyl-3-(((S)-3-methyl-4-((R)-tetrahydro-furan-3-carbonyl)piperazin-1-yl)methyl)phenyl)-3-cyanobenzamide;

N-(5-chloro-2-methyl-3-(((S)-3-methyl-4-((S)-tetrahydro-furan-2-carbonyl)piperazin-1-yl)methyl)phenyl)-3-cyanobenzamide;

N-(5-chloro-2-methyl-3-(((S)-3-methyl-4-((S)-tetrahydro-furan-3-carbonyl)piperazin-1-yl)methyl)phenyl)-3-cyanobenzamide;

N-(5-chloro-2-methyl-3-(((S)-3-methyl-4-((R)-tetrahydro-furan-2-carbonyl)piperazin-1-yl)methyl)phenyl)-3-cyano-4-fluorobenzamide;

N-(5-chloro-2-methyl-3-(((S)-3-methyl-4-((S)-tetrahydro-furan-2-carbonyl)piperazin-1-yl)methyl)phenyl)-3-cyano-4-fluorobenzamide;

N-(5-chloro-2-methyl-3-(((S)-3-methyl-4-((R)-tetrahydro-furan-2-carbonyl)piperazin-1-yl)methyl)phenyl)-5-fluoro-6-methylnicotinamide;

N-(5-chloro-2-methyl-3-(((S)-3-methyl-4-((S)-tetrahydro-furan-2-carbonyl)piperazin-1-yl)methyl)phenyl)-5-fluoro-6-methylnicotinamide;

N-(5-chloro-2-methyl-3-(((S)-3-methyl-4-((R)-tetrahydro-furan-2-carbonyl)piperazin-1-yl)methyl)phenyl)-5-cyano-6-methylnicotinamide;

N-(5-chloro-2-methyl-3-(((S)-3-methyl-4-((S)-tetrahydro-furan-2-carbonyl)piperazin-1-yl)methyl)phenyl)-5-cyano-6-methylnicotinamide;

N-(5-chloro-2-methyl-3-(((S)-3-methyl-4-((R)-tetrahydro-furan-3-carbonyl)piperazin-1-yl)methyl)phenyl)-5-fluoro-6-methylnicotinamide;

N-(5-chloro-2-methyl-3-(((S)-3-methyl-4-((S)-tetrahydro-furan-3-carbonyl)piperazin-1-yl)methyl)phenyl)-5-fluoro-6-methylnicotinamide;

5-chloro-N-(5-chloro-2-methyl-3-(((S)-3-methyl-4-((S)-tetrahydrofuran-2-carbonyl)piperazin-1-yl)methyl)phenyl)-6-methylnicotinamide; and 5-chloro-N-(5-chloro-2-methyl-3-(((S)-3-methyl-4-((R)-tetrahydrofuran-2-carbonyl)piperazin-1-yl)methyl)phenyl)-6-methylnicotinamide;

or a pharmaceutically acceptable salt thereof.

In another embodiment, the compound of Formula I is selected from:

N-(5-chloro-2-methyl-3-(((S)-3-methyl-4-((S)-tetrahydro-furan-2-carbonyl)piperazin-1-yl)methyl)phenyl)-5,6-dimethylnicotinamide;

N-(5-chloro-2-methyl-3-(((S)-3-methyl-4-((R)-tetrahydro-furan-3-carbonyl)piperazin-1-yl)methyl)phenyl)-5-cyano-6-methylnicotinamide;

N-(5-chloro-2-methyl-3-(((S)-3-methyl-4-((S)-tetrahydro-furan-3-carbonyl)piperazin-1-yl)methyl)phenyl)-5-cyano-6-methylnicotinamide;

N-(5-chloro-2-methyl-3-(((S)-3-methyl-4-((R)-tetrahydro-furan-3-carbonyl)piperazin-1-yl)methyl)phenyl)-5-methoxy-6-methylnicotinamide;

N-(5-chloro-2-methyl-3-(((S)-3-methyl-4-((S)-tetrahydro-furan-3-carbonyl)piperazin-1-yl)methyl)phenyl)-5-methoxy-6-methylnicotinamide;

N-(5-chloro-2-methyl-3-(((R)-3-methyl-4-((R)-tetrahydro-furan-2-carbonyl)piperazin-1-yl)methyl)phenyl)-5-fluoro-6-methylnicotinamide;

N-(5-chloro-2-methyl-3-(((R)-3-methyl-4-((S)-tetrahydro-furan-2-carbonyl)piperazin-1-yl)methyl)phenyl)-5-fluoro-6-methylnicotinamide;

N-(5-chloro-2-methyl-3-(((R)-3-methyl-4-((S)-tetrahydro-furan-3-carbonyl)piperazin-1-yl)methyl)phenyl)-5-fluoro-6-methylnicotinamide;

N-(5-chloro-2-methyl-3-(((R)-3-methyl-4-((R)-tetrahydro-furan-3-carbonyl)piperazin-1-yl)methyl)phenyl)-5-fluoro-6-methylnicotinamide; and 5-((5-chloro-2-methyl-3-(((S)-3-methyl-4-((R)-tetrahydro-furan-3-carbonyl)piperazin-1-yl)methyl)phenyl)carbamoyl)-3-fluoro-2-methylpyridine 1-oxide;

or a pharmaceutically acceptable salt thereof.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may be present as a free base or free acid.

In certain embodiments, compounds according to Formula I may contain an acidic functional group. In certain other embodiments, compounds according to Formula I may contain a basic functional group. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts may impart greater stability or solubility to the molecule thereby facilitating formulation into a dosage form. Accordingly, the invention is further directed to the use of pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively. Suitable pharmaceutically acceptable salts include those described by Berge, Bighley, and Monkhouse, *J. Pharm. Sci.* (1977) 66, pp 1-19.

Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing an acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as trifluoroacetate, while not in themselves pharmaceutically acceptable, may be useful in the preparation of salts useful as intermediates in obtaining the compounds of the invention and their pharmaceutically acceptable salts.

If a compound of the invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

Similarly, if a compound of the invention containing an acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

As used herein, the term "compounds of the invention" means both the compounds according to Formula I (as a free base or free acid) and the pharmaceutically-acceptable salts thereof. The term "a compound of the invention" also appears herein and refers to both a compound according to Formula I (as a free base or free acid) and its pharmaceutically-acceptable salts.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). Commercially available deuterated starting materials may be employed in the preparation of deuterated forms of the compounds of Formula (I), or they may be synthesized using conventional techniques employing deuterated reagents (e.g. lithium aluminum deuteride).

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compounds of Formula I and pharmaceutically acceptable salts thereof may be employed alone or in combination with other therapeutic agents. Combination therapies according to the present invention thus comprise the administration of at least one compound of Formula I or a pharmaceutically acceptable salt thereof, and the use of at least one other therapeutically active agent. A compound of Formula I or pharmaceutically acceptable salt thereof, and the other therapeutically active agent(s) may be administered together in a single pharmaceutical composition or separately and, when administered separately this may occur simultaneously or sequentially in any order.

In a further aspect, there is provided a combination product comprising a compound of Formula I or a pharmaceutically acceptable salt thereof, together with one or more other therapeutically active agents, and optionally a pharmaceutically acceptable carrier or excipient.

Suitable other therapeutic agents include, but are not limited to, (1) TNF-alpha inhibitors; (2) non-selective COX-1/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors, such as belimumab, and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine H1 receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitors tocilizumab or sirukumab, IL-12/IL-23 inhibitor ustekinumab, IL-23 inhibitor guselkumab, and anti-IL17 antibodies; (18) anti-GM-CSF antibodies; (19) checkpoint blockade and other immunotherapies, such as anti-PD-1/ anti-PD-L1 antibodies, including pembrolizumab and nivolumab, and anti-CTLA4 antibodies, including ipilimumab; (20) BET inhibitors, such as GSK525762; and (21) other oncology agents, such as fluorouracil, bevacizumab, irinotecan hydrochloride, capecitabine, cetuximab, ramucirumab, oxaliplatin, leucovorin calcium, panitumumab, regorafenib, ziv-aflibercept, trastuzumab, imatinib mesylate, sunitinib malate, sorafenib tosylate, paclitaxel, everolimus, erlotinib hydrochloride, gemcitabine hydrochloride, mitomycin C, dabrafenib, trametinib, lapatinib, ofatumumab, topotecan, doxorubicin hydrochloride, and ibrutinib.

Compound Preparation

The compounds according to Formula I may be prepared using conventional organic syntheses. Suitable synthetic routes are depicted below in the following general reaction scheme.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

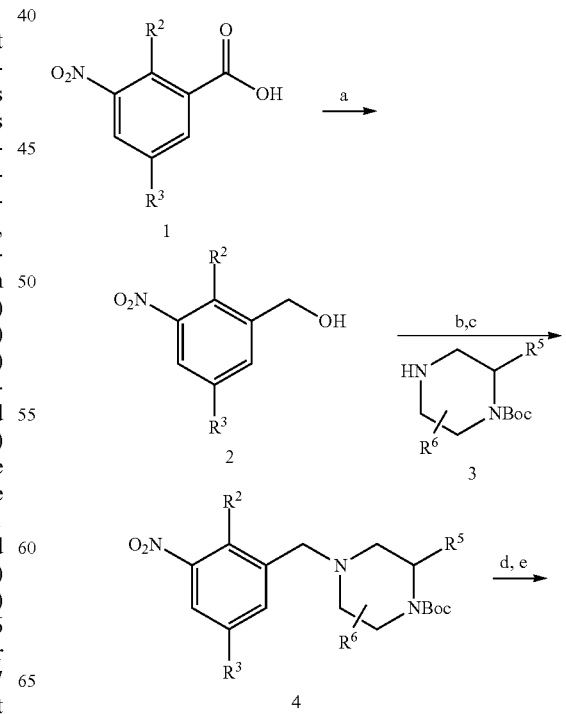

Scheme 1

-continued

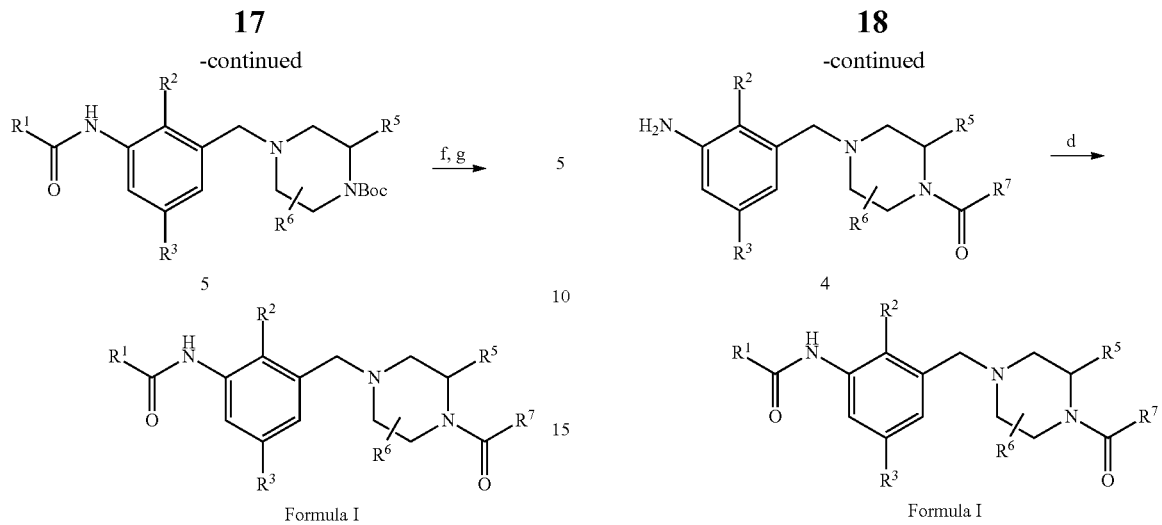

Formula I

[Exemplary conditions: a) BH₃.THF, THF, 0° C.-RT; b) PCC, CH₂Cl₂; c) NaBH(OAc)₃, HOAc, DCM, 3; d) Pd, H₂, ethanol, RT; e) R¹CO₂H, HOBt, EDC, DMF; f) TFA, DCM; g) R⁷CO₂H, HOBt, EDC, DMF].

Scheme 1 represents a general reaction scheme for preparing compounds of Formula I where R¹ to R⁷ are as defined above. The starting material or reagents described are either commercially available or made from commercially available starting materials using methods known to those skilled in the art.

Benzoic acids 1 was reduced by BH₃.THF to provide benzyl alcohols 2. Alcohols 2 were oxidized by PCC to corresponding aldehydes followed by reductive amination with 3 to provide nitro compounds 4. Reduction of nitro compounds 4 with Pd in the presence of H₂ afforded the amines which were reacted with various acids to give amides 5. The Boc protection of 5 was removed by treatment with TFA and the resulting amines reacted with various acids to provide final compounds of Formula I.

Scheme 2

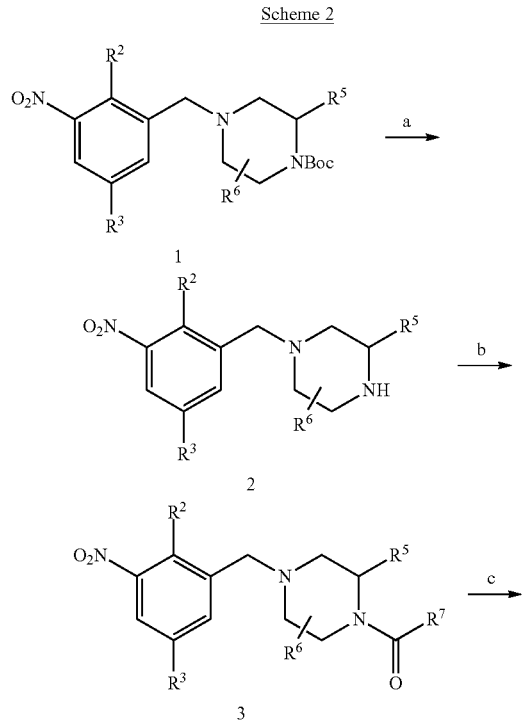

[Exemplary conditions: a) TFA, DCM, RT; b) HATU, DIPEA, DMF; c) SnCl₂.2H₂O, ethanol, RT; d) R¹CO₂H, HATU, DIPEA, DMF].

Scheme 2 represents another reaction scheme for preparing compounds of Formula I where R¹ to R⁷ are as defined above. The starting material or reagents described are either commercially available or made from commercially available starting materials using methods known to those skilled in the art.

Boc protection on nitro compounds 1 was removed by TFA to provide nitro amines 2, which could then be reacted with varies acids to give nitro amides 3. The nitro group was reduced to amine by tin(II) chloride dehydrate to afford the key intermediates 4 which were then condensed with various acids to afford final compounds of Formula I.

EXAMPLES

Abbreviations

ACN acetonitrile
DCE 1,2-dichloroethane
DCM dichloromethane
DIPEA N,N-diisopropylethylamine
DMAP N,N-dimethylpyridin-4-amine
DME 1,2-dimethoxyethane
DMF N,N-dimethylformamide
DMSO dimethylsulphoxide
DPPP 1,3-bis(diphenylphosphino)propane
EA ethyl acetate
EDC N-(3-dimethylaminopropyl)-N'-ethylcarbodiimide hydrochloride
ESI electrospray ionization
HATU O-(7-azabenzotriazol-1-yl)-N,N,N',N'-tetramethyluronium hexafluorophosphate
HOBt hydroxybenzotriazole
HPLC high-performance liquid chromatography
LCMS liquid chromatography mass spectrometry
MDAP mass directed automated preparative liquid chromatography.
MS mass spectrometry
NMP N-methyl-2-pyrrolidone
PE petroleum ether
PCC pyridinium chlorochromate
PG protecting group
RT room temperature
sat. saturated SM starting material
TEA triethylamine
TFA trifluoroacetic acid
TFAA trifluoroacetic anhydride
THF tetrahydrofuran
TMSCN trimethylsilyl cyanide
Chromatography
Unless stated otherwise, all chromatography was carried out using silica columns.
LCMS Conditions:
1) Acidic Conditions:
  Mobile phase: water containing 0.05% TFA/acetonitrile
  Column: Agilent SB-C18 4.6×30 mm 1.8 m;
  Detection: MS and photodiode array detector (PDA)
2) Basic Conditions:
  Mobile phase: 10 mM $NH_4HCO_3$ aqueous/acetonitrile
  Column: Waters XBridge C18 4.6×50 mm 3.5 m;
  Detection: MS and photodiode array detector (PDA)
MDAP Conditions:
1) Acidic Conditions:
  Instrument: Waters Mass Directed Auto-purification System
  Column: Waters Sunfire Prep C18 column (5 um, 19×50 mm)
  Mobile phase: water containing 0.05% TFA/acetonitrile.
2) Basic Conditions:
  Instrument: Mass Directed Auto-purification System
  Column: Xbridge Prep C18 column (5 um, 19×50 mm)
  Mobile phase: water containing 0.05% ammonia/acetonitrile.

In the procedures that follow, after each starting material, reference to an intermediate is typically provided. This is provided merely for assistance to the skilled chemist. The starting material may not necessarily have been prepared from the batch referred to.

Description 1 methyl 5,6-dichloronicotinate (D1)

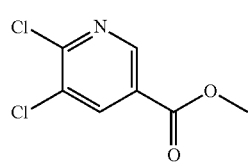

A mixture of 5,6-dichloronicotinic acid (5 g) and sulfurous dichloride (3.10 g) in methanol (20 mL) was stirred at 25° C. overnight. Cold water (100 mL) was added and the resulting mixture was neutralized with sat. $NaHCO_3$ solution. The aqueous layer was extracted with DCM (2×100 mL) and the combined organic layers were dried over $Na_2SO_4$. After filtration, the filtrate was concentrated in vacuo to give the title compound (5 g) as a white solid. MS (ESI): $C_7H_5Cl_2NO_2$ requires 205; found 206 $[M+H]^+$.

Description 2 methyl 5,6-dimethylnicotinate (D2)

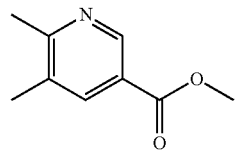

A mixture of $K_2CO_3$ (1.342 g), tricyclohexylphosphine (0.272 g), $Pd_2(dba)_3$ (0.444 g), methylboronic acid (0.291 g) and methyl 5,6-dichloronicotinate (D1, 1 g) in 1,4-dioxane (20 mL) was heated to 110° C. overnight. Cold water (30 mL) was added and the aqueous layer was extracted with DCM (2×100 mL). The combined organic layers were dried over $Na_2SO_4$, filtered and concentrated in vacuo. The resulting residue was purified by column chromatography (eluting with EA:PE=0% to 50%) to give the title compound (1 g) as a yellow oil. MS (ESI): $C_9H_{11}NO_2$ requires 165; found 166 $[M+H]^+$.

Description 3

5,6-dimethylnicotinic acid (D3)

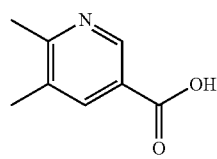

A mixture of sodium hydroxide (121 mg) and methyl 5,6-dimethylnicotinate (D2, 500 mg) in methanol (10 mL) and water (10 mL) was stirred for 2 hours. Cold water (50 mL) was added and the pH value of the resulting mixture was adjusted to 5 by HCl solution (7 M). The aqueous layer was extracted with DCM (2×100 mL). The combined organic layers were dried over $Na_2SO_4$, filtered and concentrated in vacuo to give the title compound (400 mg) as a white solid. MS (ESI): $C_8H_9NO_2$ requires 151; found 152 $[M+H]^+$.

Description 4 methyl 5-chloro-6-methylnicotinate (D4)

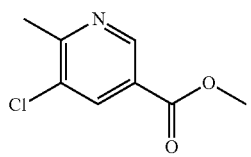

A mixture of methyl 5,6-dichloronicotinate (D1, 2 g), methylboronic acid (0.581 g), $K_2CO_3$ (2.68 g) and $Pd(PPh_3)_4$ (0.561 g) in 1,4-dioxane (100 mL) was stirred at 75° C. overnight. The resulting mixture was filtered and the filtrate was concentrated in vacuo to give the crude product, which was further purified by column chromatography (eluting with EA:PE=50% to 100%) to give the title compound (420 mg) as a yellow solid. MS (ESI): $C_8H_8ClNO_2$ requires 185; found 186 $[M+H]^+$.

Description 5

5-chloro-6-methylnicotinic acid (D5)

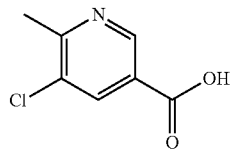

A mixture of methyl 5-chloro-6-methylnicotinate (D4, 450 mg), sodium hydroxide (485 mg) in methanol (20 mL) and water (5 mL) was stirred at RT for 1 hour. HCl solution (4 M) was used to adjust the pH value to 4. The solution was concentrated and extracted with EA (20 mL). The organic phase was washed with water (2×10 mL), dried over $Na_2SO_4$ and concentrated in vacuo to give the title compound (400 mg) as a white solid. MS (ESI): $C_7H_6ClNO_2$ requires 171; found 172 $[M+H]^+$.

Description 6

5-bromo-3-methylpicolinonitrile (D6)

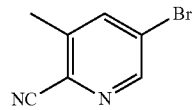

To a solution of 2,5-dibromo-3-methylpyridine (5 g) in DMF (20 mL) was added cyanocopper (1.785 g). The mixture was stirred at 120° C. overnight and then cooled to RT. The mixture was partitioned between EA (50 mL) and water (50 mL). The organic layer was washed with brine (50 mL), dried over $Na_2SO_4$ and concentrated in vacuo. The resulting residue was purified by column chromatography (eluting with EA:PE=20%) to afford the title compound (600 mg) as a white solid. MS (ESI): $C_7H_5BrN_2$ requires 195; found 196 $[M+H]^+$.

Description 7 methyl 6-cyano-5-methylnicotinate (D7)

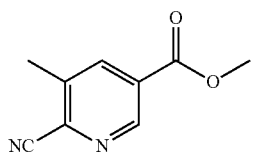

A mixture of 5-bromo-3-methylpicolinonitrile (D6, 700 mg), Pd(OAc)$_2$ (160 mg), DPPP (394 mg) and TEA (1.486 mL) in methanol (12 mL) and DMF (3 mL) was heated to 120° C. for 12 hours under a CO atmosphere (10 atm). After cooling to RT, the mixture was concentrated in vacuo. The residue was purified by column chromatography (eluting with EA:PE=20%) to afford the title compound (300 mg) as a sticky oil. MS (ESI): $C_9H_8N_2O_2$ requires 176; found 177 $[M+H]^+$.

Description 8

6-cyano-5-methylnicotinic acid (D8)

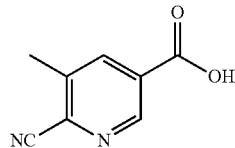

A mixture of methyl 6-cyano-5-methylnicotinate (D7, 250 mg) and LiOH (68.0 mg) in THF (15 mL) and water (5 mL) was stirred at RT overnight. The mixture was partitioned between water (10 mL) and EA (16 mL). The aqueous phase was acidified by HCl solution (1 M) to adjust the pH value to about 6, and then extracted with EA (20 mL). The resulting organic phase was dried over $Na_2SO_4$, filtered and concentrated in vacuo to afford the title compound (160 mg) as a pale solid. MS (ESI): $C_8H_6N_2O_2$ requires 162; found 163 $[M+H]^+$.

Description 9

3-carboxy-5-fluoropyridine 1-oxide (D9)

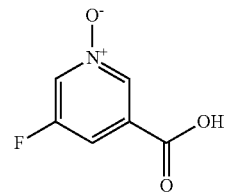

To a solution of 5-fluoronicotinic acid (2 g) in $(CH_3CO)_2O$ (5 mL) and acetic acid (5 mL) was added aqueous hydrogen peroxide solution (30%, 4.82 g). The mixture was stirred at 110° C. for 2 hours and then cooled to RT. Water (50 mL) was added. The mixture was extracted with EA (3×50 mL). The combined organic layers were washed with sat. NaHCO$_3$ solution (50 mL), water (50 mL) and brine (50 mL). The solution was dried over MgSO$_4$ and evaporated in vacuo to give the title compound (2 g) as a white solid. MS (ESI): $C_6H_4FNO_3$ requires 157; found 158 $[M+H]^+$.

Description 10 ethyl 5-cyano-2-hydroxy-6-methylnicotinate (D10)

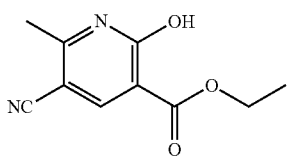

A mixture of diethyl 2-(ethoxymethylene)malonate (21.6 g) and (E)-3-aminobut-2-enenitrile (8.20 g) in a round bottom flask was stirred at 150° C. for 2 hours and standing overnight. The mixture was filtered. The precipitate was washed with ice-cold methanol to give the title compound (5 g) as a yellow solid. MS (ESI): $C_{10}H_{10}N_2O_3$ requires 206; found 207 $[M+H]^+$.

Description 11 ethyl 2-chloro-5-cyano-6-methylnicotinate (D11)

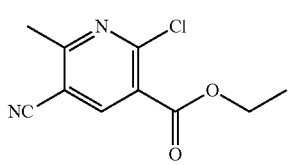

A mixture of ethyl 5-cyano-2-hydroxy-6-methylnicotinate (D10, 3 mg) and phosphoryl trichloride (22.3 mg) in a round bottom flask was stirred at 90° C. for 5 hours and standing overnight. The solution was concentrated in vacuo. The residue was poured into ice. The resulting mixture was filtered to afford the title compound (3 g) as a yellow solid. MS (ESI): $C_{10}H_9ClN_2O_2$ requires 224; found 225 $[M+H]^+$.

Description 12 ethyl 5-cyano-6-methylnicotinate (D12)

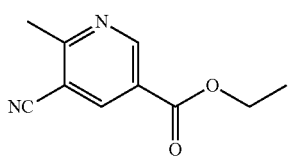

To a mixture of ethyl 2-chloro-5-cyano-6-methylnicotinate (D11, 1.5 g), methanol (50 mL) and palladium (10% on carbon, 0.071 g) was added ammonium formate (6.32 g). The mixture was stirred at RT for 3 hours, and then filtered. The solution was concentrated in vacuo. The residue was purified by column chromatography (eluting with PE:EA=20%) to give the title compound (1 g) as a white solid. MS (ESI): $C_{10}H_{10}N_2O_2$ requires 190; found 191 $[M+H]^+$.

Description 13

5-cyano-6-methylnicotinic acid (D13)

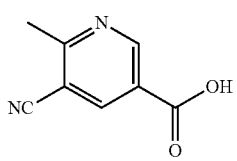

To a mixture of ethyl 5-cyano-6-methylnicotinate (D12, 1 g), methanol (15 mL) and water (30 mL) was added sodium hydroxide (2.103 g). The mixture was stirred at RT for 30 mins. The pH of the solution was adjusted to 4 with hydrochloric acid. The mixture was washed with EA (2×100 mL). The combined organic layers were concentrated in vacuo to give the title compound (800 mg) as a white solid. $^1$H NMR (400 MHz, MeOD-$d_4$): 9.20 (s, 1H), 8.62 (s, 1H), 2.83 (s, 3H). MS (ESI): $C_8H_6N_2O_2$ requires 162; found 163 $[M+H]^+$.

Description 14 methyl 2,6-dichloro-5-fluoronicotinate (D14)

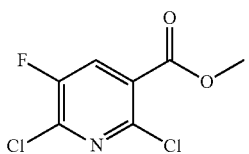

To a mixture of 2,6-dichloro-5-fluoronicotinic acid (5 g) and one drop of DMF in DCM (20 mL) was added dropwise oxalyl chloride (5 mL) at RT. The mixture was stirred at RT for 1 hour, and then concentrated. The resulting acyl chloride was again dissolved in DCM (10 mL), and then added dropwise to a mixture of DCM (20 mL) and MeOH (20 mL). The resulting mixture was stirred at RT for another 1 hour, and then concentrated to afford the title compound (6 g) as an oil. MS (ESI): $C_7H_4Cl_2FNO_2$ requires 223; found 224 $[M+H]^+$.

Description 15 methyl 2-chloro-5-fluoro-6-methylnicotinate (D15)

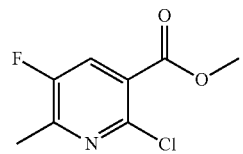

A mixture of methyl 2,6-dichloro-5-fluoronicotinate (D14, 6 g), 2,4,6-trimethyl-1,3,5,2,4,6-trioxatriborinane (3.36 g), $K_2CO_3$ (9.99 g) and Pd(Ph$_3$P)$_4$ (1.548 g) in 1,4-dioxane (50 mL) was heated to 110° C. for 20 hours. The mixture was filtered, and the filtrate was concentrated. The residue was purified by column chromatography (eluting with EA:PE=1:10) to afford the title compound (3.5 g) as an oil. MS (ESI): $C_8H_7ClFNO_2$ requires 203; found 204 $[M+H]^+$.

Description 16 methyl 5-fluoro-6-methylnicotinate (D16)

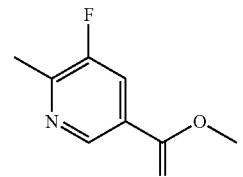

A mixture of methyl 2-chloro-5-fluoro-6-methylnicotinate (D15, 4.2 g), Pd/C (0.5 g) and sodium acetate (6.77 g) in EA (50 mL) was stirred at RT overnight under a hydrogen atmosphere (1 atm). The mixture was filtered, and the filtrate was concentrated. The residue was purified by column chromatography (eluting with EA:PE=1:10) to afford the title compound (3.5 g) as a white solid. MS (ESI): $C_8H_8FNO_2$ requires 169; found 170 $[M+H]^+$.

Description 17

5-fluoro-6-methylnicotinic acid (D17)

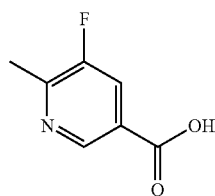

To a solution of methyl 5-fluoro-6-methylnicotinate (D16, 2.3 g) in THF (10 mL) and methanol (10 mL) was added a solution of NaOH (0.707 g) in water (5 mL). The mixture was stirred at RT for 1 hour, and then concentrated under vacuum. To the residue was added water (5 mL). The pH of the mixture was adjusted to 3. The solid was collected and dried under vacuum to afford the title compound (800 mg) as a white solid. $^1$H NMR (400 MHz, DMSO-$d_6$): 8.83 (s, 1H), 8.00 (dd, J=1.2 Hz, 9.6 Hz, 1H), 2.57 (s, 3H). MS (ESI): $C_7H_6FNO_2$ requires 155; found 156 $[M+H]^+$.

Description 18

3-cyano-4-methylbenzoic acid (D18)

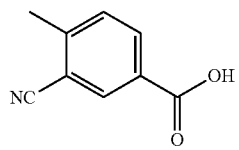

To a mixture of 3-iodo-4-methylbenzoic acid (3.0 g) and copper(I) cyanide (1.333 g) in DMF (12 mL) stirred at 100° C. for 20 hours. The mixture was poured into ice water and extracted with EA. The organic phase was concentrated. The residue was washed with a mixed solvent of PE:EA (5:1) to give the title compound (800 mg) as a green solid. MS (ESI): $C_9H_7NO_2$ requires 161; found 160 $[M-H]^-$.

Description 19

5-fluoro-2-methyl-3-nitrobenzoic acid (D19)

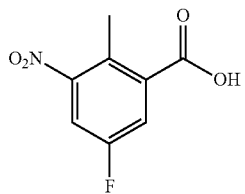

5-Fluoro-2-methylbenzoic acid (20 g) was added portionwise to ice-cooled conc. sulfuric acid (98%, 80 mL). The mixture was stirred at 0° C. until all solid dissolved. A mixture of nitric acid (65%, 6 mL) and $H_2SO_4$ (98%, 12 mL) was added portionwise, and then allowed to warm gradually to RT. The resulting mixture was stirred at RT for 6 hours, and then poured into ice (500 mL). The solid was collected and washed with water (100 mL). The solid was redissolved in EA (200 mL) and washed with brine. The organic layer was dried over anhydrous $Na_2SO_4$ and concentrated in vacuo to afford the title compound (11 g) as a brown solid. MS (ESI): $C_8H_6FNO_4$ requires 199; found 198 $[M-H]^-$.

Description 20

5-chloro-2-methyl-3-nitrobenzoic acid (D20)

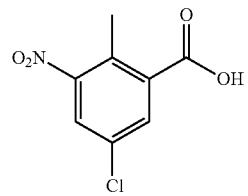

To a solution of 5-chloro-2-methylbenzoic acid (50 g) in conc. $H_2SO_4$ (300 mL) at 0° C. was added a mixture of nitric acid (65%, 1.92 g) and conc. sulfuric acid (50 mL) portionwise. The mixture was stirred for 6 hours, and then poured into ice (1 kg). The resulting mixture was diluted with water (100 mL). After filtration, the solid was collected and redissolved in EA (300 mL). The solution was washed with brine, dried over $Na_2SO_4$, filtered and concentrated in vacuo. The residue was washed with EA and PE (2:1, 50 mL) twice to afford the title compound (39 g) as a yellow solid. MS (ESI): $C_8H_6ClNO_4$ requires 215; found 216 $[M+H]^+$.

Description 21

(5-fluoro-2-methyl-3-nitrophenyl) methanol (D21)

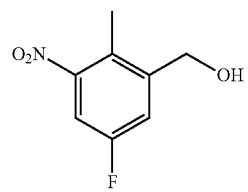

A mixture of 5-fluoro-2-methyl-3-nitrobenzoic acid (D19, 11 g) and $BH_3$.THF (1 M in THF, 72 mL) was heated to 80° C. for 2 hours. MeOH (20 mL) was added slowly to the mixture to quench the reaction. The resulting solution was concentrated in vacuo. The residue was dissolved in DCM (50 mL) and washed with sat. $NaHCO_3$ solution (2×50 mL) and brine (2×50 mL). The organic phase was dried over $Na_2SO_4$, filtered and concentrated to afford the title compound (9 g) as a yellow solid. MS (ESI): $C_8H_8FNO_3$ requires 185; found no mass.

Description 22

(5-chloro-2-methyl-3-nitrophenyl) methanol (D22)

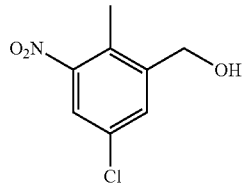

To a mixture of 5-chloro-2-methyl-3-nitrobenzoic acid (D20, 10.7 g) in THF (60 mL) was added BH$_3$.THF (1M in THF, 99 mL) portionwise at 0° C. The mixture was warmed gradually to RT and stirred for 5 hours. MeOH (50 mL) was added slowly to the mixture. The mixture was concentrated in vacuo to afford the title compound (8.5 g). $^1$H NMR (400 MHz, CDCl$_3$): 7.67 (s, 1H), 7.65 (s, 1H), 4.73 (d, 2H), 2.33 (s, 3H).

Description 23

5-chloro-1-(chloromethyl)-2-methyl-3-nitrobenzene (D23)

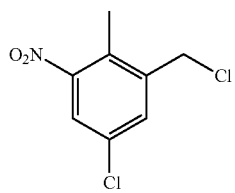

(5-Chloro-2-methyl-3-nitrophenyl) methanol (D22, 7 g) was dissolved in sulfurous dichloride (24.78 g). After stirring at 80° C. overnight, the mixture was concentrated to give the title compound (7 g) as a yellow solid. MS (ESI): C$_8$H$_7$Cl$_2$NO$_2$ requires 219; found no mass.

Description 24

5-fluoro-2-methyl-3-nitrobenzaldehyde (D24)

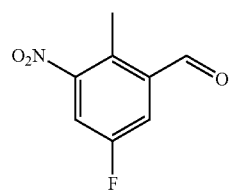

To a mixture of (5-fluoro-2-methyl-3-nitrophenyl) methanol (D21, 9 g) in DCM (100 mL) was added PCC (14 g) portionwise. The mixture was stirred at RT overnight. The solvent was removed in vacuo to give the crude product, which was purified by column chromatography (eluting with EA:PE=5%) to afford the title compound (5 g) as a pale yellow solid. MS (ESI): C$_8$H$_6$FNO$_3$ requires 185; found no mass.

Description 25

(S)-tert-butyl 4-(5-chloro-2-methyl-3-nitrobenzoyl)-2-methylpiperazine-1-carboxylate (D25)

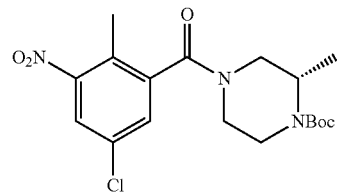 [SMILES: Cc1c(C(=O)N2CCN(C(=O)OC(C)(C)C)[C@@H](C)C2)cc(Cl)cc1[N+](=O)[O-]]

To a solution of 5-chloro-2-methyl-3-nitrobenzoic acid (D20, 32.3 g), (S)-tert-butyl 2-methylpiperazine-1-carboxylate (25 g) and DIPEA (43.6 mL) in DMF (100 mL) was added HATU (57.0 g) at 0° C. The mixture was stirred at RT overnight, and then poured into water. The resulting mixture was filtered. The solid was dissolved in EA, and washed with brine for three times. The solution was dried with Na$_2$SO$_4$ and concentrated under vacuum to give the title compound (47 g) as a light orange solid. MS (ESI): C$_{18}$H$_{24}$ClN$_3$O$_5$ requires 397; found 342 [M−tBu+H+H]$^+$.

Description 26

(S)-tert-butyl 4-(5-fluoro-2-methyl-3-nitrobenzyl)-2-methylpiperazine-1-carboxylate (D26)

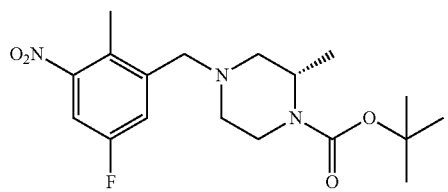 [SMILES: Cc1c(CN2CCN(C(=O)OC(C)(C)C)[C@@H](C)C2)cc(F)cc1[N+](=O)[O-]]

To a solution of 5-fluoro-2-methyl-3-nitrobenzaldehyde (D24, 10 g) and (S)-tert-butyl 2-methylpiperazine-1-carboxylate (12.03 g) in DCM (120 mL) was added drops of acetic acid (3.28 g). The mixture was stirred at RT for an hour. Sodium triacetoxyhydroborate (23.15 g) was added in ice bath. The mixture was stirred at RT overnight and quenched with sat. NaHCO$_3$ solution. The organic layer was dried with anhydrous Na$_2$SO$_4$, filtered and concentrated in vacuo to give the title compound (22.17 g) as a syrup. MS (ESI): C$_{18}$H$_{26}$FN$_3$O$_4$ requires 367; found 368 [M+H]$^+$.

Description 27

(S)-tert-butyl 4-(5-chloro-2-methyl-3-nitrobenzyl)-2-methylpiperazine-1-carboxylate (D27)

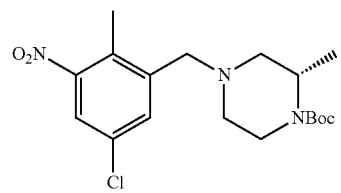 [SMILES: Cc1c(CN2CCN(C(=O)OC(C)(C)C)[C@@H](C)C2)cc(Cl)cc1[N+](=O)[O-]]

BH$_3$.THF (1.0 M in THF, 151 mL) was added dropwise to a solution of (S)-tert-butyl 4-(5-chloro-2-methyl-3-nitrobenzoyl)-2-methylpiperazine-1-carboxylate (D25, 30 g) in THF (200 mL) at 0° C. in 10 mins. The reaction mixture was heated to 75° C. and stirred for 1 hour. The resulting mixture was concentrated to give the title compound (28 g) as a yellow oil. MS (ESI): C$_{18}$H$_{26}$ClN$_3$O$_4$ requires 383; found 384 [M+H]$^+$.

Description 28

(S)-tert-butyl 4-(5-chloro-2-methyl-3-nitrobenzyl)-2-ethylpiperazine-1-carboxylate (D28)

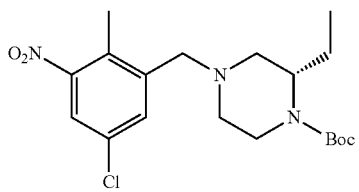 [SMILES: CC[C@H]1CN(Cc2cc(Cl)cc([N+](=O)[O-])c2C)CCN1C(=O)OC(C)(C)C]

To a solution of 5-chloro-1-(chloromethyl)-2-methyl-3-nitrobenzene (D23, 1.232 g) in DMF (20 mL) were added (S)-tert-butyl 2-ethylpiperazine-1-carboxylate (1 g) and K$_2$CO$_3$ (1.935 g) at 60° C. After stirring overnight, the mixture was poured into ice/water, and then extracted with DCM (3×100 mL). The combined organic layers were dried over Na$_2$SO$_4$, filtered and concentrated to give a yellow oil, which was purified by column chromatography (eluting with EA:PE=5%) to give the title compound (1.3 g) as a yellow solid. MS (ESI): C$_{19}$H$_{28}$ClN$_3$O$_4$ requires 397; found 398 [M+H]$^+$.

Description 29

(S)-tert-butyl 4-(3-amino-5-fluoro-2-methylbenzyl)-2-methylpiperazine-1-carboxylate (D29)

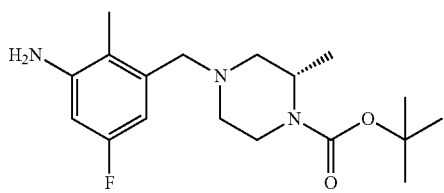

To a solution of (S)-tert-butyl 4-(5-fluoro-2-methyl-3-nitrobenzyl)-2-methylpiperazine-1-carboxylate (D26, 5 g) in ethanol (65 mL) was added palladium (0.145 g) under H$_2$. The mixture was stirred at RT for 24 hours, and then filtered. The filtrate was evaporated in vacuo to give the title compound (4.5 g). MS (ESI): C$_{18}$H$_{28}$FN$_3$O$_2$ requires 337; found 338 [M+H]$^+$.

Description 30

(S)-tert-butyl 4-(3-amino-5-chloro-2-methylbenzyl)-2-methylpiperazine-1-carboxylate (D30)

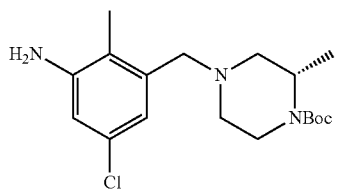

To a solution of (S)-tert-butyl 4-(5-chloro-2-methyl-3-nitrobenzyl)-2-methylpiperazine-1-carboxylate (D27, 30 g) and nickel (4.59 g) in methanol (200 mL) stirred under a nitrogen atmosphere at 50° C. was added hydrazine (80%, 12.26 mL). The reaction mixture was stirred at 50° C. for 1 hour. The catalyst was filtered, and the filtrate was concentrated. The residue was dried under vacuum to yield the title compound (27 g) as a light yellow oil. MS (ESI): C$_{18}$H$_{28}$ClN$_3$O$_2$ requires 353; found 354 [M+H]$^+$.

Description 31

(S)-1-(5-fluoro-2-methyl-3-nitrobenzyl)-3-methylpiperazine, 2 hydrochloric acid salt (D31)

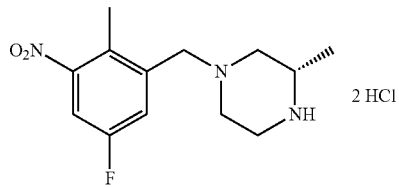 [SMILES: Cc1c(CN2CCN[C@@H](C)C2)cc(F)cc1[N+](=O)[O-]]

To a solution of (S)-tert-butyl 4-(5-fluoro-2-methyl-3-nitrobenzyl)-2-methylpiperazine-1-carboxylate (D26, 4 g) in DCM (15 mL) was added HCl/MeOH (27.2 mL). The mixture was degassed and stirred under a nitrogen atmosphere at RT for 12 hours. The mixture was concentrated to afford the title compound (3.1 g). MS (ESI): C$_{13}$H$_{18}$FN$_3$O$_2$ requires 267; found 268 [M+H]$^+$.

Description 32

(S)-1-(5-chloro-2-methyl-3-nitrobenzyl)-3-methylpiperazine (D32)

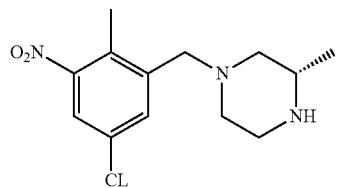

To a solution of (S)-tert-butyl 4-(5-chloro-2-methyl-3-nitrobenzyl)-2-methylpiperazine-1-carboxylate (D27, 1.5138 g) in DCM (15 mL) was added TFA (3.04 mL) dropwise. The resulting mixture was stirred at RT overnight. The solvent was removed under vacuum. The residue was diluted with DCM (10 mL), and basified with sat. Na$_2$CO$_3$ solution to pH=9. NaOH solution (2 M) was added to adjust pH to 11. The aqueous phase was separated, and extracted with DCM (2×15 mL). The combined organic layers were dried over Na$_2$SO$_4$, filtered and concentrated to afford the title compound (1.17 g) as a pale yellow oil. MS (ESI): C$_{13}$H$_{18}$ClN$_3$O$_2$ requires 283; found 284 [M+H]$^+$.

Description 33

(S)-1-(5-chloro-2-methyl-3-nitrobenzyl)-3-ethylpiperazine, 2 hydrochloric acid salt (D33)

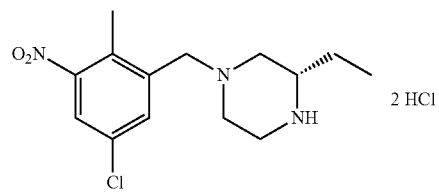 [SMILES: CC[C@H]1CN(Cc2cc(Cl)cc([N+](=O)[O-])c2C)CCN1]

To a solution of (S)-tert-butyl 4-(5-chloro-2-methyl-3-nitrobenzyl)-2-ethylpiperazine-1-carboxylate (D28, 1.3 g) in methanol (30 mL) was added HCl (1.191 g) in MeOH. The mixture was stirred at RT for 18 hours, and then concentrated in vacuo to give the title compound (900 mg) as a white solid. MS (ESI): $C_{14}H_{20}ClN_3O_2$ requires 297; found 298 $[M+H]^+$.

Description 34

(S)-tert-butyl 4-(5-chloro-3-(3-cyanobenzamido)-2-methylbenzyl)-2-methylpiperazine-1-carboxylate (D34)

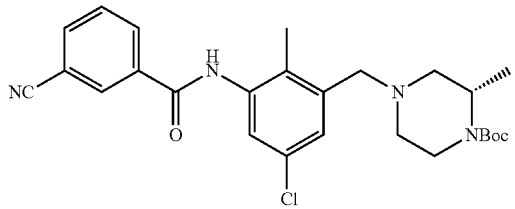

To a suspension of 3-cyanobenzoic acid (3.06 g) in DCM (30 mL) was added two drops of DMF. Oxalyl dichloride (1.948 mL) was added dropwise. The resulting mixture was stirred at RT overnight. The solvent was removed under vacuum. The residue was redissolved in acetonitrile (10 mL). The solution was added dropwise into a mixture of (S)-tert-butyl 4-(3-amino-5-chloro-2-methylbenzyl)-2-methylpiperazine-1-carboxylate (D30, 6.7 g) and potassium carbonate (7.85 g) in acetonitrile (50 mL). The mixture was stirred overnight, and then quenched with water (10 mL). The resulting mixture was filtered, and the solid was washed with DCM (20 mL). The filtrate was concentrated to dryness, and then dissolved in DCM (50 mL). The DCM solution was washed with sat. $Na_2CO_3$ solution, dried over $Na_2SO_4$ and filtered. The residue was purified by column chromatography (eluting with DCM:MeOH=1:0 to 99:1) to give the title compound (5.99 g) as an off-white foaming solid. MS (ESI): $C_{26}H_{31}ClN_4O_3$ requires 482; found 483 $[M+H]^+$.

Description 35-36

Descriptions 35 to 36 were prepared using a similar procedure to that described for Description 34.

D35: (S)-tert-butyl 4-(5-chloro-3-(6-ethylnicotinamido)-2-methylbenzyl)-2-methylpiperazine-1-carboxylate D36: (S)-tert-butyl 4-(5-chloro-2-methyl-3-(6-methylnicotinamido)benzyl)-2-methylpiperazine-1-carboxylate

| | Structure | Characterization |
|---|---|---|
| D35 | 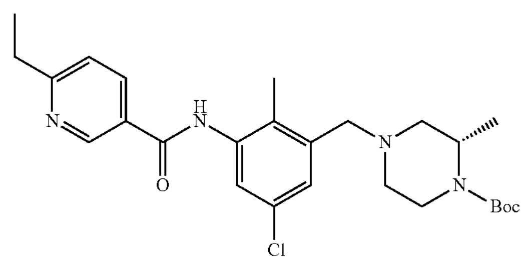 [SMILES: CCc1ccc(C(=O)Nc2cc(Cl)cc(CN3CCN(C(=O)OC(C)(C)C)[C@@H](C)C3)c2C)cn1] | MS (ESI): $C_{26}H_{35}ClN_4O_3$ requires 486; found 487 $[M + H]^+$. |
| D36 | 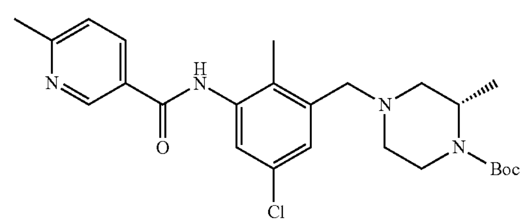 [SMILES: Cc1ccc(C(=O)Nc2cc(Cl)cc(CN3CCN(C(=O)OC(C)(C)C)[C@@H](C)C3)c2C)cn1] | MS (ESI): $C_{25}H_{33}ClN_4O_3$ requires 472; found 473 $[M + H]^+$. |

Description 37

(S)-tert-butyl 4-(5-chloro-3-(3-cyano-4-fluorobenzamido)-2-methylbenzyl)-2-methylpiperazine-1-carboxylate, trifluoroacetic acid salt (D37)

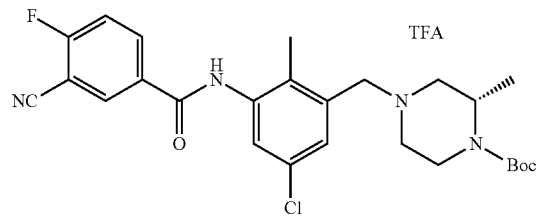 [SMILES: Cc1c(CN2CCN(C(=O)OC(C)(C)C)[C@@H](C)C2)cc(Cl)cc1NC(=O)c1ccc(F)c(C#N)c1]

To a solution of (S)-tert-butyl 4-(3-amino-5-chloro-2-methylbenzyl)-2-methylpiperazine-1-carboxylate (D30, 220.5 mg) and 3-cyano-4-fluorobenzoic acid (114.5 mg) in DCM (10 mL) was added DMAP (7.4 mg) and EDC (250.8 mg). The mixture was stirred overnight. The mixture was diluted with DCM (10 mL), and then washed with water (5 mL). The organic layer was separated and concentrated to dryness. The residue was purified by reverse phase chromatography (eluting with ACN/water (containing 0.05% TFA), ACN %=10%-95%, 50 mL/min) to give the title compound (315.3 mg) as a pale yellow solid. MS (ESI): $C_{26}H_{30}ClFN_4O_3$ requires 500; found 501 $[M+H]^+$.

Description 38-39

Descriptions 38 to 39 were prepared using a similar procedure to that described for Description 37.

D38: (S)-tert-butyl 4-(5-chloro-3-(3-cyano-4-methylbenzamido)-2-methylbenzyl)-2-methylpiperazine-1-carboxylate, trifluoroacetic acid salt D39: (S)-tert-butyl 4-(3-(3-cyanobenzamido)-5-fluoro-2-methylbenzyl)-2-methylpiperazine-1-carboxylate, trifluoroacetic acid salt

Description 40

(S)-tert-butyl 4-(5-chloro-3-(5-fluoro-6-methylnicotinamido)-2-methylbenzyl)-2-methylpiperazine-1-carboxylate (D40)

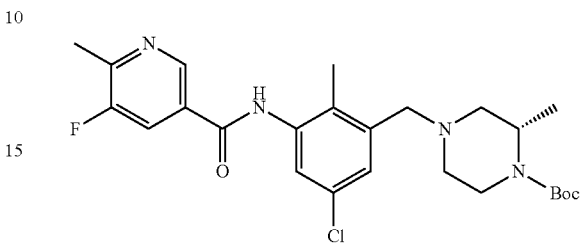

A solution of (S)-tert-butyl 4-(3-amino-5-chloro-2-methylbenzyl)-2-methylpiperazine-1-carboxylate (D30, 913 mg), 5-fluoro-6-methylnicotinic acid (D17, 400 mg), HATU (980 mg) and DIPEA (0.450 mL) in DCM (100 mL) was stirred at RT for 18 hours. The mixture was concentrated in vacuo to afford the title compound (1.2 g) as a red oil. MS (ESI): $C_{25}H_{32}ClFN_4O_3$ requires 490; found 491 $[M+H]^+$.

Description 41

Description 41 was prepared using a similar procedure to that described for Description 40, with the specified reaction base or solvent listed in the table.

D41: (S)-tert-butyl 4-(5-chloro-3-(2-cyanoisonicotinamido)-2-methylbenzyl)-2-methylpiperazine-1-carboxylate, trifluoroacetic acid salt

| | Structure | Characterization |
|---|---|---|
| D38 | 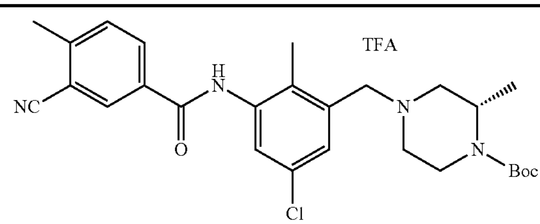 | MS (ESI): $C_{27}H_{33}ClN_4O_3$ requires 496; found 497 $[M+H]^+$. |
| D39 | 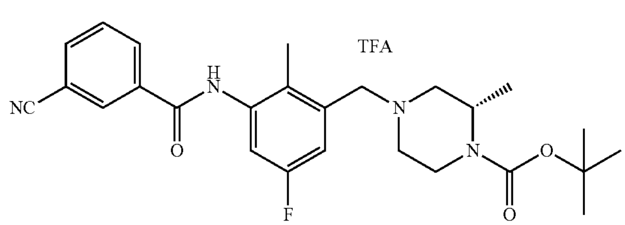 [SMILES: Cc1c(CN2CCN(C(=O)OC(C)(C)C)[C@@H](C)C2)cc(F)cc1NC(=O)c1cccc(C#N)c1] | MS (ESI): $C_{26}H_{31}FN_4O_3$ requires 466; found 467 $[M+H]^+$. |

| | Structure | Solvent/base | Characterization |
|---|---|---|---|
| D41 | 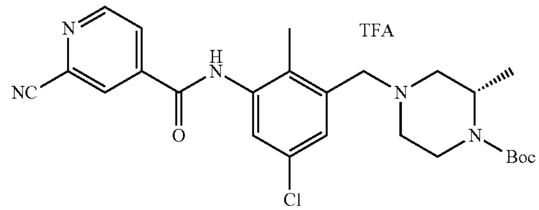 [SMILES: Cc1c(CN2CCN(C(=O)OC(C)(C)C)[C@@H](C)C2)cc(Cl)cc1NC(=O)c1ccnc(C#N)c1] | DMF/DIPEA | MS (ESI): $C_{25}H_{30}ClN_5O_3$ requires 483; found 484 $[M + H]^+$. |

Description 42

(S)-tert-butyl 4-(5-chloro-3-(5-cyano-6-methylnico-tinamido)-2-methylbenzyl)-2-methylpiperazine-1-carboxylate, trifluoroacetic acid salt (D42)

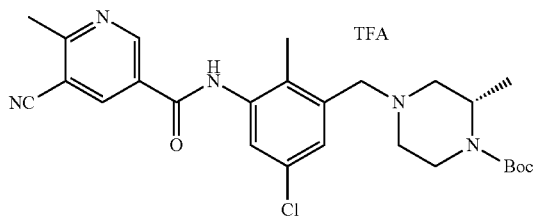 [SMILES: Cc1ncc(C(=O)Nc2cc(Cl)cc(CN3CCN(C(=O)OC(C)(C)C)[C@@H](C)C3)c2C)cc1C#N]

To a solution of (S)-tert-butyl 4-(3-amino-5-chloro-2-methylbenzyl)-2-methylpiperazine-1-carboxylate (D30, 264.5 mg) and 5-cyano-6-methylnicotinic acid (D13, 158 mg) in anhydrous DMF (5 mL), HATU (510.3 mg) and DIPEA (0.261 mL) were added, the reaction mixture was stirred over the weekend. Diluted with DCM (10 mL), washed with water twice (5 mL×2), the organic layer was concentrated to dryness, the crude product was purified with reverse phase chromatography (Biotage, SNAP Cartridge, KP-C18-HS 120 g column, ACN/water (containing 0.05% TFA), ACN %=10%-90%, 50 mL/min), giving the title compound (350.8 mg) as off-white solid. $^1$H NMR (400 MHz, CDCl$_3$) δ ppm 1.33 (d, 3H), 1.44 (s, 9H), 2.27 (s, 3H), 2.51-2.67 (m, 1H), 2.77-2.84 (m, 1H), 2.88 (s, 3H), 3.14 (d, 1H), 3.28 (br s, 1H), 3.41 (d, 1H), 3.94-4.17 (m, 3H), 4.46 (brs, 1H), 7.24 (s, 1H), 7.63 (s, 1H), 8.53 (s, 1H), 8.89 (br s, 1H), 9.25 (s, 1H). $^{19}$F NMR (376 MHz, CDCl$_3$) δ ppm −75.5. MS (ESI): $C_{26}H_{32}ClN_5O_3$ requires 497; found 498 $[M+H]^+$.

Description 43-45

Descriptions 43 to 45 were prepared using a similar procedure to that described for Description 40, with the specified reaction base or solvent listed in the table.

D43: (S)-tert-butyl 4-(5-chloro-3-(6-cyanonicotinamido)-2-methylbenzyl)-2-methylpiperazine-1-carboxylate, trifluoroacetic acid salt D44: (S)-3-((3-((4-(tert-butoxycarbonyl)-3-methylpiperazin-1-yl)methyl)-5-chloro-2-methylphenyl)carbamoyl)-5-fluoropyridine 1-oxide D45: (S)-tert-butyl 4-(5-chloro-3-(5-fluoronicotinamido)-2-methylbenzyl)-2-methylpiperazine-1-carboxylate

| | Structure | Solvent/base | Characterization |
|---|---|---|---|
| D43 | 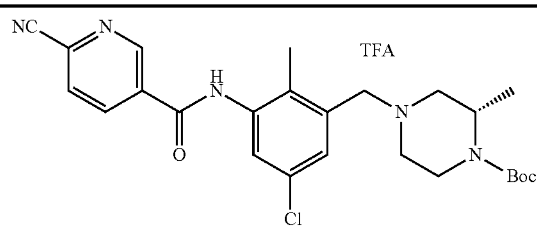 | DMF/DIPEA | MS (ESI): $C_{25}H_{30}ClN_5O_3$ requires 483; found 484 $[M + H]^+$. |
| D44 | 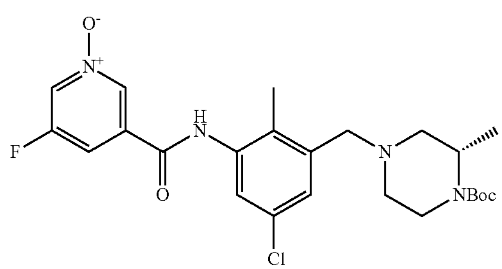 [SMILES: Cc1c(CN2CCN(C(=O)OC(C)(C)C)[C@@H](C)C2)cc(Cl)cc1NC(=O)c1cc(F)c[n+]([O-])c1] | DCM/DIPEA | MS (ESI): $C_{25}H_{35}ClN_4O_3$ requires 492; found 493 $[M + H]^+$. |
| D45 | 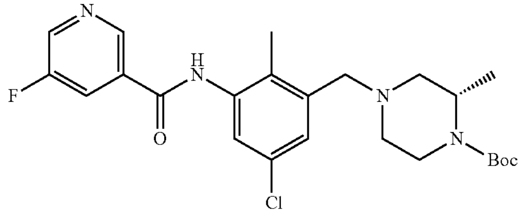 [SMILES: Cc1c(CN2CCN(C(=O)OC(C)(C)C)[C@@H](C)C2)cc(Cl)cc1NC(=O)c1cncc(F)c1] | DMF/DIPEA | MS (ESI): $C_{24}H_{30}ClFN_4O_3$ requires 476; found 477 $[M + H]^+$. |

Description 46

(S)-tert-butyl 4-(5-chloro-3-(3-cyano-5-fluorobenzamido)-2-methylbenzyl)-2-methylpiperazine-1-carboxylate (D46)

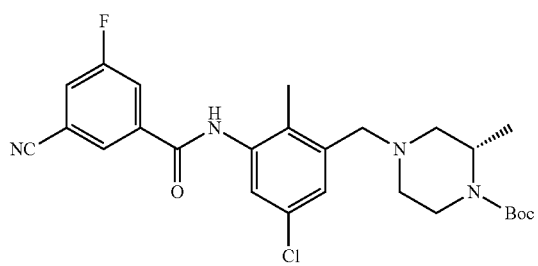 [SMILES: Cc1c(CN2CCN(C(=O)OC(C)(C)C)[C@@H](C)C2)cc(Cl)cc1NC(=O)c1cc(F)cc(C#N)c1]

To a solution of 3-cyano-5-fluorobenzoic acid (200 mg) in DCM (20 mL) was added sulfurous dichloride (288 mg). The mixture was stirred at 40° C. for 8 hours, and then concentrated to dryness under reduced pressure. The residue was redissolved in DCM (20 mL). The resulting solution was slowly added to a mixture of (S)-tert-butyl 4-(3-amino-5-chloro-2-methylbenzyl)-2-methylpiperazine-1-carboxylate (D30, 429 mg) and DIPEA (470 mg) in DCM (20 mL) at 0° C. The reaction mixture was allowed to warm to RT and stirred for 1 hour. The resulting mixture was then partitioned with water (15 mL). The organic phase was dried over $Na_2SO_4$, filtered and concentrated in vacuo to give the title compound (320 mg) as a yellow solid. MS (ESI): $C_{26}H_{30}ClFN_4O_3$ requires 500; found 501 $[M+H]^+$.

Description 47-48

Descriptions 47 to 48 were prepared using a similar procedure to that described for Description 46.
D47: (S)-tert-butyl 4-(5-chloro-2-methyl-3-(2-methylthiazole-5-carboxamido)benzyl)-2-methylpiperazine-1-carboxylate
D48: (S)-tert-butyl 4-(5-chloro-3-(6-cyano-5-methylnicotinamido)-2-methylbenzyl)-2-methylpiperazine-1-carboxylate

Description 49

(S)-tert-butyl 4-(5-chloro-3-(6-cyano-5-fluoronicotinamido)-2-methylbenzyl)-2-methylpiperazine-1-carboxylate (D49)

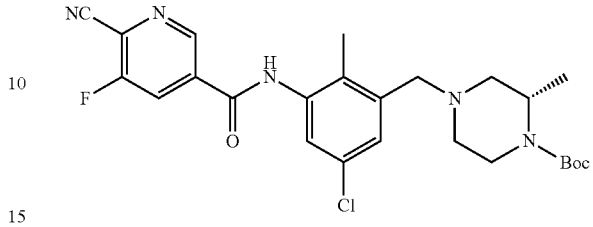

To a solution of (S)-3-((3-((4-(tert-butoxycarbonyl)-3-methylpiperazin-1-yl)methyl)-5-chloro-2-methylphenyl)carbamoyl)-5-fluoropyridine 1-oxide (D44, 500 mg) in $CH_3CN$ (20 mL) was added TMSCN (0.204 mL) and TEA (0.212 mL). The mixture was stirred at 80° C. for 2 hours. After cooling to RT, water was added. The mixture was extracted with EA (3×50 mL). The combined organic layers were washed with sat. $NaHCO_3$ solution, water and brine. The resulting solution was dried over $MgSO_4$ and filtered. The filtrate was concentrated in vacuo. The residue was purified by column chromatography (eluting with EA:PE=20%) to afford the title compound (250 mg) as a white solid. MS (ESI): $C_{25}H_{29}ClFN_5O_3$ requires 501; found 502 $[M+H]^+$.

Description 50

(S)-3-cyano-N-(5-fluoro-2-methyl-3-((3-methylpiperazin-1-yl)methyl)phenyl)benzamide (D50)

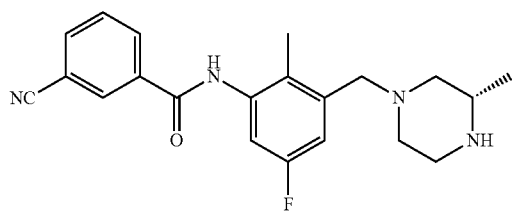 [SMILES: Cc1c(CN2CCN[C@@H](C)C2)cc(F)cc1NC(=O)c1cccc(C#N)c1]

To a solution of (S)-tert-butyl 4-(3-(3-cyanobenzamido)-5-fluoro-2-methylbenzyl)-2-methylpiperazine-1-carboxy-

| | Structure | Characterization |
|---|---|---|
| D47 | 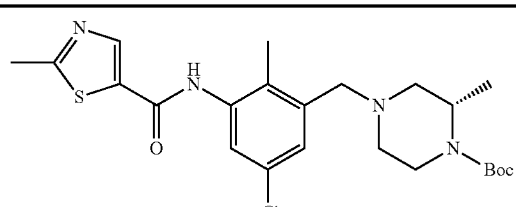 | MS (ESI): $C_{23}H_{31}ClN_4O_3S$ requires 478; found 479 $[M + H]^+$. |
| D48 | | MS (ESI): $C_{26}H_{32}ClN_5O_3$ requires 497; found 498 $[M + H]^+$. | late, trifluoroacetic acid salt (D39, 4.2 g) in DCM (60 mL) was added TFA (20.81 mL) at RT with stirring. The resulting mixture was heated under reflux overnight. The mixture was cooled to RT and quenched with sat. $Na_2CO_3$ solution carefully. The pH was adjusted to around 10. The aqueous phase was separated and extracted for five times with THF/EA. The combined organic phases were concentrated in vacuo to a volume of approximately 100 mL. The solution was then dried over $Na_2SO_4$, filtered and concentrated to afford the title compound (2.8 g). MS (ESI): $C_{21}H_{23}FN_4O$ requires 366; found 367 $[M+H]^+$.

Description 51

(S)—N-(5-chloro-2-methyl-3-((3-methylpiperazin-1-yl)methyl)phenyl)-6-methylnicotinamide, 2 hydrochloride acid salt (D51)

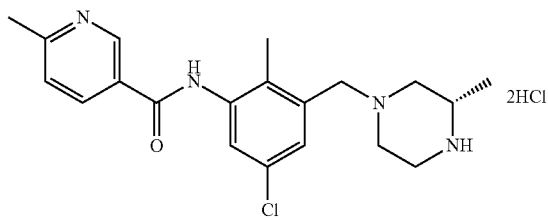

A mixture of (S)-tert-butyl 4-(5-chloro-2-methyl-3-(6-methylnicotinamido)benzyl)-2-methylpiperazine-1-carboxylate (D36, 1.0 g) in DCM (6 mL) was added HCl solution (4 M in dioxane, 1.057 mL). The mixture was stirred at RT for 2 hours, and then concentrated under reduced pressure to give the title compound (1.07 g) as a light yellow solid. MS (ESI): $C_{20}H_{25}ClN_4O$ requires 372; found 373 $[M+H]^+$.

Description 52

(S)—N-(5-chloro-2-methyl-3-((3-methylpiperazin-1-yl)methyl)phenyl)-3-cyanobenzamide (D52)

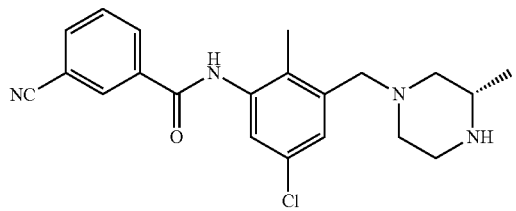 [SMILES: Cc1c(CN2CCN[C@@H](C)C2)cc(Cl)cc1NC(=O)c1cccc(C#N)c1]

To a solution of (S)-tert-butyl 4-(5-chloro-3-(3-cyanobenzamido)-2-methylbenzyl)-2-methylpiperazine-1-carboxylate (D34, 5.99 g) in DCM (20 mL) was added TFA (9.55 mL) dropwise at RT. The mixture was heated at 40° C. for 2 hours. The solvent was removed under vacuum. The residue was neutralized with sat. $Na_2CO_3$ solution to pH=10, and then extracted with DCM (2×50 mL). The combined organic layers were dried over $Na_2SO_4$, filtered and concentrated to afford the title compound (4.89 g) as a pale yellow solid. MS (ESI): $C_{21}H_{23}ClN_4O$ requires: 382; found 383 $[M+H]^+$.

Description 53-54

Descriptions 53 and 54 were prepared using a similar procedure to that described for Description 52.
D53: (S)—N-(5-chloro-2-methyl-3-((3-methylpiperazin-1-yl)methyl)phenyl)-3-cyano-4-fluorobenzamide
D54: (S)—N-(5-chloro-2-methyl-3-((3-methylpiperazin-1-yl)methyl)phenyl)-3-cyano-4-methylbenzamide

| | Structure | Characterization |
|---|---|---|
| D53 | 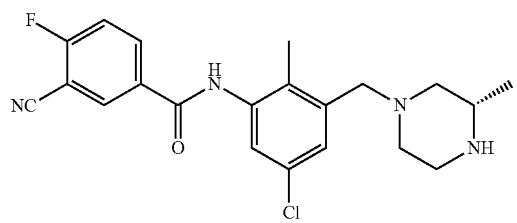 | MS (ESI): $C_{21}H_{22}ClFN_4O$ requires 400; found 401 $[M + H]^+$. |
| D54 | 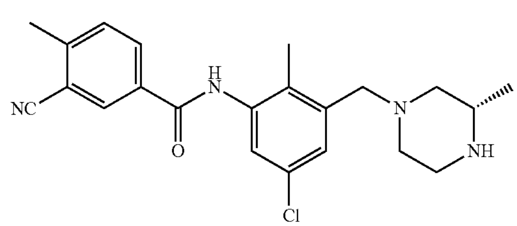 | MS (ESI): $C_{22}H_{25}ClN_4O$ requires 396; found 397 $[M + H]^+$. |

Description 55

(S)—N-(5-chloro-2-methyl-3-((3-methylpiperazin-1-yl)methyl)phenyl)-5-fluoro-6-methylnicotinamide (D55)

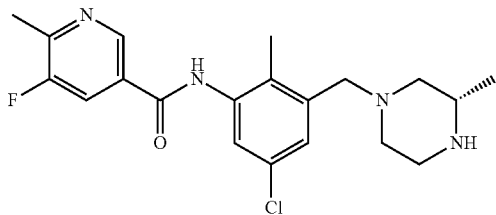 [SMILES: Cc1ncc(C(=O)Nc2cc(Cl)cc(CN3CCN[C@@H](C)C3)c2C)cc1F]

To a solution of (S)-tert-butyl 4-(5-chloro-3-(5-fluoro-6-methylnicotinamido)-2-methylbenzyl)-2-methylpiperazine-1-carboxylate (D40, 900 mg) in DCM (10 mL), TFA (1.130 mL) was added dropwise, the reaction mixture was stirred overweekend at room temperature. LCMS showed reaction completed. Neutralized with saturated $Na_2CO_3$ solution to pH=10, extracted, the aqueous layer was extracted with DCM twice (10 mL×2). Combined organic layer was dried over $Na_2SO_4$. Filtered, the filtrate was concentrated to dryness, giving the title compound (686.9 mg) as yellow solid (95% purity). $^1$H NMR (400 MHz, $CDCl_3$) δ ppm 1.01 (d, 3H), 1.71 (t, 1H), 2.04 (td, 1H), 2.27 (s, 3H), 2.62 (d, 3H), 2.70 (d, 2H), 2.76-2.84 (m, 1H), 2.87 (d, 1H), 2.95 (d, 1H), 3.33-3.50 (m, 2H), 7.18 (s, 1H), 7.72 (brs, 1H), 7.81 (brs, 1H), 7.87 (d, 1H), 8.77 (s, 1H). $^{19}$F NMR (376 MHz, $CDCl_3$) δ ppm −122.7. MS (ESI): $C_{20}H_{24}ClFN_4O$ requires 390; found 391 $[M+H]^+$.

Description 57

(S)—N-(5-chloro-2-methyl-3-((3-methylpiperazin-1-yl)methyl)phenyl)-5-cyano-6-methylnicotinamide (D57)

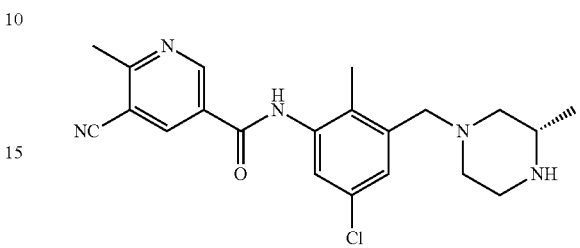

To a solution of (S)-tert-butyl 4-(5-chloro-3-(5-cyano-6-methylnicotinamido)-2-methylbenzyl)-2-methylpiperazine-1-carboxylate (D42, 3.08 g) in DCM (12 mL), TFA (4.29 mL) was added dropwise at room temperature. The reaction mixture was stirred overnight, LCMS showed reaction completed. Diluted with DCM (20 mL), neutralized with saturated $Na_2CO_3$ aqueous solution to pH=10, then 2 M NaOH aqueous solution was added until pH=11. Extracted, the aqueous layer was extracted with DCM again (10 mL). Combined organic layer was dried over $Na_2SO_4$. Filtered, the filtrate was concentrated to dryness, giving the title compound (2.6 g) as a yellow solid (92% purity based on LCMS). MS (ESI): $C_{21}H_{24}ClN_5O$ requires 397; found 398 $[M+H]^+$.

Description 56

Description 56 was prepared using a similar procedure to that described for Description 52.

D56: (S)—N-(5-chloro-2-methyl-3-((3-methylpiperazin-1-yl)methyl)phenyl)-2-cyanoisonicotinamide

Description 58

Description 58 was prepared using a similar procedure to that described for Description 52.

D58: (S)—N-(5-chloro-2-methyl-3-((3-methylpiperazin-1-yl)methyl)phenyl)-6-cyanonicotinamide

| | Structure | Characterization |
|---|---|---|
| D56 | ![D56 structure] | MS (ESI): $C_{20}H_{22}ClN_5O$ requires 383; found 384 $[M+H]^+$. |

| | Structure | Characterization |
|---|---|---|
| D58 | 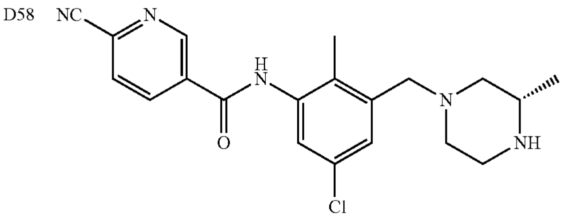 | MS (ESI): $C_{20}H_{22}ClN_5O$ requires 383; found 384 $[M + H]^+$. |

Description 59

(S)—N-(5-chloro-2-methyl-3-((3-methylpiperazin-1-yl)methyl)phenyl)-6-ethylnicotinamide (D59)

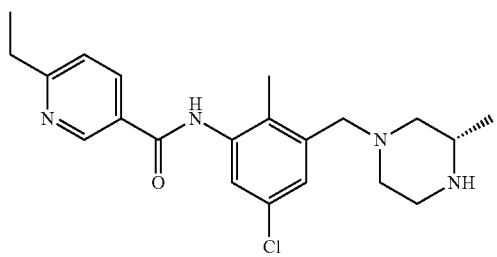 [SMILES: CCc1ccc(C(=O)Nc2cc(Cl)cc(CN3CCN[C@@H](C)C3)c2C)cn1]

A solution of (S)-tert-butyl 4-(5-chloro-3-(6-ethylnicotinamido)-2-methylbenzyl)-2-methylpiperazine-1-carboxylate (D35, 1.6 g) and aqueous HCl solution (4 M, 3.29 mL) in DCM (10 mL) was stirred 1 hour. Cold water (30 mL) was added. The resulting mixture was neutralized with sat. NaHCO₃ solution. The aqueous layer was extracted with DCM (2×100 mL). The combined organic layers were dried over Na₂SO₄, filtered and concentrated in vacuo to give the title compound (1.0 g) as a light yellow solid. MS (ESI): $C_{21}H_{27}ClN_4O$ requires 386; found no mass.

Description 60

(S)—N-(5-chloro-2-methyl-3-((3-methylpiperazin-1-yl)methyl)phenyl)-3-cyano-5-fluorobenzamide, 2 hydrochloric acid salt (D60)

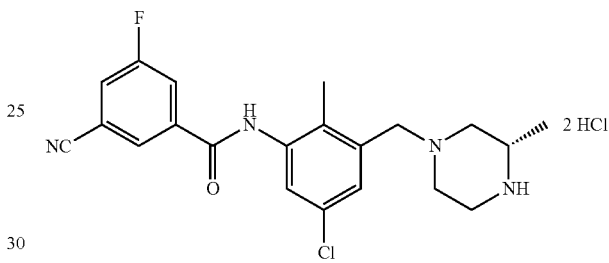

To a solution of (S)-tert-butyl 4-(5-chloro-3-(3-cyano-5-fluorobenzamido)-2-methylbenzyl)-2-methylpiperazine-1-carboxylate (D46, 320 mg) in methanol (20 mL) added HCl (46.6 mg). After stirring at 60° C. for 5 hours, the mixture was concentrated to give the title compound (250 mg) as a white solid. MS (ESI): $C_{21}H_{22}ClFN_4O$ requires 400; found 401 $[M+H]^+$.

Description 61-64

Descriptions 61 to 64 were prepared using a similar procedure to that described for Description 60.

D61: (S)—N-(5-chloro-2-methyl-3-((3-methylpiperazin-1-yl)methyl)phenyl)-2-methylthiazole-5-carboxamide, 2 hydrochloric acid salt D62: (S)—N-(5-chloro-2-methyl-3-((3-methylpiperazin-1-yl)methyl)phenyl)-6-cyano-5-fluoronicotinamide, 2 hydrochloric acid salt D63: (S)—N-(5-chloro-2-methyl-3-((3-methylpiperazin-1-yl)methyl)phenyl)-6-cyano-5-methylnicotinamide, 2 hydrochloric acid salt D64: (S)-5-chloro-N-(5-cyano-2-methyl-3-((3-methylpiperazin-1-yl)methyl)phenyl)-6-methylnicotinamide, 2 hydrochloric acid salt

| | Structure | Characterization |
|---|---|---|
| D61 | 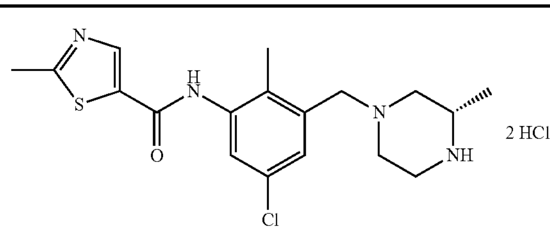 | MS (ESI): $C_{18}H_{23}ClN_4OS$ requires 378; found 379 $[M + H]^+$. |

| | Structure | Characterization |
|---|---|---|
| D62 | 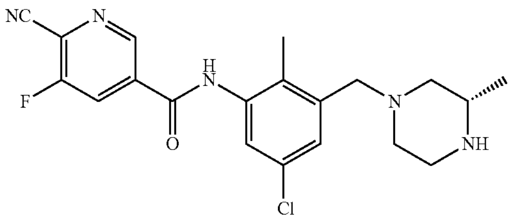 | MS (ESI): $C_{20}H_{21}ClFN_5O$ requires 401; found 402 $[M + H]^+$. |
| D63 | 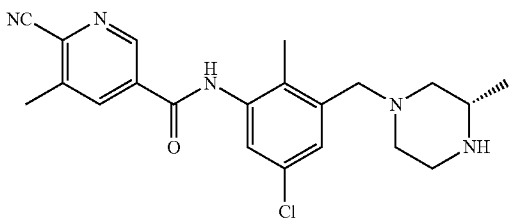 | MS (ESI): $C_{21}H_{24}ClN_5O$ requires 397; found 398 $[M + H]^+$. |
| D64 | 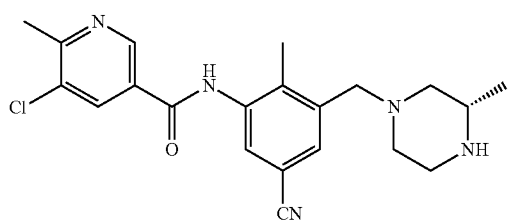 | MS (ESI): $C_{21}H_{24}ClN_5O$ requires 397; found 398 $[M + H]^+$. |

Description 65

(S)—N-(5-chloro-2-methyl-3-((3-methylpiperazin-1-yl)methyl)phenyl)-5-fluoronicotinamide, 2 hydrochloric acid salt (D65)

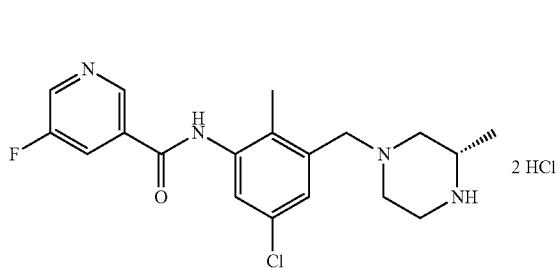 [SMILES: Cc1c(CN2CCN[C@@H](C)C2)cc(Cl)cc1NC(=O)c1cncc(F)c1]

To a mixture of (S)-tert-butyl 4-(5-chloro-3-(5-fluoronicotinamido)-2-methylbenzyl)-2-methylpiperazine-1-carboxylate (D45, 300 mg) and HCl (2293 mg) in 1,4-dioxane (6 mL) was stirred for 2 hours. The mixture was concentrated to give the title compound (210 mg). MS (ESI): $C_{19}H_{22}ClFN_4O$ requires 376; found 377 $[M+H]^+$.

Description 66

(S)-(4-(5-chloro-2-methyl-3-nitrobenzyl)-2-methyl-piperazin-1-yl)(tetrahydro-2H-pyran-4-yl)methanone (D66)

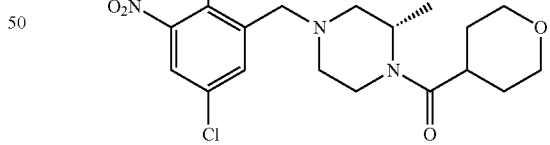

To a solution of tetrahydro-2H-pyran-4-carboxylic acid (484 mg) in DCM (20 mL) were added DMAP (46.0 mg) and EDC (1307 mg). After stirring for 20 mins, a solution of (S)-1-(5-chloro-2-methyl-3-nitrobenzyl)-3-methylpiperazine (D32, 960 mg) in DCM (5 mL) was added. The resulting mixture was stirred overnight, and washed with water (2×15 mL). The organic layer was dried over $Na_2SO_4$, filtered and concentrated under vacuum to give the title compound (1.43 g). MS (ESI): $C_{19}H_{26}ClN_3O_4$, requires 395; found 396 $[M+H]^+$.

Description 67

((S)-4-(5-chloro-2-methyl-3-nitrobenzyl)-2-methyl-piperazin-1-yl)((R)-tetrahydrofuran-2-yl)methanone (D67)

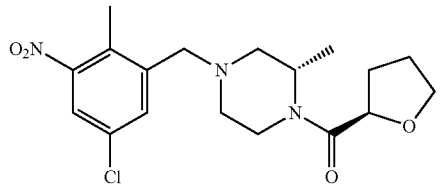 [SMILES: Cc1c(CN2CCN(C(=O)[C@H]3CCCO3)[C@@H](C)C2)cc(Cl)cc1[N+](=O)[O-]]

To a mixture of (R)-tetrahydrofuran-2-carboxylic acid (364 mg), DIPEA (1215 mg), and HATU (1783 mg) in DMF (15 mL) was added (S)-1-(5-chloro-2-methyl-3-nitrobenzyl)-3-methylpiperazine (D32, 890 mg). The mixture was stirred at 25° C. for 6 hours. The resulting mixture was diluted with water (70 mL), and extracted with EA (3×40 mL). The combined organic layers were washed with water (3×50 mL) and brine (2×50 mL), dried over sodium sulfate and concentrated. The residue was purified by column chromatography (eluting with PE:EA=3:1) to afford the title compound (1.2 g) as a yellow oil. MS (ESI): $C_{18}H_{24}ClN_3O_4$ requires 381; found 382 [M+H]$^+$.

Description 68-73

Descriptions 68 to 73 were prepared using a similar procedure to that described for Description 67.

D68: ((S)-4-(5-chloro-2-methyl-3-nitrobenzyl)-2-methyl-piperazin-1-yl)((S)-tetrahydrofuran-2-yl)methanone
D69: ((S)-4-(5-chloro-2-methyl-3-nitrobenzyl)-2-methyl-piperazin-1-yl)(tetrahydrofuran-3-yl)methanone
D70: ((S)-4-(5-fluoro-2-methyl-3-nitrobenzyl)-2-methyl-piperazin-1-yl)((R)-tetrahydrofuran-2-yl)methanone
D71: ((S)-4-(5-fluoro-2-methyl-3-nitrobenzyl)-2-methyl-piperazin-1-yl)((S)-tetrahydrofuran-2-yl)methanone
D72: ((S)-4-(5-chloro-2-methyl-3-nitrobenzyl)-2-ethylpiperazin-1-yl)((R)-tetrahydrofuran-2-yl)methanone
D73: ((S)-4-(5-fluoro-2-methyl-3-nitrobenzyl)-2-methyl-piperazin-1-yl)(tetrahydrofuran-3-yl)methanone

| | Structure | Characterization |
|---|---|---|
| D68 | 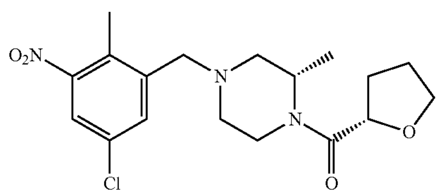 [SMILES: Cc1c(CN2CCN(C(=O)[C@@H]3CCCO3)[C@@H](C)C2)cc(Cl)cc1[N+](=O)[O-]] | MS (ESI): $C_{18}H_{24}ClN_3O_4$ requires 381; found 382 [M + H]$^+$. |
| D69 | 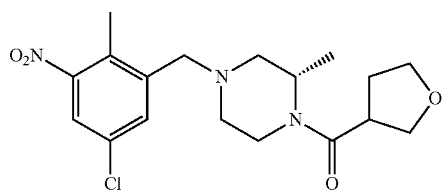 [SMILES: Cc1c(CN2CCN(C(=O)C3CCOC3)[C@@H](C)C2)cc(Cl)cc1[N+](=O)[O-]] | MS (ESI): $C_{18}H_{24}ClN_3O_4$ requires 381; found 382 [M + H]$^+$. |
| D70 | 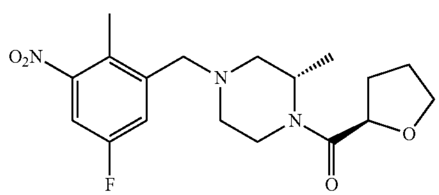 [SMILES: Cc1c(CN2CCN(C(=O)[C@H]3CCCO3)[C@@H](C)C2)cc(F)cc1[N+](=O)[O-]] | MS (ESI): $C_{18}H_{24}FN_3O_4$ requires 365; found 366 [M + H]$^+$. |
| D71 | 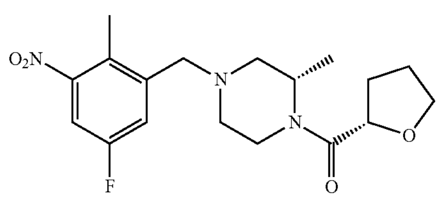 | MS (ESI): $C_{18}H_{24}FN_3O_4$ requires 365; found 366 [M + H]$^+$. |
| D72 | 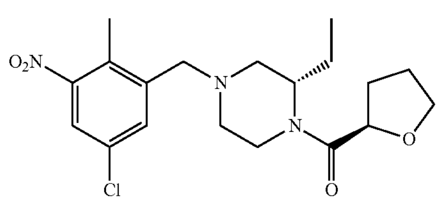 | MS (ESI): $C_{19}H_{26}ClN_3O_4$ requires 395; found 396 [M + H]$^+$ |

| | Structure | Characterization |
|---|---|---|
| D73 | O2N, methyl, F, piperazine-methylpiperazinyl-(tetrahydrofuran-3-yl)methanone structure | MS (ESI): $C_{18}H_{24}FN_3O_4$ requires 365; found 366 $[M + H]^+$. |

Description 74

((S)-4-(3-amino-5-chloro-2-methylbenzyl)-2-methyl-piperazin-1-yl)((S)-tetrahydrofuran-2-yl)methanone (D74)

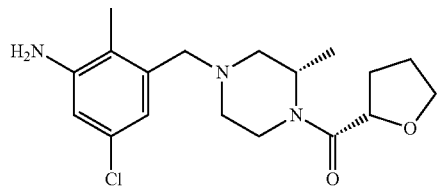

To a mixture of ((S)-4-(5-chloro-2-methyl-3-nitrobenzyl)-2-methylpiperazin-1-yl)((S)-tetrahydrofuran-2-yl)methanone (D68, 1.2 g), iron (0.877 g) in methanol (15 mL) was added a solution of ammonia chloride (0.841 g) in water (3 mL). The mixture was stirred at 70° C. for 1 hour, and then filtered. The filtrate was concentrated, and the residue was dissolved in EA and water. The organic layer was washed with brine, dried over sodium sulfate and concentrated to afford the title compound (800 mg) as a yellow solid. MS (ESI): $C_{18}H_{26}ClN_3O_2$ requires 351; found 352 $[M+H]^+$.

Description 75-80

Descriptions 75 to 80 were prepared using a similar procedure to that described for Description 74.

D75: ((S)-4-(3-amino-5-chloro-2-methylbenzyl)-2-methyl-piperazin-1-yl)((R)-tetrahydrofuran-2-yl)methanone D76: ((S)-4-(3-amino-5-chloro-2-methylbenzyl)-2-methyl-piperazin-1-yl)(tetrahydrofuran-3-yl)methanone D77: ((S)-4-(3-amino-5-fluoro-2-methylbenzyl)-2-methyl-piperazin-1-yl)((R)-tetrahydrofuran-2-yl)methanone D78: ((S)-4-(3-amino-5-fluoro-2-methylbenzyl)-2-methyl-piperazin-1-yl)((S)-tetrahydrofuran-2-yl)methanone D79: ((S)-4-(3-amino-5-chloro-2-methylbenzyl)-2-ethyl-piperazin-1-yl)((R)-tetrahydrofuran-2-yl)methanone D80: ((S)-4-(3-amino-5-fluoro-2-methylbenzyl)-2-methyl-piperazin-1-yl)(tetrahydrofuran-3-yl)methanone

| | Structure | Characterization |
|---|---|---|
| D75 | H2N, methyl, Cl, piperazinyl-(R)-tetrahydrofuran-2-yl methanone | MS (ESI): $C_{18}H_{26}ClN_3O_2$ requires 351; found 352 $[M + H]^+$. |
| D76 | H2N, methyl, Cl, piperazinyl-(tetrahydrofuran-3-yl) methanone | MS (ESI): $C_{18}H_{26}ClN_3O_2$ requires 351; found 352 $[M + H]^+$. |
| D77 | H2N, methyl, F, piperazinyl-(R)-tetrahydrofuran-2-yl methanone | MS (ESI): $C_{18}H_{26}ClN_3O_2$ requires 335; found 336 $[M + H]^+$. |

| | Structure | Characterization |
|---|---|---|
| D78 | 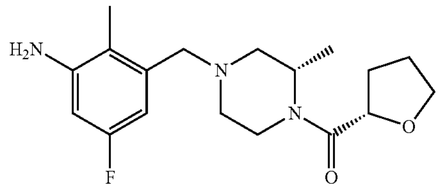 | MS (ESI): $C_{18}H_{26}ClN_3O_2$ requires 335; found 336 $[M + H]^+$. |
| D79 | 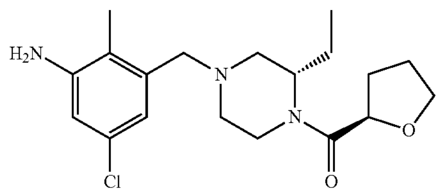 | MS (ESI): $C_{19}H_{28}ClN_3O_2$ requires 365; found 366 $[M + H]^+$. |
| D80 | 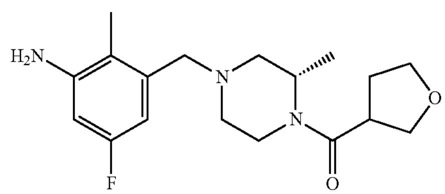 | MS (ESI): $C_{18}H_{26}FN_3O_2$ requires 335; found 336 $[M + H]^+$. |

Description 81

(S)-(4-(3-amino-5-chloro-2-methylbenzyl)-2-methyl-piperazin-1-yl)(tetrahydro-2H-pyran-4-yl)methanone (D81)

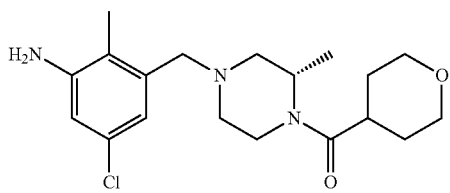

To a solution of (S)-(4-(5-chloro-2-methyl-3-nitroben-zyl)-2-methylpiperazin-1-yl)(tetrahydro-2H-pyran-4-yl)methanone (D66, 1.3 g) in ethanol (20 mL) was added tin(II) chloride dihydrate (3.70 g). The mixture was stirred at RT overnight, and then concentrated. The residue was suspended in DCM (30 mL). Aqueous NaOH solution (2 M) was added until a clear solution formed. The organic phase was separated. The aqueous layer was extracted with DCM (20 mL). The combined organic layers were dried over $Na_2SO_4$, filtered and concentrated to afford the title compound (1.09 g). MS (ESI): $C_{19}H_{28}ClN_3O_2$ requires 365; found 366 $[M+H]^+$.

Description 82

5-methoxy-6-methylnicotinic acid (D82)

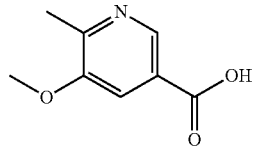

The mixture of 5-fluoro-6-methylnicotinic acid (D17, 3.5 g) and sodium methanolate (12.2 g) in DMF (50 mL) was heated to 140° C. for 16 hours. After cooled to RT, the mixture was filtered and the solid was collected. The solid was dissolved in water (10 mL) and the pH value was adjusted to 3-4 using HCl solution (2 M) at 0° C. The precipitate was collected by filtration, washed with water and dried to afford the title compound (2.45 g) as white solid. MS (ESI): $C_8H_9NO_3$ requires 167; found 168 $[M+H]^+$.

Description 83

(R)-tert-butyl 4-(5-chloro-2-methyl-3-nitrobenzoyl)-2-methylpiperazine-1-carboxylate (D83)

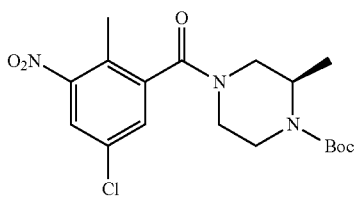 [SMILES: Cc1c(C(=O)N2CCN(C(=O)OC(C)(C)C)[C@H](C)C2)cc(Cl)cc1[N+](=O)[O-]]

The suspension of 5-chloro-2-methyl-3-nitrobenzoic acid (D20, 5 g) in sulfurous dichloride (20 ml) was stirred and heated to reflux for 3 hours. The mixture was concentrated in vacuo and the residue was added to the solution (R)-tert-butyl 2-methylpiperazine-1-carboxylate (4.18 g) and TEA (7.04 g) in DCM (50 mL) cooled with ice-water bath under $N_2$. The reaction was stirred at RT overnight. The reaction mixture was washed with sat. $NaHCO_3$ solution (50 mL) and brine (2×50 mL), then dried over $Na_2SO_4$, After filtration, the solvent was removed in vacuo to afford the title compound (8 g) as white solid.

Description 84

Description 84 was prepared using a similar procedure to that described for Description 27.
D84: (R)-tert-butyl 4-(5-chloro-2-methyl-3-nitrobenzyl)-2-methylpiperazine-1-carboxylate

| Description | Structure | Characterization |
|---|---|---|
| D84 | 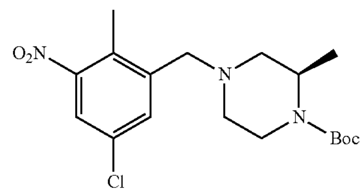 [SMILES: Cc1c(CN2CCN(C(=O)OC(C)(C)C)[C@H](C)C2)cc(Cl)cc1[N+](=O)[O-]] | MS (ESI): $C_{18}H_{26}ClN_3O_4$ requires 383; found 384 $[M + H]^+$. |

Description 85

Description 85 was prepared using a similar procedure to that described for Description 74.
D85: (R)-tert-butyl 4-(3-amino-5-chloro-2-methylbenzyl)-2-methylpiperazine-1-carboxylate

| Description | Structure | Characterization |
|---|---|---|
| D85 | 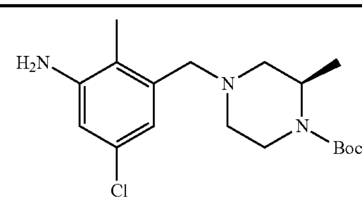 | MS (ESI): $C_{18}H_{28}ClN_3O_2$ requires 353; found 354 $[M + H]^+$. |

Descriptions 86-87

Descriptions 86-87 were prepared using a similar procedure to that described for Description 40, with the specified reaction solvent listed in the table.
D86: (S)-tert-butyl 4-(5-chloro-3-(5,6-dimethylnicotinamido)-2-methylbenzyl)-2-methylpiperazine-1-carboxylate
D87: (R)-tert-butyl 4-(5-chloro-3-(5-fluoro-6-methylnicotinamido)-2-methylbenzyl)-2-methylpiperazine-1-carboxylate

| Description | Structure | Solvent | Characterization |
|---|---|---|---|
| D86 | 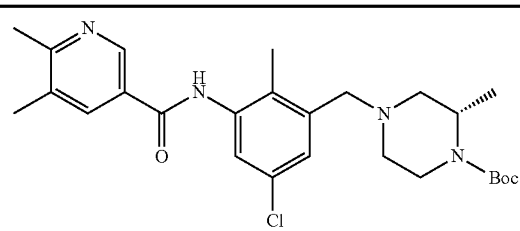 | DCM | MS (ESI): $C_{26}H_{35}ClN_4O_3$ requires 486; found 487 $[M + H]^+$. |

-continued

| Description | Structure | Solvent | Characterization |
|---|---|---|---|
| D87 | 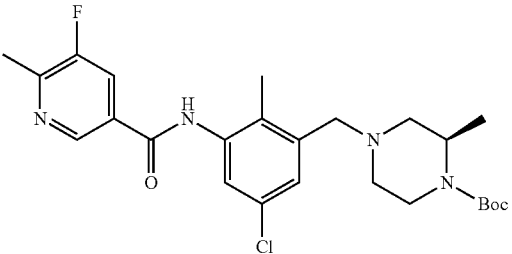 [SMILES: Cc1ncc(C(=O)Nc2cc(Cl)cc(CN3CCN(C(=O)OC(C)(C)C)[C@H](C)C3)c2C)cc1F] | DMF | MS (ESI): $C_{25}H_{32}ClFN_4O_3$ requires 490; found 491 [M + H]+. |

Description 88

Description 88 was prepared using a similar procedure to that described for Description 34.
D88: (S)-tert-butyl 4-(5-chloro-3-(5-methoxy-6-methylnicotinamido)-2-methylbenzyl)-2-methylpiperazine-1-carboxylate

| Description | Structure | Characterization |
|---|---|---|
| D88 | 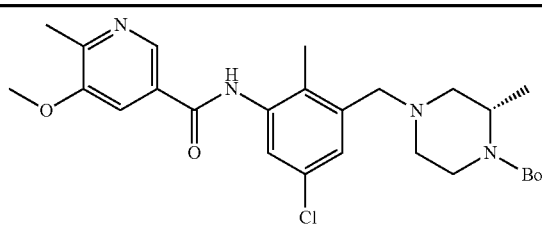 | MS (ESI): $C_{26}H_{35}ClN_4O_4$ requires 502; found 503 [M + H]$^+$. |

Descriptions 89-91

Descriptions 89-91 were prepared using a similar procedure to that described for Description 65.
D89: (S)—N-(5-chloro-2-methyl-3-((3-methylpiperazin-1-yl)methyl)phenyl)-5,6-dimethylnicotinamide, 2 hydrochloride acid salt
D90: (S)—N-(5-chloro-2-methyl-3-((3-methylpiperazin-1-yl)methyl)phenyl)-5-methoxy-6-methylnicotinamide, 2 hydrochloride acid salt
D91: (R)—N-(5-chloro-2-methyl-3-((3-methylpiperazin-1-yl)methyl)phenyl)-5-fluoro-6-methylnicotinamide, 2 hydrochloride acid salt

| Description | Structure | Characterization |
|---|---|---|
| D89 | 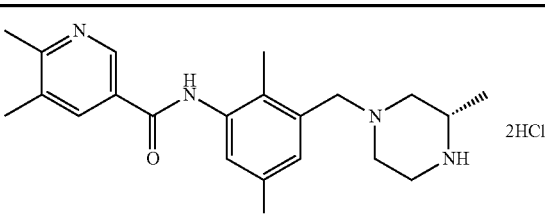 | MS (ESI): $C_{21}H_{27}ClN_4O$ requires 386; found 387 [M + H]$^+$. |
| D90 | 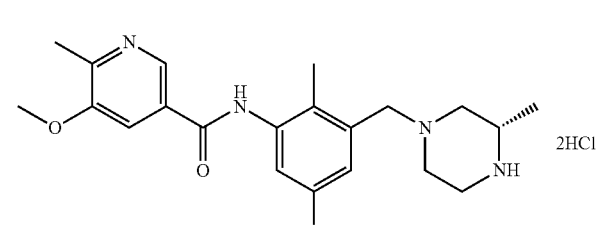 | MS (ESI): $C_{21}H_{27}ClN_4O_2$ requires 402; found 403 [M + H]$^+$. |

| Description | Structure | Characterization |
|---|---|---|
| D91 | 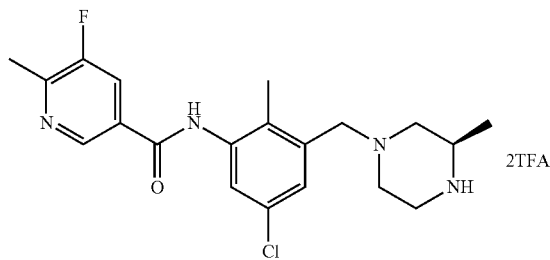 | MS (ESI): $C_{20}H_{24}ClFN_4O$ requires 390; found 391 $[M + H]^+$. |

Description 92

(R)—N-(5-chloro-2-methyl-3-((3-methylpiperazin-1-yl)methyl)phenyl)-5-fluoro-6-methylnicotinamide, 2 Trifluoroacetic acid salt (D92)

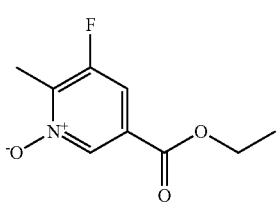

To a solution of (R)-tert-butyl 4-(5-chloro-3-(5-fluoro-6-methylnicotinamido)-2-methylbenzyl)-2-methylpiperazine-1-carboxylate (D87, 814 mg) in DCM (8 mL), trifluoroacetic acid (1.3 ml) was added dropwise at room temperature. The reaction mixture was stirred overnight. Solvent was removed under vacuum, the residue was dissolved with EtOAc (20 mL), neutralized with saturated $Na_2CO_3$ solution to pH=10. Extracted, the aqueous layer was extracted with EtOAc three times (3×10 mL). Combined organic layer was dried over $Na_2SO_4$. Filtered, the filtrate was concentrated to dryness, giving the title compound (950 mg, $^{19}$F NMR showed it was TFA salt). $^1$H NMR (400 MHz, MeOD-$d_4$): 8.87 (s, 1H), 8.07 (d, J=9.8 Hz, 1H), 7.37 (s, 1H), 7.34 (s, 1H), 3.69 (s, 2H), 3.41-3.36 (m, 2H), 3.16 (t, J=12.0 Hz, 1H), 3.03 (t, J=12.8 Hz, 2H), 2.60 (s, 3H), 2.47 (t, J=12.3 Hz, 1H), 2.32-2.22 (m, 4H), 1.31 (d, J=6.6 Hz, 3H). $^{19}$F NMR (376 MHz, MeOD-$d_4$): −77.3, −125.3. MS (ESI): $C_{20}H_{24}ClFN_4O$ requires 390; found 391 $[M+H]^+$.

Description 93

5-(ethoxycarbonyl)-3-fluoro-2-methylpyridine 1-oxide (D93)

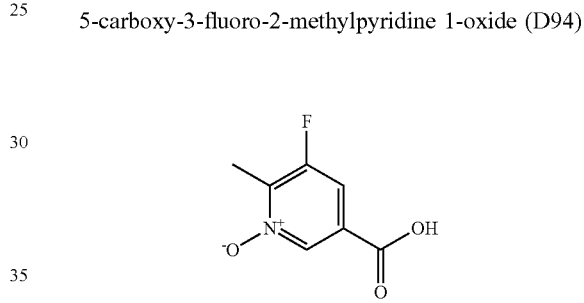

To a solution of ethyl 5-fluoro-6-methylnicotinate (prepared using a similar procedure to that described for D16, 200 mg) in DCM (5 mL) was added 3-chlorobenzoperoxoic acid (226 mg) at 25° C. overnight. The reaction mixture was concentrated and the residue purified by flash silica gel chromatography (PE/EA=1/1) to provide the title compound (200 mg) as a white solid. MS (ESI): $C_9H_{10}FNO_3$ requires 199; found 200 $[M+H]^+$.

Description 94

5-carboxy-3-fluoro-2-methylpyridine 1-oxide (D94)

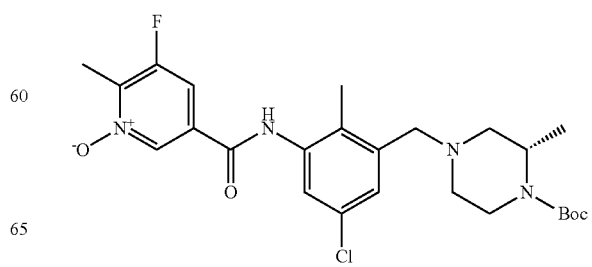

To a solution of 5-(ethoxycarbonyl)-3-fluoro-2-methylpyridine 1-oxide (D93, 200 mg) in THF (2 mL) was added water (2.000 mL) and lithium hydroxide (72.1 mg) at 25° C., after the completion of addition, the reaction mixture was stirred at 25° C. for 1 h. The organic solvent was removed in vacuo, the aqueous layer was acidified to pH ~3 with hydrogen chloride (aq. 1M) and extracted with ethyl acetate (30 mL), the organic phase was dried over anhydrous sodium sulfate and concentrated to give the title compound (170 mg) as a white solid. MS (ESI): $C_7H_6FNO_3$ requires 171; found 172 $[M+H]^+$.

Description 95

(S)-5-((3-((4-(tert-butoxycarbonyl)-3-methylpiperazin-1-yl)methyl)-5-chloro-2-methylphenyl)carbamoyl)-3-fluoro-2-methylpyridine 1-oxide (D95)

To a solution of 5-carboxy-3-fluoro-2-methylpyridine 1-oxide (D94, 170 mg) in DMF (5 mL) was added HATU (378 mg), DIPEA (0.174 mL) and (S)-tert-butyl 4-(3-amino-5-chloro-2-methylbenzyl)-2-methylpiperazine-1-carboxylate (D30, 352 mg) at 25° C., the reaction mixture was stirred at 25° C. overnight. The solvent was evaporated under reduced pressure and the residue was dissolved in dichloromethane. The organic layer was washed with water, brine and dried over sodium sulphate. The solvent was concentrated and the residue was purified by column chromatography on silica gel (petroleum ether/ethyl acetate=2/1) to give the title compound (300 mg) as a yellow solid. MS (ESI): $C_{25}H_{32}ClFN_4O_4$ requires 506; found 507 $[M+H]^+$.

Description 96

(S)-5-((5-chloro-2-methyl-3-((3-methylpiperazin-1-yl)methyl)phenyl)carbamoyl)-3-fluoro-2-methylpyridine 1-oxide, 2 Hydrochloride (D96)

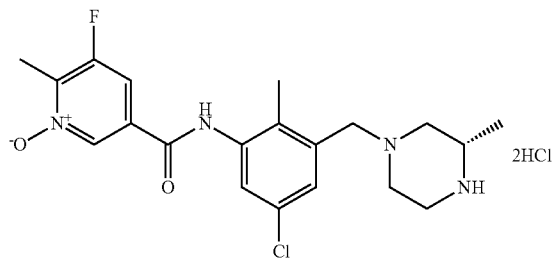

To a solution of (S)-5-((3-((4-(tert-butoxycarbonyl)-3-methylpiperazin-1-yl)methyl)-5-chloro-2-methylphenyl)carbamoyl)-3-fluoro-2-methylpyridine 1-oxide (D95, 300 mg) in 1,4-dioxane (10 mL) was added hydrogen chloride (108 mg), then the reaction mixture was stirred at 25° C. for 1 h and then filtered to give the title compound (280 mg) as a yellow solid. MS (ESI): $C_{20}H_{24}ClFN_4O_2$ requires 406; found 407 $[M+H]^+$.

Example 1

(S)—N-(5-chloro-2-methyl-3-((3-methyl-4-(tetrahydro-2H-pyran-4-carbonyl)piperazin-1-yl)methyl)phenyl)-3-cyanobenzamide (E1)

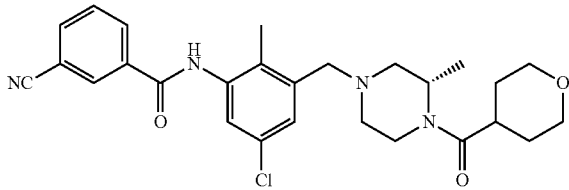

To a solution of tetrahydro-2H-pyran-4-carboxylic acid (1.896 g) in DCM (20 mL) was added 3 drops of DMF, and then oxalyl chloride (1.403 mL) solution in DCM (5 mL) dropwise under a nitrogen atmosphere. The reaction mixture was stirred for 2 hours at RT. The solvent was removed in vacuo. The residue was dissolved in acetonitrile (10 mL). The resulting mixture was added dropwise into a mixture of (S)—N-(5-chloro-2-methyl-3-((3-methylpiperazin-1-yl)methyl)phenyl)-3-cyanobenzamide (D52, 4.65 g) and potassium carbonate (5.04 g) in acetonitrile (30 mL) at 0° C. After addition, the reaction mixture was stirred at RT overnight. After filtration, the filtrate was concentrated to dryness. The residue was dissolved in DCM (40 mL), and washed with sat. $Na_2CO_3$ solution. The organic layer was dried over $Na_2SO_4$, filtered and concentrated. The residue was purified by column chromatography (eluting with DCM/MeOH, MeOH %=0.5-2%) to give the crude product (5.2 g) as a white solid, which was purified again with column chromatography, and then reverse phase chromatography. Pure fractions were collected and freeze-dried to give the TFA salt of the title compound, which was dissolved with DCM (30 mL), washed with NaOH solution (0.6 g in 40 mL water) and water (20 mL). The organic layer was concentrated to dryness. The residue was dissolved in acetonitrile/water and freeze-dried again to give the title compound (1.9 g) as a white solid. $^1$H NMR (400 MHz, MeOD-$d_4$): 8.32 (s, 1H), 8.25 (d, J=7.6 Hz, 1H), 7.94 (d, J=7.6 Hz, 1H), 7.71 (t, J=7.8 Hz, 1H), 7.36 (brs, 1H), 7.29 (brs, 1H), 4.74-4.59 (m, 0.5H), 4.38-4.19 (m, 1H), 4.00-3.88 (m, 2H), 3.88-3.75 (m, 0.5H), 3.61-3.34 (m, 4.5H), 3.02-2.63 (m, 3.5H), 2.30 (s, 3H), 2.24-1.93 (m, 2H), 1.91-1.49 (m, 4H), 1.42-1.14 (m, 3H). MS (ESI): $C_{27}H_{31}ClN_4O_3$ requires 494; found 495 $[M+H]^+$.

Example 2

3-cyano-N-(5-fluoro-2-methyl-3-(((S)-3-methyl-4-((R)-tetrahydrofuran-2-carbonyl)piperazin-1-yl)methyl)phenyl)benzamide, trifluoroacetic acid salt (E2)

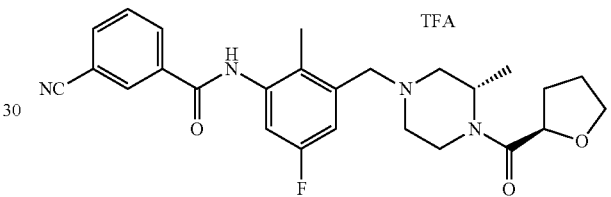

To a solution of (S)-3-cyano-N-(5-fluoro-2-methyl-3-((3-methylpiperazin-1-yl)methyl)phenyl)benzamide (D50, 109.7 mg) and (R)-tetrahydrofuran-2-carboxylic acid (40.9 mg) in DCM (5 mL) was added EDC (116.4 mg) and HOBt (60.7 mg). The reaction mixture was stirred at RT overnight. The mixture was diluted with DCM (10 mL) and washed with water (10 mL). The organic layer was concentrated to dryness and the residue was purified by MDAP (acidic condition) to give the title compound (65.9 mg) as a white solid. $^1$H NMR (400 MHz, MeOD-$d_4$): 8.34 (s, 1H), 8.28 (d, J=7.8 Hz, 1H), 7.99 (d, J=7.6 Hz, 1H), 7.75 (t, J=7.8 Hz, 1H), 7.40-7.32 (m, 2H), 4.77-4.55 (m, 2H), 4.47 (brs, 2H), 4.26 (d, J=13.7 Hz, 0.5H), 3.98-3.79 (m, 2H), 3.66-3.39 (m, 2.5H), 3.29-2.97 (m, 3H), 2.34 (s, 3H), 2.25-2.05 (m, 2H), 2.00-1.90 (m, 2H), 1.54-1.24 (m, 3H). $^{19}$F NMR (376 MHz, MeOD-$d_4$): −76.6, −116.0. MS (ESI): $C_{26}H_{29}FN_4O_3$ requires 464; found 465 $[M+H]^+$.

Example 3

3-cyano-N-(5-fluoro-2-methyl-3-(((S)-3-methyl-4-((S)-tetrahydrofuran-2-carbonyl)piperazin-1-yl)methyl)phenyl)benzamide, trifluoroacetic acid salt (E3)

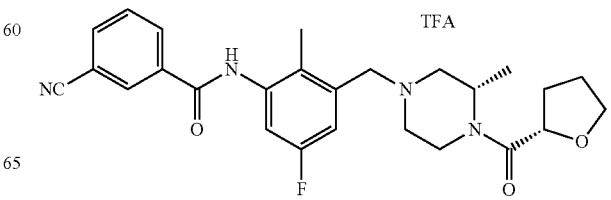

Example 3 was prepared using a similar procedure to that described for Example 2. $^1$H NMR (400 MHz, MeOD-d$_4$): 8.34 (s, 1H), 8.28 (d, J=8.1 Hz, 1H), 7.99 (d, J=7.8 Hz, 1H), 7.75 (t, J=7.8 Hz, 1H), 7.40-7.31 (m, 2H), 4.82-4.75 (m, 0.5H), 4.70 (t, J=6.7 Hz, 1H), 4.61 (brs, 0.5H), 4.52-4.39 (m, 2H), 4.32-4.15 (m, 0.5H), 3.95-3.80 (m, 2H), 3.61 (brs, 0.5H), 3.55-3.40 (m, 2H), 3.28-3.00 (m, 3H), 2.33 (s, 3H), 2.23-2.07 (m, 2H), 2.02-1.89 (m, 2H), 1.54-1.25 (m, 3H). $^{19}$F NMR (376 MHz, MeOD-d$_4$): −76.6, −116.1. MS (ESI): C$_{26}$H$_{29}$FN$_4$O$_3$ requires 464; found 465 [M+H]$^+$.

Example 4

(S)-3-cyano-N-(5-fluoro-2-methyl-3-((3-methyl-4-(tetrahydro-2H-pyran-4-carbonyl)piperazin-1-yl)methyl)phenyl)benzamide (E4)

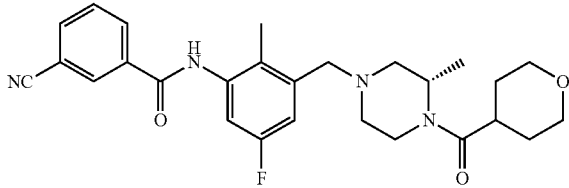 [SMILES: Cc1c(CN2CCN(C(=O)C3CCOCC3)[C@@H](C)C2)cc(Cl)cc1NC(=O)c1cccc(C#N)c1]

To a mixture of (S)-3-cyano-N-(5-fluoro-2-methyl-3-((3-methylpiperazin-1-yl)methyl)phenyl)benzamide (D50, 240 mg) in DMF (5 mL) was added HATU (374 mg) at RT. The mixture was stirred for 10 mins at 25° C., and then DIPEA (169 mg) was added. The mixture was stirred at 25° C. overnight. After cooling, the mixture was extracted with EA. The organic phase was dried over Na$_2$SO$_4$, filtered through a thin pad of celite and concentrated to give a brown oil, which was purified by column chromatography (eluting with PE:EA=10:1) to afford a colorless oil, which was purified by reverse phase chromatography (C18, mobile phase 0.01% NH$_4$HCO$_3$:H$_2$O, CH$_3$CN, 10~95%, 9.5 min, 30 mL/min) to give a pale yellow solid (250 mg), which was purified by preparative HPLC (Gilson GX-281, mobile phase: 0.01% NH$_4$HCO$_3$:H$_2$O, CH$_3$CN, 50~95%, 9.0 min, 30 mL/min) to give the title compound (110 mg) as a white solid. $^1$H NMR (400 MHz, CDCl$_3$): 8.20 (s, 1H), 8.16 (d, J=7.8 Hz, 1H), 7.94-7.82 (m, 2H), 7.68 (t, J=7.8 Hz, 1H), 7.62 (d, J=8.5 Hz, 1H), 6.95 (d, J=6.5 Hz, 1H), 4.76 (brs, 0.5H), 4.38 (d, J=13.3 Hz, 0.5H), 4.11-3.96 (m, 2.5H), 3.63 (d, J=12.0 Hz, 0.5H), 3.53-3.33 (m, 4.5H), 2.98-2.87 (m, 0.5H), 2.84-2.75 (m, 1H), 2.75-2.62 (m, 2H), 2.31 (s, 3H), 2.25-2.15 (m, 1H), 2.09-1.79 (m, 3H), 1.70-1.52 (m, 2H), 1.42-1.18 (m, 3H). MS (ESI): C$_{27}$H$_{31}$FN$_4$O$_3$ requires 478; found 479 [M+H]$^+$.

Example 5-21

Examples 5 to 21 were prepared using a similar procedure to that described for Example 4, with the specified reaction base or solvent listed in the table.

E5: 3-cyano-N-(5-fluoro-2-methyl-3-(((3S)-3-methyl-4-(tetrahydrofuran-2-carbonyl)piperazin-1-yl)methyl)phenyl)benzamide E6: 3-cyano-N-(5-fluoro-2-methyl-3-(((3S)-3-methyl-4-(tetrahydrofuran-3-carbonyl)piperazin-1-yl)methyl)phenyl)benzamide E7: N-(5-chloro-2-methyl-3-(((3S)-3-methyl-4-(tetrahydrofuran-2-carbonyl)piperazin-1-yl)methyl)phenyl)-3-cyanobenzamide E8: N-(5-chloro-2-methyl-3-(((3S)-3-methyl-4-(tetrahydrofuran-3-carbonyl)piperazin-1-yl)methyl)phenyl)-3-cyanobenzamide E9: (S)—N-(5-chloro-2-methyl-3-((3-methyl-4-(tetrahydro-2H-pyran-4-carbonyl)piperazin-1-yl)methyl)phenyl)-6-ethylnicotinamide E10: N-(5-chloro-2-methyl-3-(((S)-3-methyl-4-((S)-tetrahydrofuran-2-carbonyl)piperazin-1-yl)methyl)phenyl)-6-ethylnicotinamide E11: N-(5-chloro-2-methyl-3-(((S)-3-methyl-4-((S)-tetrahydrofuran-2-carbonyl)piperazin-1-yl)methyl)phenyl)-3-cyano-4-methylbenzamide E12: N-(5-chloro-2-methyl-3-(((S)-3-methyl-4-((R)-tetrahydrofuran-2-carbonyl)piperazin-1-yl)methyl)phenyl)-3-cyano-4-methylbenzamide E13: (S)—N-(5-chloro-2-methyl-3-((3-methyl-4-(tetrahydro-2H-pyran-4-carbonyl)piperazin-1-yl)methyl)phenyl)-6-methylnicotinamide E14: N-(5-chloro-2-methyl-3-(((S)-3-methyl-4-((R)-tetrahydrofuran-2-carbonyl)piperazin-1-yl)methyl)phenyl)-6-ethylnicotinamide E15: N-(5-chloro-2-methyl-3-(((S)-3-methyl-4-((R)-tetrahydrofuran-2-carbonyl)piperazin-1-yl)methyl)phenyl)-2-cyanoisonicotinamide E16: N-(5-chloro-2-methyl-3-(((S)-3-methyl-4-((S)-tetrahydrofuran-2-carbonyl)piperazin-1-yl)methyl)phenyl)-2-cyanoisonicotinamide E17: (S)—N-(5-chloro-2-methyl-3-((3-methyl-4-(tetrahydro-2H-pyran-4-carbonyl)piperazin-1-yl)methyl)phenyl)-6-cyano-5-methylnicotinamide E18: N-(5-chloro-2-methyl-3-(((S)-3-methyl-4-((R)-tetrahydrofuran-2-carbonyl)piperazin-1-yl)methyl)phenyl)-6-cyano-5-methylnicotinamide E19: N-(5-chloro-2-methyl-3-(((S)-3-methyl-4-((S)-tetrahydrofuran-2-carbonyl)piperazin-1-yl)methyl)phenyl)-6-cyano-5-methylnicotinamide E20: N-(5-chloro-2-methyl-3-(((S)-3-methyl-4-((R)-tetrahydrofuran-2-carbonyl)piperazin-1-yl)methyl)phenyl)-6-cyano-5-fluoronicotinamide E21: N-(5-chloro-2-methyl-3-(((S)-3-methyl-4-((S)-tetrahydrofuran-2-carbonyl)piperazin-1-yl)methyl)phenyl)-6-cyano-5-fluoronicotinamide

| | Structure | Solvent/base | Characterization |
|---|---|---|---|
| E5 | 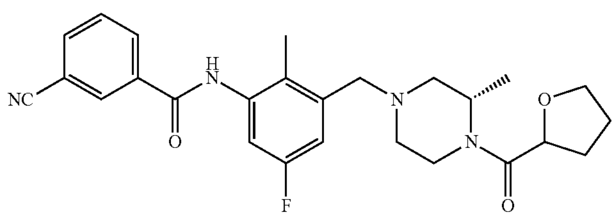 [SMILES: Cc1c(CN2CCN(C(=O)C3CCCO3)[C@@H](C)C2)cc(F)cc1NC(=O)c1cccc(C#N)c1] | DMF/DIPEA | $^1$H NMR (400 MHz, DMSO-d$_6$): 10.18 (s, 1H), 8.41 (s, 1H), 8.27 (d, J = 8.0 Hz, 1H), 8.08 (d, J = 7.8 Hz, 1H), 7.76 (t, J = 7.8 Hz, 1H), 7.18 (dd, J = 9.8 Hz, 2.5 Hz, 1H), 7.09 (dd, J = 9.5 Hz, 2.5 Hz, 1H), 4.68-4.56 (m, 1H), 4.55-4.45 (m, 0.5H), 4.38-4.26 (m, 0.5H), 4.23-4.11 (m, 0.5H), 3.85-3.68 (m, 2.5H), 3.52-3.41 (m, 2H), 3.28-3.13 (m, 0.5H), 2.89-2.71 (m, 1.5H), 2.66 (d, J = 11.0 Hz, 1H), 2.20 (s, 3H), 2.15-1.74 (m, 6H), 1.32-1.08 (m, 3H). MS (ESI): C$_{26}$H$_{29}$FN$_4$O$_3$ requires 464; found 465 [M + H]$^+$. |

| | Structure | Solvent/base | Characterization |
|---|---|---|---|
| E6 | 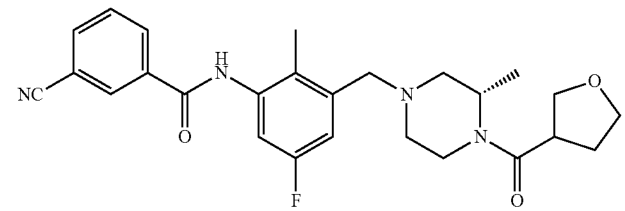 [SMILES: Cc1c(CN2CCN(C(=O)C3CCOC3)[C@@H](C)C2)cc(F)cc1NC(=O)c1cccc(C#N)c1] | DMF/DIPEA | ¹H NMR (400 MHz, DMSO-d$_6$): 10.18 (s, 1H), 8.40 (s, 1H), 8.26 (d, J = 7.8 Hz, 1H), 8.08 (d, J = 7.8 Hz, 1H), 7.76 (t, J = 7.8 Hz, 1H), 7.17 (dd, J = 9.8 Hz, 2.5 Hz, 1H), 7.09 (d, J = 9.3 Hz, 1H), 4.59-4.49 (m, 0.5H), 4.27-4.14 (m, 0.5H), 3.96-3.57 (m, 4.5H), 3.52-3.40 (m, 2H), 3.34-3.14 (m, 2H), 2.87-2.71 (m, 1.5H), 2.65 (d, J = 10.3 Hz, 1H), 2.19 (s, 3H), 2.16-1.83 (m, 4H), 1.30-1.07 (m, 3H). MS (ESI): C$_{26}$H$_{29}$FN$_4$O$_3$ requires 464; found 465 [M + H]⁺ |
| E7 | 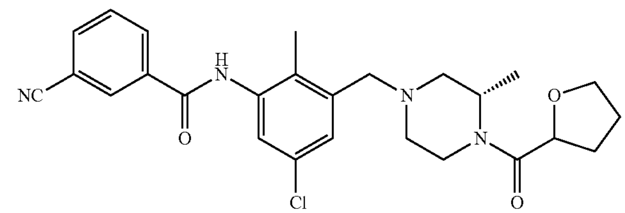 | DMF/DIPEA | ¹H NMR (400 MHz, DMSO-d$_6$): 10.14 (brs, 1H), 8.41 (s, 1H), 8.26 (d, J = 8.0 Hz, 1H), 8.08 (d, J = 7.5 Hz, 1H), 7.82-7.72 (m, 1H), 7.39 (d, J = 2.0 Hz, 1H), 7.31-7.26 (m, 1H), 4.68-4.57 (m, 1H), 4.56-4.46 (m, 0.5H), 4.37-4.28 (m, 0.5H), 4.24-4.12 (m, 0.5H), 3.85-3.69 (m, 2.5H), 3.52-3.43 (m, 2H), 3.28-3.14 (m, 0.5H), 2.87-2.71 (m, 1.5H), 2.64 (d, J = 11.3 Hz, 1H), 2.22 (s, 3H), 2.19-1.75 (m, 6H), 1.32-1.08 (m, 3H). MS (ESI): C$_{26}$H$_{29}$ClN$_4$O$_3$ requires 480; found 481 [M + H]⁺. |
| E8 | 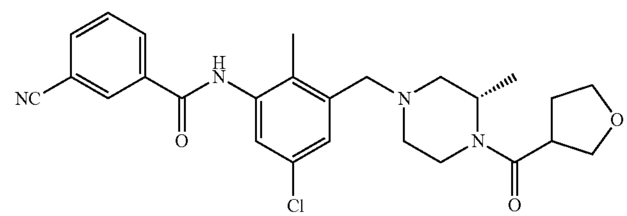 [SMILES: Cc1c(CN2CCN(C(=O)C3CCOC3)[C@@H](C)C2)cc(Cl)cc1NC(=O)c1cccc(C#N)c1] | DMF/DIPEA | ¹H NMR (400 MHz, DMSO-d$_6$): 10.20 (s, 1H), 8.41 (s, 1H), 8.27 (d, J = 8.0 Hz, 1H), 8.08 (d, J = 7.8 Hz, 1H), 7.76 (t, J = 7.8 Hz, 1H), 7.39 (d, J = 1.5 Hz, 1H), 7.28 (brs, 1H), 4.61-4.51 (m, 0.5H), 4.28-4.14 (m, 0.5H), 3.97-3.57 (m, 4.5H), 3.52-3.41 (m, 2H), 3.31-3.14 (m, 2H), 2.87-2.71 (m, 1.5H), 2.65 (d, J = 11.0 Hz, 1H), 2.23 (s, 3H), 2.18-1.86 (m, 4H), 1.31-1.07 (m, 3H). MS (ESI): C$_{26}$H$_{29}$ClN$_4$O$_3$ requires 480; found 481 [M + H]⁺. |
| E9 | 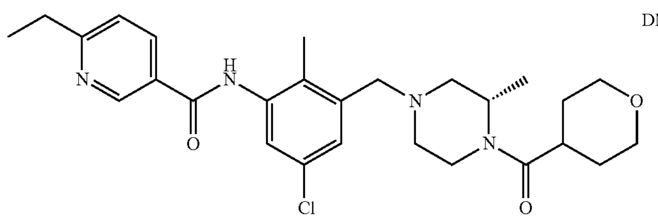 | DMF/DIPEA | ¹H NMR (400 MHz, DMSO-d$_6$): 10.11 (s, 1H), 9.04 (d, J = 1.8 Hz, 1H), 8.22 (dd, J = 8.3 Hz, 2.3 Hz, 1H), 7.44 (d, J = 8.3 Hz, 1H), 7.39 (d, J = 2.0 Hz, 1H), 7.27 (brs, 1H), 4.60-4.51 (m, 0.5H), 4.29-4.14 (m, 1H), 3.88-3.73 (m, 2.5H), 3.53-3.36 (m, 4H), 3.27-3.16 (m, 0.5H), 2.90-2.71 (m, 4.5H), 2.69-2.60 (m, 1H), 2.22 (s, 3H), 2.18-1.84 (m, 2H), 1.73-1.41 (m, 4H), 1.31-1.04 (m, 6H). MS (ESI): C$_{27}$H$_{35}$ClN$_4$O$_3$ requires 498; found 499 [M + H]⁺. |
| E10 | 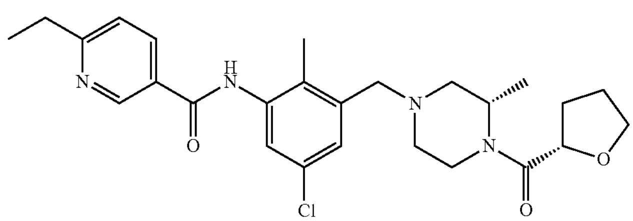 [SMILES: CCc1ccc(C(=O)Nc2cc(Cl)cc(CN3CCN(C(=O)[C@@H]4CCCO4)[C@@H](C)C3)c2C)cn1] | DCM/DIPEA | ¹H NMR (400 MHz, DMSO-d$_6$): 10.11 (s, 1H), 9.04 (d, J = 1.8 Hz, 1H), 8.22 (dd, J = 8.0 Hz, 2.3 Hz, 1H), 7.44 (d, J = 8.0 Hz, 1H), 7.39 (d, J = 2.0 Hz, 1H), 7.27 (d, J = 2.3 Hz, 1H), 4.60 (t, J = 6.5 Hz, 1H), 4.55-4.47 (m, 0.5H), 4.37-4.28 (m, 0.5H), 4.20-4.12 (m, 0.5H), 3.81-3.67 (m, 2.5H), 3.51-3.40 (m, 2H), 3.28-3.16 (m, 0.5H), 2.89-2.79 (m, 2.5H), 2.78-2.69 (m, 1H), 2.69-2.59 (m, 1H), 2.22 (s, 3H), 2.15-1.76 (m, 6H), 1.31-1.06 (m, 6H). MS (ESI): C$_{26}$H$_{33}$ClN$_4$O$_3$ requires 484; found 485 [M + H]⁺. |
| E11 | 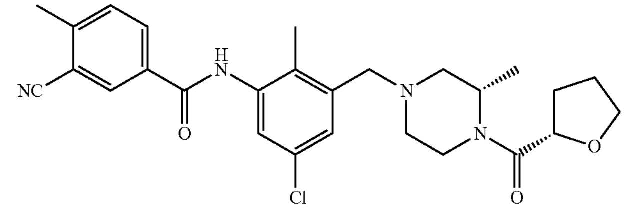 [SMILES: Cc1ccc(C(=O)Nc2cc(Cl)cc(CN3CCN(C(=O)[C@@H]4CCCO4)[C@@H](C)C3)c2C)cc1C#N] | DMF/DIPEA | ¹H NMR (400 MHz, MeOD-d$_4$): 8.26 (s, 1H), 8.14 (dd, J = 8.1 Hz, 1.5 Hz, 1H), 7.59 (d, J = 8.3 Hz, 1H), 7.34 (d, J = 2.0 Hz, 1H), 7.29 (d, J = 2.0 Hz, 1H), 4.77-4.54 (m, 2.5H), 4.38-4.22 (m, 1H), 3.97-3.88 (m, 1H), 3.88-3.80 (m, 1H), 3.76 (d, J = 13.2 Hz, 0.5H), 3.55-3.44 (m, 2H), 3.39 (t, J = 12.0 Hz, 0.5H), 3.00 (t, J = 12.0 Hz, 0.5H), 2.83 (d, J = 11.0 Hz, 1H), 2.71 (d, J = 11.2 Hz, 1H), 2.62 (s, 3H), 2.29 (s, 3H), 2.27-1.86 (m, 6H), 1.40-1.21 (m, 3H). MS (ESI): C$_{27}$H$_{31}$ClN$_4$O$_3$ requires 494; found 495 [M + H]⁺. |

| | Structure | Solvent/base | Characterization |
|---|---|---|---|
| E12 | 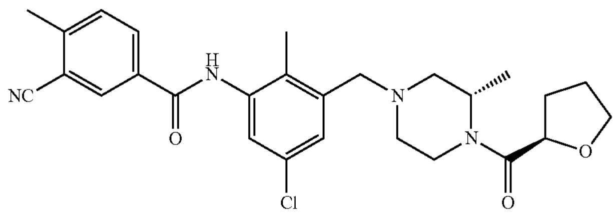 [SMILES: Cc1ccc(C(=O)Nc2cc(Cl)cc(CN3CCN(C(=O)[C@H]4CCCO4)[C@@H](C)C3)c2C)cc1C#N] | DMF/DIPEA | $^1$H NMR (400 MHz, MeOD-d$_4$): 8.26 (d, J = 1.2 Hz, 1H), 8.14 (dd, J = 8.1 Hz, 1.7 Hz, 1H), 7.59 (d, J = 8.3 Hz, 1H), 7.33 (s, 1H), 7.29 (d, J = 2.2 Hz, 1H), 4.75-4.67 (m, 1H), 4.66-4.55 (m, 0.5H), 4.26 (d, J = 13.2 Hz, 0.5H), 4.17 (brs, 0.5H), 4.00-3.90 (m, 1H), 3.88-3.76 (m, 1.5H), 3.56-3.43 (m, 2H), 3.37-3.33 (m, 0.5H), 3.00 (td, J = 12.9 Hz, 3.3 Hz, 0.5H), 2.88-2.77 (m, 1H), 2.72 (dd, J = 11.4 Hz, 5.0 Hz, 1H), 2.62 (s, 3H), 2.29 (s, 3H), 2.27-1.87 (m, 6H), 1.41-1.19 (m, 3H). MS (ESI): C$_{27}$H$_{31}$ClN$_4$O$_3$ requires 494; found 495 [M + H]$^+$. |
| E13 | 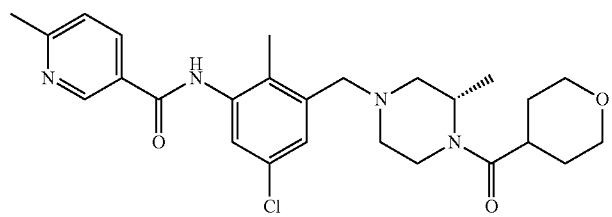 [SMILES: Cc1ccc(C(=O)Nc2cc(Cl)cc(CN3CCN(C(=O)C4CCOCC4)[C@@H](C)C3)c2C)cn1] | DMF/DIPEA | $^1$H NMR (400 MHz, DMSO-d$_6$): 10.11 (s, 1H), 9.02 (d, J = 1.8 Hz, 1H), 8.20 (dd, J = 8.0 Hz, 2.3 Hz, 1H), 7.42 (d, J = 8.3 Hz, 1H), 7.39 (d, J = 2.0 Hz, 1H), 7.27 (brs, 1H), 4.61-4.51 (m, 0.5H), 4.28-4.14 (m, 1H), 3.89-3.73 (m, 2.5H), 3.52-3.34 (m, 4H), 3.27-3.15 (m, 0.5H), 2.88-2.71 (m, 2.5H), 2.70-2.60 (m, 1H), 2.56 (s, 3H), 2.22 (s, 3H), 2.18-1.85 (m, 2H), 1.73-1.40 (m, 4H), 1.30-1.08 (m, 3H). MS (ESI): C$_{26}$H$_{33}$ClN$_4$O$_3$ requires 484; found 485 [M + H]$^+$. |
| E14 | 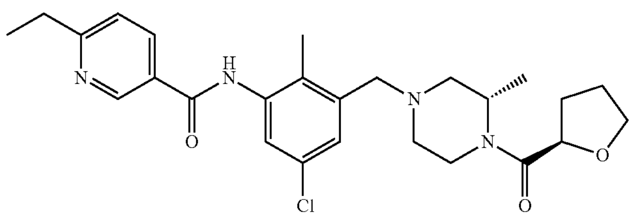 [SMILES: CCc1ccc(C(=O)Nc2cc(Cl)cc(CN3CCN(C(=O)[C@H]4CCCO4)[C@@H](C)C3)c2C)cn1] | DCM/DIPEA | $^1$H NMR (400 MHz, DMSO-d$_6$): 10.12 (s, 1H), 9.04 (d, J = 1.8 Hz, 1H), 8.22 (dd, J = 8.0 Hz, 2.3 Hz, 1H), 7.43 (d, J = 8.0 Hz, 1H), 7.38 (d, J = 1.3 Hz, 1H), 7.29-7.25 (m, 1H), 4.67-4.58 (m, 1H), 4.55-4.44 (m, 0.5H), 4.27-4.11 (m, 1H), 3.85-3.70 (m, 2.5H), 3.52-3.40 (m, 2.5H), 3.27-3.12 (m, 0.5H), 2.87-2.80 (m, 2H), 2.78-2.69 (m, 1H), 2.63 (d, J = 11.0 Hz, 1H), 2.21 (s, 3H), 2.17-1.75 (m, 6H), 1.35-1.07 (m, 6H). MS (ESI): C$_{26}$H$_{33}$ClN$_4$O$_3$ requires 484; found 485 [M + H]$^+$. |
| E15 | 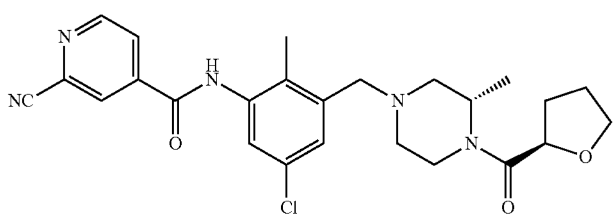 [SMILES: Cc1c(CN2CCN(C(=O)[C@H]3CCCO3)[C@@H](C)C2)cc(Cl)cc1NC(=O)c1ccnc(C#N)c1] | DMF/DIPEA | $^1$H NMR (400 MHz, MeOD-d$_4$): 8.91 (d, J = 4.9 Hz, 1H), 8.36 (s, 1H), 8.14 (d, J = 4.6 Hz, 1H), 7.39 (s, 1H), 7.32 (s, 1H), 4.70 (brs, 1H), 4.63 (brs, 0.5H), 4.27 (d, J = 13.2 Hz, 0.5H), 4.18 (brs, 0.5H), 4.01-3.90 (m, 1H), 3.89-3.76 (m, 1.5H), 3.57-3.44 (m, 2H), 3.39-3.33 (m, 0.5H), 3.00 (t, J = 11.6 Hz, 0.5H), 2.89-2.78 (m, 1H), 2.72 (d, J = 10.5 Hz, 1H), 2.31 (s, 3H), 2.27-1.85 (m, 6H), 1.42-1.17 (m, 3H). MS (ESI): C$_{25}$H$_{28}$ClN$_5$O$_3$ requires 481; found 482 [M + H]$^+$. |
| E16 | 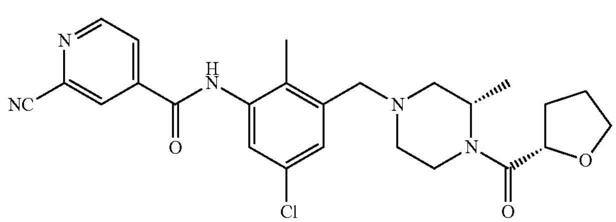 [SMILES: Cc1c(CN2CCN(C(=O)[C@@H]3CCCO3)[C@@H](C)C2)cc(Cl)cc1NC(=O)c1ccnc(C#N)c1] | DMF/DIPEA | $^1$H NMR (400 MHz, MeOD-d$_4$): 8.91 (d, J = 4.9 Hz, 1H), 8.36 (s, 1H), 8.14 (d, J = 4.4 Hz, 1H), 7.39 (s, 1H), 7.32 (s, 1H), 4.75-4.49 (m, 2.5H), 4.39-4.24 (m, 1H), 3.97-3.88 (m, 1H), 3.88-3.80 (m, 1H), 3.77 (d, J = 13.2 Hz, 0.5H), 3.57-3.45 (m, 2H), 3.39 (t, J = 12.3 Hz, 0.5H), 3.08-2.92 (m, 0.5H), 2.84 (d, J = 10.3 Hz, 1H), 2.72 (d, J = 11.2 Hz, 1H), 2.31 (s, 3H), 2.26-1.84 (m, 6H), 1.43-1.16 (m, 3H). MS (ESI): C$_{25}$H$_{28}$ClN$_5$O$_3$ requires 481; found 482 [M + H]$^+$. |
| E17 | 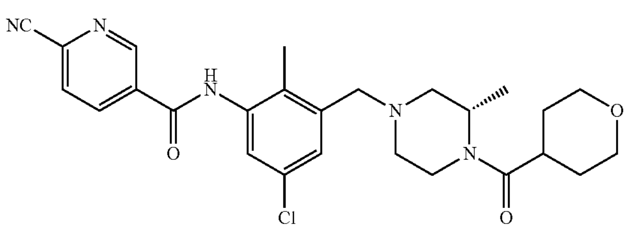 | DCM/DIPEA | $^1$H NMR (400 MHz, CDCl$_3$): 9.01 (s, 1H), 8.25 (s, 1H), 8.18-8.02 (m, 1H), 7.71 (s, 1H), 7.20 (s, 1H), 4.77-4.63 (m, 0.5H), 4.35-4.24 (m, 0.5H), 4.13-3.93 (m, 2.5H), 3.68-3.56 (m, 0.5H), 3.53-3.30 (m, 4.5H), 2.90-2.76 (m, 1H), 2.75-2.56 (m, 5.5H), 2.30 (s, 3H), 2.26-1.78 (m, 4H), 1.67-1.51 (m, 2H), 1.41-1.11 (m, 3H). MS (ESI): C$_{27}$H$_{32}$ClN$_5$O$_3$ requires 509; found 510 [M + H]$^+$ |

| | Structure | Solvent/base | Characterization |
|---|---|---|---|
| E18 | 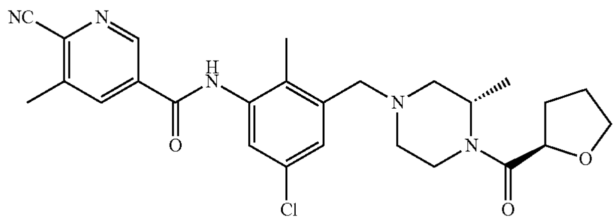 [SMILES: Cc1cc(C(=O)Nc2cc(Cl)cc(CN3CCN(C(=O)[C@H]4CCCO4)[C@@H](C)C3)c2C)cnc1C#N] | DCM/DIPEA | $^1$H NMR (400 MHz, CDCl$_3$): 9.03 (d, J = 5.6 Hz, 1H), 8.25-8.12 (m, 2H), 7.70 (brs, 1H), 7.19 (dd, J = 12.0 Hz, 2.0 Hz, 1H), 4.64-4.56 (m, 1.5H), 4.24-4.15 (m, 1H), 3.95-3.93 (m, 1H), 3.87-3.85 (m, 1.5H), 3.44-3.37 (m, 2.5H), 2.80-2.71 (m, 1H), 2.67 (s, 3H), 2.65-2.52 (m, 1H), 2.29 (d, J = 3.6 Hz, 3H), 2.25-1.80 (m, 6.5H), 1.35 (d, J = 6.8 Hz, 1.5H), 1.17 (d, J = 6.8 Hz, 1.5H). MS (ESI): C$_{26}$H$_{30}$ClN$_5$O$_3$ requires 495; found 496 [M + H]$^+$ |
| E19 | 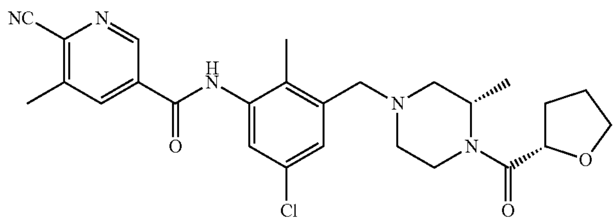 [SMILES: Cc1cc(C(=O)Nc2cc(Cl)cc(CN3CCN(C(=O)[C@@H]4CCCO4)[C@@H](C)C3)c2C)cnc1C#N] | DCM/DIPEA | $^1$H NMR (400 MHz, CDCl$_3$): 9.15-8.99 (m, 1H), 8.84-8.55 (m, 1H), 8.27 (brs, 1H), 7.56 (d, J = 6.3 Hz, 1H), 7.18 (brs, 1H), 4.63-4.49 (m, 1.5H), 4.40-4.26 (m, 0.5H), 4.14-4.02 (m, 0.5H), 3.94-3.77 (m, 2H), 3.75-3.64 (m, 0.5H), 3.53-3.22 (m, 2.5H), 2.86-2.60 (m, 4.5H), 2.59-2.43 (m, 1H), 2.38-1.66 (m, 9H), 1.40-1.05 (m, 3H). MS (ESI): C$_{26}$H$_{30}$ClN$_5$O$_3$ requires 495; found 496 [M + H]$^+$ |
| E20 | 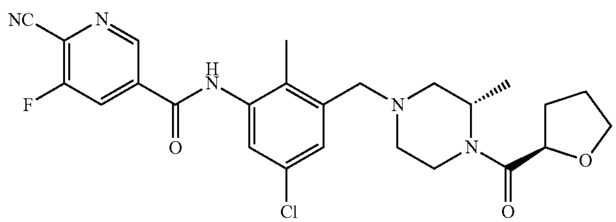 [SMILES: Cc1c(CN2CCN(C(=O)[C@H]3CCCO3)[C@@H](C)C2)cc(Cl)cc1NC(=O)c1cnc(C#N)c(F)c1] | DCM/DIPEA | $^1$H NMR (400 MHz, CDCl$_3$): 9.16 (d, J = 10.8 Hz, 1H), 8.95 (brs, 0.5H), 8.76 (brs, 0.5H), 8.33 (t J = 9.8 Hz, 1H), 7.56 (s, 1H), 7.21 (dd, J = 17.6 Hz, 1.6 Hz, 1H), 4.64-4.56 (m, 1H), 4.49 (brs, 0.5H), 4.15 (brs, 0.5H), 4.06-4.03 (m, 0.5H), 4.00-3.93 (m, 1H), 3.90-3.82 (m, 1.5H), 3.53-3.50 (m, 1H), 3.36-3.33 (m, 1H), 3.29-3.24 (m, 0.5H), 2.81-2.77 (m, 0.5H), 2.72-2.65 (m, 1H), 2.48-2.43 (m, 1H), 2.31-2.24 (m, 3H), 2.21-1.76 (m, 6H), 1.35-1.09 (m, 3H). MS (ESI): C$_{25}$H$_{27}$ClFN$_5$O$_3$ requires 499; found 500 [M + H]$^+$. |
| E21 | 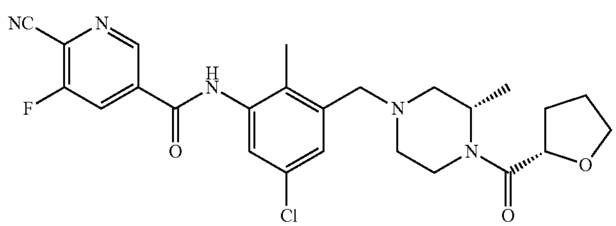 [SMILES: Cc1c(CN2CCN(C(=O)[C@@H]3CCCO3)[C@@H](C)C2)cc(Cl)cc1NC(=O)c1cnc(C#N)c(F)c1] | DCM/DIPEA | $^1$H NMR (400 MHz, CDCl$_3$): 9.61 (brs, 0.5H), 9.27-9.16 (m, 1.5H), 8.45-8.33 (m, 1H), 7.39 (brs, 1H), 7.21-7.19 (m, 1H), 4.58 (brs, 1H), 4.40-4.30 (m, 1H), 3.95-3.68 (m, 3H), 3.60-3.50 (m, 1H), 3.41-3.08 (m, 1.5H), 2.83-2.70 (m, 1H), 2.56-2.50 (m, 0.5H), 2.42-2.34 (m, 1H), 2.25(s, 3H), 2.13-2.12 (m, 3H), 2.02-1.94 (m, 2H), 1.71-1.50 (m, 1H), 1.30-1.10 (m, 3H). MS (ESI): C$_{25}$H$_{27}$ClFN$_5$O$_3$ requires 499; found 500 [M + H]$^+$. |

Example 22

N-(5-chloro-2-methyl-3-(((S)-3-methyl-4-((R)-tetrahydrofuran-2-carbonyl)piperazin-1-yl)methyl)phenyl)-3-cyano-5-fluorobenzamide (E22)

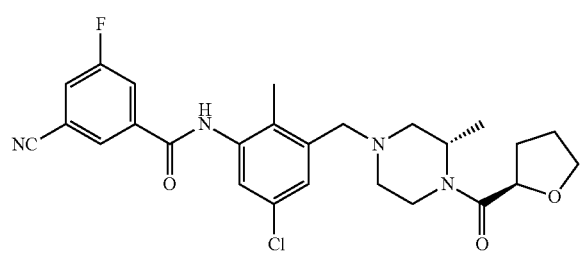 [SMILES: Cc1c(CN2CCN(C(=O)[C@H]3CCCO3)[C@@H](C)C2)cc(Cl)cc1NC(=O)c1cc(F)cc(C#N)c1]

To a solution of (S)—N-(5-chloro-2-methyl-3-((3-methylpiperazin-1-yl)methyl)phenyl)-3-cyano-5-fluorobenzamide, 2 hydrochloric acid salt (D60, 150 mg) in DCM (20 mL) were added (R)-tetrahydrofuran-2-carboxylic acid (43.4 mg), HATU (142 mg) and DIPEA (0.065 mL). After stirred for 2 hours, the mixture was concentrated under reduced pressure. The residue was purified by preparative HPLC (Gilson GX-281, mobile phase: 0.01% NH$_4$HCO$_3$/H$_2$O, CH$_3$CN, 50-95%, 9.0 min, 30 mL/min) to give the title compound (100 mg) as a white solid. $^1$H NMR (400 MHz, CDCl$_3$): 8.16 (brs, 0.5H), 8.04-8.02 (m, 1.5H), 7.94 (t, J=8.2 Hz 1H), 7.69 (s, 1H), 7.58 (d, J=6.8 Hz, 1H), 7.19 (d, J=7.3 Hz, 1H), 4.68-4.61 (m, 1H), 4.58-4.55 (m, 0.5H), 4.24-4.13 (m, 1H), 3.98-3.93 (m, 1H), 3.89-3.81 (m, 1.5H), 3.48-3.26 (m, 2.5H), 2.88-2.72 (m, 1H), 2.69-2.63 (m, 1H), 2.57 (d, J=11.3 Hz, 0.5H), 2.30 (s, 3H), 2.24-1.87 (m, 6H), 1.36-1.17 (m, 3H). MS (ESI): C$_{26}$H$_{28}$ClFN$_4$O$_3$ requires 498; found 499 [M+H]$^+$.

Example 23

N-(5-chloro-2-methyl-3-(((S)-3-methyl-4-((S)-tetrahydrofuran-2-carbonyl)piperazin-1-yl)methyl)phenyl)-3-cyano-5-fluorobenzamide (E23)

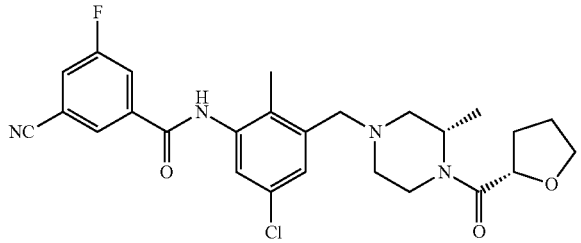 [SMILES: Cc1c(CN2CCN(C(=O)[C@@H]3CCCO3)[C@@H](C)C2)cc(Cl)cc1NC(=O)c1cc(F)cc(C#N)c1]

To a solution of (S)—N-(5-chloro-2-methyl-3-((3-methylpiperazin-1-yl)methyl)phenyl)-3-cyano-5-fluorobenzamide, 2 hydrochloric acid salt (D60, 100 mg) in DCM (20 mL) were added (S)-tetrahydrofuran-2-carboxylic acid (29.0 mg), HATU (114 mg) and DIPEA (0.131 mL). After stirring for 2 hours, the mixture was concentrated under reduced pressure. The residue was purified by preparative HPLC (Gilson GX-281, mobile phase: 0.01% $NH_4HCO_3/H_2O$, $CH_3CN$, 50-95%, 9.0 min, 30 mL/min) to give the title compound (54 mg) as a white solid. $^1H$ NMR (400 MHz, $CDCl_3$): 7.99 (brs, 1H), 7.91 (brs, 1.5H), 7.82-7.72 (m, 1.5H), 7.58 (d, J=7.3 Hz, 1H), 7.20 (d, J=2.0 Hz, 1H), 4.73-4.65 (m, 0.5H), 4.57 (brs, 1H), 4.40-4.25 (m, 1H), 3.97-3.91 (m, 1H), 3.88-3.83 (m, 1H), 3.78-3.70 (m, 0.5H), 3.48-3.36 (m, 2.5H), 2.94-2.85 (m, 0.5H), 2.80-2.61 (m, 2H), 2.35-2.15 (m, 5H), 2.10-1.86 (m, 4H), 1.34-1.22 (m, 3H). MS (ESI): $C_{26}H_{28}ClFN_4O_3$ requires 498; found 499 $[M+H]^+$.

Example 24

N-(5-chloro-2-methyl-3-(((S)-3-methyl-4-((R)-tetrahydrofuran-2-carbonyl)piperazin-1-yl)methyl)phenyl)-3-cyanobenzamide (E24)

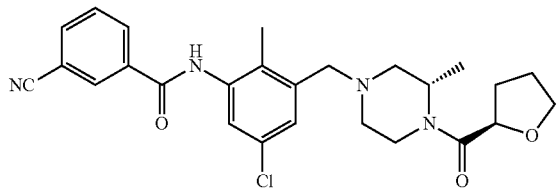 [SMILES: Cc1c(CN2CCN(C(=O)[C@H]3CCCO3)[C@@H](C)C2)cc(Cl)cc1NC(=O)c1cccc(C#N)c1]

To a mixture of (S)—N-(5-chloro-2-methyl-3-((3-methylpiperazin-1-yl)methyl)phenyl)-3-cyanobenzamide (D52, 200 mg) in DMF (5 mL) was added HATU (298 mg) at RT. The mixture was stirred at 25° C. for 10 mins, and then DIPEA (135 mg) was added. The mixture was stirred at 25° C. overnight. The mixture was partitioned between water and EA. The organic phase was dried over $Na_2SO_4$, filtered through a thin pad of celite and concentrated to give a brown oil, which was purified by preparative HPLC (Gilson GX-281, mobile phase: 0.01% $NH_4HCO_3/H_2O$, $CH_3CN$, 50-95%, 9.0 mins, 30 mL/min) to give the title compound (50 mg) as a white solid. $^1H$ NMR (400 MHz, DMSO-$d_6$): 10.19 (s, 1H), 8.40 (s, 1H), 8.26 (d, J=7.8 Hz, 1H), 8.08 (d, J=7.8 Hz, 1H), 7.76 (t, J=7.8 Hz, 1H), 7.39 (d, J=1.5 Hz, 1H), 7.29-7.27 (m, 1H), 4.67-4.59 (m, 1H), 4.54-4.45 (m, 0.5H), 4.24-4.11 (m, 1H), 3.83-3.70 (m, 2.5H), 3.49-3.40 (m, 2H), 3.23-3.12 (m, 0.5H), 2.85-2.72 (m, 1.5H), 2.64 (d, J=11.3 Hz, 1H), 2.22 (s, 3H), 2.18-1.75 (m, 6H), 1.28-1.11 (m, 3H). MS (ESI): $C_{26}H_{29}ClN_4O_3$ requires 480; found 481 $[M+H]^+$.

Example 25

N-(5-chloro-2-methyl-3-(((S)-3-methyl-4-((R)-tetrahydrofuran-3-carbonyl)piperazin-1-yl)methyl)phenyl)-3-cyanobenzamide (E25)

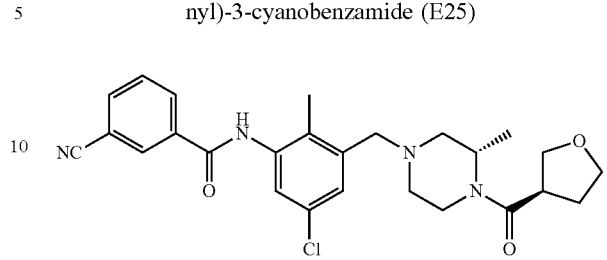

To a mixture of (S)—N-(5-chloro-2-methyl-3-((3-methylpiperazin-1-yl)methyl)phenyl)-3-cyanobenzamide (D52, 200 mg) in DMF (5 mL) was added HATU (298 mg) at RT. The mixture was stirred at 25° C. for 10 mins, and then DIPEA (135 mg) was added. The mixture was stirred at 25° C. overnight. The resulting mixture was partitioned between water and EA. The organic phase was dried over $Na_2SO_4$, filtered through a thin pad of celite and concentrated to give a brown oil, which was purified by preparative HPLC (Gilson GX-281, mobile phase: 0.01% $NH_4HCO_3/H_2O$, $CH_3CN$, 50-95%, 9.0 mins, 30 mL/min) to give the title compound (60 mg) as a white solid. $^1H$ NMR (400 MHz, DMSO-$d_6$): 10.19 (s, 1H), 8.41 (s, 1H), 8.26 (d, J=7.8 Hz, 1H), 8.08 (d, J=7.8 Hz, 1H), 7.76 (t, J=7.8 Hz, 1H), 7.39 (d, J=2.0 Hz, 1H), 7.28 (brs, 1H), 4.56 (brs, 0.5H), 4.22-4.19 (m, 1H), 3.96-3.92 (m, 0.5H), 3.85-3.60 (m, 4H), 3.50-3.43 (m, 2H), 3.34-3.27 (m, 1H), 3.22-3.16 (m, 0.5H), 2.84-2.74 (m, 1.5H), 2.65 (d, J=11.3 Hz, 1H), 2.22 (s, 3H), 2.16-1.90 (m, 4H), 1.27-1.11 (m, 3H). MS (ESI): $C_{26}H_{29}ClN_4O_3$ requires 480; found 481 $[M+H]^+$.

Example 26

N-(5-chloro-2-methyl-3-(((S)-3-methyl-4-((S)-tetrahydrofuran-2-carbonyl)piperazin-1-yl)methyl)phenyl)-3-cyanobenzamide (E26)

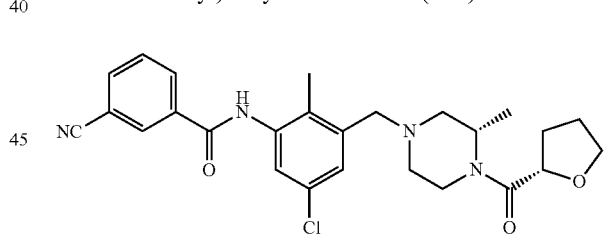

To a solution of (S)—N-(5-chloro-2-methyl-3-((3-methylpiperazin-1-yl)methyl)phenyl)-3-cyanobenzamide (D52, 600 mg) in DMF (50 mL) was added (S)-tetrahydrofuran-2-carboxylic acid (110 mg), HATU (1192 mg) and DIPEA (0.547 mL). The mixture was stirred at RT for 2 hours. Water was added. The solution was extracted with EA (3×50 mL). The filtrate was washed with sat. $NaHCO_3$ solution, water and brine. The resulting mixture was dried over $MgSO_4$. After filtration, the residue was purified by preparative HPLC to afford the title compound (50 mg) as a white solid. $^1H$ NMR (400 MHz, $CDCl_3$): 8.22 (s, 1H), 8.17 (d, J=7.5 Hz, 1H), 8.06-7.96 (m, 1H), 7.86 (d, J=7.8 Hz, 1H), 7.75 (brs, 1H), 7.66 (t, J=7.9 Hz, 1H), 7.18 (d, J=2.0 Hz, 1H), 4.67 (brs, 0.5H), 4.57 (t, J=6.1 Hz, 1H), 4.36 (brs, 0.5H), 4.31-4.22 (m, 0.5H), 3.95-3.90 (m, 1H), 3.87-3.82 (m, 1H), 3.77-3.68 (m, 0.5H), 3.47-3.39 (m, 2.5H), 2.95-2.84 (m, 0.5H), 2.81-2.59 (m, 2H), 2.35-2.15 (m, 5H), 2.10-1.85 (m, 4H), 1.33-1.21 (m, 3H). MS (ESI): $C_{26}H_{29}ClN_4O_3$ requires 480; found 481 $[M+H]^+$.

Example 27

N-(5-chloro-2-methyl-3-(((S)-3-methyl-4-((S)-tetrahydrofuran-3-carbonyl)piperazin-1-yl)methyl)phenyl)-3-cyanobenzamide (E27)

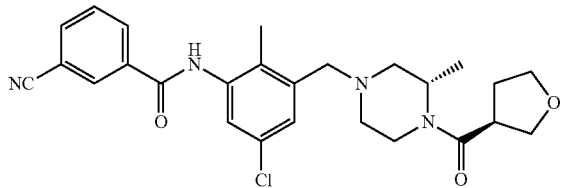

To a solution of (S)—N-(5-chloro-2-methyl-3-((3-methylpiperazin-1-yl)methyl)phenyl)-3-cyanobenzamide (D52, 150 mg) in DMF (50 mL) was added (S)-tetrahydrofuran-3-carboxylic acid (54.6 mg), HATU (149 mg) and DIPEA (0.137 mL). The mixture was stirred at RT for 2 hours. Water was added. The solution was extracted with EA (3×50 mL). The filtrate was washed with sat. NaHCO$_3$ solution, water and brine. The resulting solution was dried over MgSO$_4$. After filtration, the residue was purified by chiral preparative HPLC to afford the title compound (20 mg) as a white solid. $^1$H NMR (400 MHz, CDCl$_3$): 8.19 (s, 1H), 8.15 (d, J=7.8 Hz, 1H), 7.89 (d, J=7.8 Hz, 1H), 7.82 (brs, 1H), 7.76 (d, J=7.5 Hz, 1H), 7.68 (t, J=7.8 Hz, 1H), 7.18 (d, J=2.0 Hz, 1H), 4.77 (brs, 0.5H), 4.39 (d, J=14.1 Hz, 0.5H), 4.07-3.79 (m, 4.5H), 3.64 (d, J=13.6 Hz, 0.5H), 3.52-3.32 (m, 2.5H), 3.27-3.14 (m, 1H), 2.98-2.66 (m, 2.5H), 2.32 (s, 3H), 2.26-2.00 (m, 4H), 1.36-1.22 (m, 3H). MS (ESI): C$_{26}$H$_{29}$ClN$_4$O$_3$ requires 480; found 481 [M+H]$^+$.

Example 28

N-(5-chloro-2-methyl-3-(((S)-3-methyl-4-((R)-tetrahydrofuran-2-carbonyl)piperazin-1-yl)methyl)phenyl)-3-cyano-4-fluorobenzamide (E28)

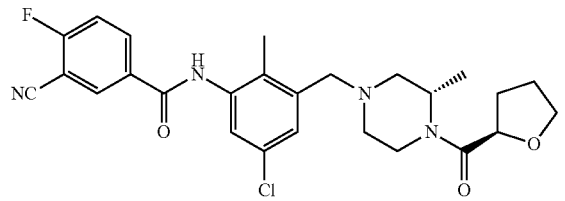 [SMILES: Cc1c(CN2CCN(C(=O)[C@H]3CCCO3)[C@@H](C)C2)cc(Cl)cc1NC(=O)c1ccc(F)c(C#N)c1]

To a solution of (S)—N-(5-chloro-2-methyl-3-((3-methylpiperazin-1-yl)methyl)phenyl)-3-cyano-4-fluorobenzamide (D53, 96.5 mg) and (R)-tetrahydrofuran-2-carboxylic acid (36.5 mg) in anhydrous DMF (5 mL) were added HATU (182.3 mg) and DIPEA (0.126 mL). The reaction mixture was stirred overnight, and then purified directly by MDAP (basic condition) to afford the title compound (65.9 mg) as a white solid. $^1$H NMR (400 MHz, MeOD-d$_4$): 8.39 (dd, J=5.9 Hz, 2.0 Hz, 1H), 8.34-8.30 (m, 1H), 7.54 (t, J=8.9 Hz, 1H), 7.34 (s, 1H), 7.30 (brs, 1H), 4.75-4.67 (m, 1H), 4.66-4.55 (m, 1.5H), 4.27 (d, J=13.4 Hz, 0.5H), 4.22-4.14 (m, 0.5H), 4.00-3.90 (m, 1H), 3.89-3.78 (m, 1.5H), 3.55-3.45 (m, 2H), 3.39-3.33 (m, 0.5H), 3.05-2.96 (m, 0.5H), 2.89-2.78 (m, 1H), 2.77-2.69 (m, 1H), 2.30 (s, 3H), 2.27-2.07 (m, 3H), 2.02-1.87 (m, 3H), 1.38-1.23 (m, 3H). $^{19}$F NMR (376 MHz, MeOD-d$_4$): −105.1. MS (ESI): C$_{26}$H$_{28}$ClFN$_4$O$_3$ requires 498; found 499 [M+H]$^+$.

Example 29

N-(5-chloro-2-methyl-3-(((S)-3-methyl-4-((S)-tetrahydrofuran-2-carbonyl)piperazin-1-yl)methyl)phenyl)-3-cyano-4-fluorobenzamide (E29)

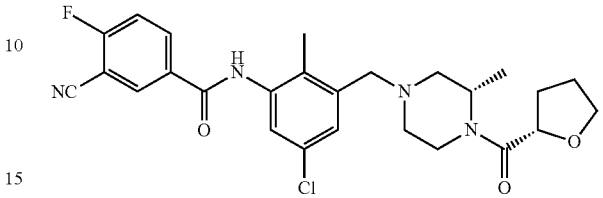

To a solution of (S)—N-(5-chloro-2-methyl-3-((3-methylpiperazin-1-yl)methyl)phenyl)-3-cyano-4-fluorobenzamide (D53, 99.8 mg) and (S)-tetrahydrofuran-2-carboxylic acid (39.6 mg) in anhydrous DMF (5 mL) were added HATU (189.3 mg) and DIPEA (0.130 mL). The mixture was stirred overnight, and then purified directly by MDAP (basic condition) to afford the title compound (68.9 mg) as a white solid. $^1$H NMR (400 MHz, MeOD-d$_4$): 8.39 (dd, J=6.1 Hz, 2.0 Hz, 1H), 8.36-8.29 (m, 1H), 7.54 (t, J=8.8 Hz, 1H), 7.35 (d, J=2.0 Hz, 1H), 7.31 (d, J=2.0 Hz, 1H), 4.75-4.53 (m, 2.5H), 4.39-4.24 (m, 1H), 3.97-3.89 (m, 1H), 3.88-3.80 (m, 1H), 3.76 (d, J=13.7 Hz, 0.5H), 3.57-3.45 (m, 2H), 3.45-3.36 (m, 0.5H), 3.07-2.93 (m, 0.5H), 2.84 (d, J=10.8 Hz, 1H), 2.72 (d, J=11.5 Hz, 1H), 2.30 (s, 3H), 2.27-1.87 (m, 6H), 1.42-1.21 (m, 3H). $^{19}$F NMR (376 MHz, MeOD-d$_4$): −106.7. MS (ESI): C$_{26}$H$_{28}$ClFN$_4$O$_3$ requires 498; found 499 [M+H]$^+$.

Example 30

N-(5-chloro-2-methyl-3-(((S)-3-methyl-4-((R)-tetrahydrofuran-2-carbonyl)piperazin-1-yl)methyl)phenyl)-5-fluoro-6-methylnicotinamide (E30)

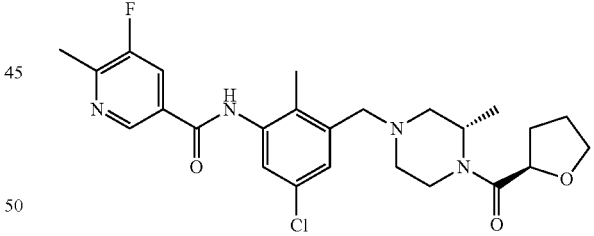

To a solution of (R)-tetrahydrofuran-2-carboxylic acid (44.6 mg), (S)—N-(5-chloro-2-methyl-3-((3-methylpiperazin-1-yl)methyl)phenyl)-5-fluoro-6-methylnicotinamide (D55, 150 mg) and DIPEA (0.201 mL) in DCM (10 mL) was added HATU (175 mg) at 0° C. The mixture was stirred at RT overnight, and then washed with aqueous NaHCO$_3$ solution and brine for three times. The resulting solution was dried over Na$_2$SO$_4$, filtered and concentrated. The residue was purified by preparative HPLC to give the title compound (34 mg) as a white solid. $^1$H NMR (400 MHz, DMSO-d$_6$): 10.19 (s, 1H), 8.89 (s, 1H), 8.12 (d, J=10.0 Hz, 1H), 7.39 (s, 1H), 7.29 (d, J=4.8 Hz, 1H), 4.68-4.58 (m, 1H), 4.55-4.47 (m, 0.5H), 4.24-4.12 (m, 1H), 3.85-3.69 (m, 2.5H), 3.51-3.41 (m, 2H), 3.22-3.13 (m, 0.5H), 2.86-2.69 (m, 1.5H), 2.64 (d, J=11.0 Hz, 1H), 2.54 (d, J=2.8 Hz, 3H), 2.22 (s, 3H), 2.18-1.73 (m, 6H), 1.29-1.12 (m, 3H). $^{19}$F NMR (376 MHz, DMSO-$d_6$): −124.7. MS (ESI): $C_{25}H_{30}ClFN_4O_3$ requires 488; found 489 [M+H]$^+$.

Example 31

N-(5-chloro-2-methyl-3-(((S)-3-methyl-4-((S)-tetrahydrofuran-2-carbonyl)piperazin-1-yl)methyl)phenyl)-5-fluoro-6-methylnicotinamide (E31)

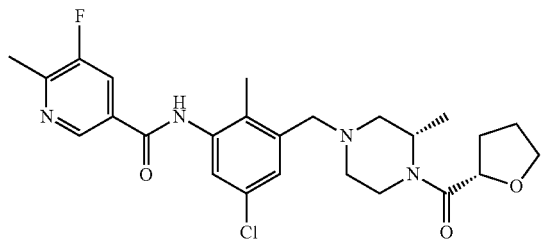 [SMILES: Cc1ncc(C(=O)Nc2cc(Cl)cc(CN3CCN(C(=O)[C@@H]4CCCO4)[C@@H](C)C3)c2C)cc1F]

To a solution of (S)-tetrahydrofuran-2-carboxylic acid (44.6 mg), (S)—N-(5-chloro-2-methyl-3-((3-methylpiperazin-1-yl)methyl)phenyl)-5-fluoro-6-methylnicotinamide (D55, 150 mg) and DIPEA (0.201 mL) in DCM (10 mL) was added HATU (175 mg) at 0° C. The mixture was stirred at RT overnight, and then washed with aqueous NaHCO$_3$ solution and brine for three times. The resulting solution was dried over Na$_2$SO$_4$, filtered and concentrated. The residue was purified by preparative HPLC to give the title compound (31 mg) as a white solid. $^1$H NMR (400 MHz, DMSO-$d_6$): 10.19 (s, 1H), 8.89 (s, 1H), 8.12 (d, J=10.0 Hz, 1H), 7.39 (d, J=2.0 Hz, 1H), 7.28 (d, J=1.8 Hz, 1H), 4.59 (t, J=6.5 Hz, 1H), 4.56-4.46 (m, 0.5H), 4.37-4.26 (m, 0.5H), 4.16 (d, J=12.0 Hz, 0.5H), 3.85-3.67 (m, 2.5H), 3.52-3.38 (m, 2H), 3.28-3.14 (m, 0.5H), 2.89-2.70 (m, 1.5H), 2.64 (d, J=10.8 Hz, 1H), 2.54 (d, J=2.8 Hz, 3H), 2.30-2.14 (m, 4H), 2.05-1.73 (m, 5H), 1.32-1.06 (m, 3H). $^{19}$F NMR (376 MHz, DMSO-$d_6$): −124.7. MS (ESI): $C_{25}H_{30}ClFN_4O_3$ requires 488; found 489 [M+H]$^+$.

Example 32

N-(5-chloro-2-methyl-3-(((S)-3-methyl-4-((R)-tetrahydrofuran-2-carbonyl)piperazin-1-yl)methyl)phenyl)-5-cyano-6-methylnicotinamide (E32)

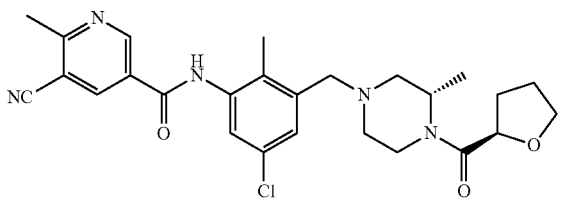 [SMILES: Cc1ncc(C(=O)Nc2cc(Cl)cc(CN3CCN(C(=O)[C@H]4CCCO4)[C@@H](C)C3)c2C)cc1C#N]

To a solution of (S)—N-(5-chloro-2-methyl-3-((3-methylpiperazin-1-yl)methyl)phenyl)-5-cyano-6-methylnicotinamide (D57, 95.0 mg) and (R)-tetrahydrofuran-2-carboxylic acid (40.5 mg) in anhydrous DMF (5 mL) were added HATU (182.8 mg) and DIPEA (0.13 mL). The mixture was stirred at RT overnight, and directly purified by MDAP (basic condition, ACN/H$_2$O (containing 0.05% NH$_3$H$_2$O), ACN %=30-70%) to give the title compound (78.5 mg) as a white solid. $^1$H NMR (400 MHz, MeOD-$d_4$): 9.21 (s, 1H), 8.64 (s, 1H), 7.44 (brs, 2H), 4.79-4.62 (m, 1.5H), 4.60-4.11 (m, 2H), 3.99-3.79 (m, 2.5H), 3.76-3.35 (m, 2.5H), 3.24-2.96 (m, 1.5H), 2.94-2.67 (m, 4H), 2.33 (s, 3H), 2.27-1.78 (m, 5H), 1.52-1.13 (m, 3H). MS (ESI): $C_{26}H_{30}ClN_5O_3$ requires 495; found 496 [M+H]$^+$.

Example 33

N-(5-chloro-2-methyl-3-(((S)-3-methyl-4-((S)-tetrahydrofuran-2-carbonyl)piperazin-1-yl)methyl)phenyl)-5-cyano-6-methylnicotinamide (E33)

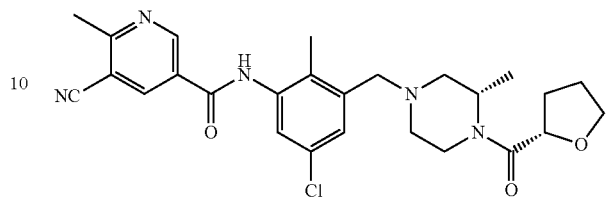

To a solution of (S)—N-(5-chloro-2-methyl-3-((3-methylpiperazin-1-yl)methyl)phenyl)-5-cyano-6-methylnicotinamide (D57, 95.6 mg) and (S)-tetrahydrofuran-2-carboxylic acid (40.0 mg) in anhydrous DMF (5 mL) were added HATU (176.3 mg) and DIPEA (0.13 mL). The mixture was stirred at RT overnight, and directly purified by MDAP (basic condition, ACN/H$_2$O (containing 0.05% NH$_3$H$_2$O), ACN %=30-70%) to give the title compound (75.9 mg) as a white solid. $^1$H NMR (400 MHz, MeOD-$d_4$): 9.21 (s, 1H), 8.64 (s, 1H), 7.43 (brs, 2H), 4.76-4.60 (m, 1.5H), 4.58-4.11 (m, 2H), 3.96-3.77 (m, 2.5H), 3.75-3.36 (m, 2.5H), 3.21-2.96 (m, 1.5H), 2.93-2.60 (m, 4H), 2.33 (s, 3H), 2.25-1.83 (m, 5H), 1.51-1.13 (m, 3H). MS (ESI): $C_{26}H_{30}ClN_5O_3$ requires 495; found 496 [M+H]$^+$.

Example 34&35

N-(5-chloro-2-methyl-3-(((S)-3-methyl-4-((R)-2-methyltetrahydrofuran-2-carbonyl)piperazin-1-yl)methyl)phenyl)-3-cyanobenzamide & N-(5-chloro-2-methyl-3-(((S)-3-methyl-4-((S)-2-methyltetrahydrofuran-2-carbonyl)piperazin-1-yl)methyl)phenyl)-3-cyanobenzamide (E34&E35)

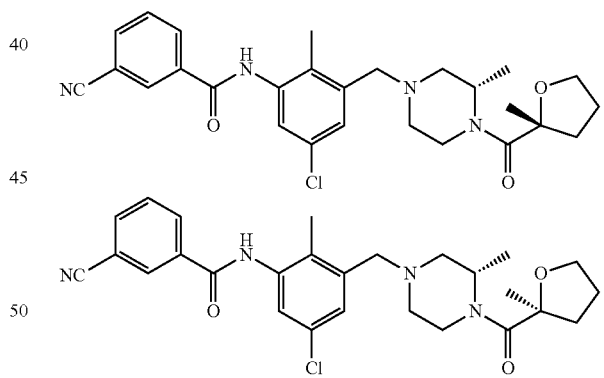

A mixture of 2-methyltetrahydrofuran-2-carboxylic acid (52.1 mg) and (S)—N-(5-chloro-2-methyl-3-((3-methylpiperazin-1-yl)methyl)phenyl)-3-cyanobenzamide (D52, 153 mg) in DMF (6 mL) was added HATU (228 mg) at RT. After stirring for 10 mins, DIPEA (0.105 mL) was added. The mixture was stirred at 50° C. for 18 hours. The resulting mixture was diluted with water (10 mL), and then extracted with EA (30 mL). The organic phase was dried over Na$_2$SO$_4$, filtered and concentrated to give a brown oil. The residue was purified by preparative HPLC (Gilson GX-281, mobile phase: 0.01% NH$_4$HCO$_3$/H$_2$O, CH$_3$CN, 50-95%, 9.0 min, 30 mL/min) to give the crude product (150 mg) as a white solid, which was purified by preparative chiral HPLC (column: AD-H 4.6×250 mm, 5 um; co-solvent: MeOH (0.1% DEA); column temperature 39.9° C.; $CO_2$ flow rate: 2.25 mL/min; co-solvent flow rate: 0.75 mL/min; co-solvent: 25%) to give the title compounds (50 mg and 65 mg) as white solids. Isomer 1: $^1$H NMR (400 MHz, $CDCl_3$): 8.21 (brs, 1H), 8.16 (d, J=8.0 Hz, 1H), 7.87 (d, J=7.8 Hz, 1H), 7.82-7.75 (m, 1H), 7.67 (t, J=7.8 Hz, 1H), 7.22-7.15 (m, 1H), 5.18-5.06 (m, 0.5H), 4.82-4.68 (m, 0.5H), 4.49 (d, J=13.8 Hz, 0.5H), 4.29-4.18 (m, 0.5H), 4.08-3.87 (m, 1H), 3.87-3.64 (m, 1H), 3.46-3.30 (m, 2.5H), 3.00-2.67 (m, 2.5H), 2.61 (d, J=11.3 Hz, 1H), 2.31 (s, 3H), 2.27-2.13 (m, 1H), 2.07-1.77 (m, 3H), 1.68-1.53 (m, 2H), 1.50-1.41 (m, 3H), 1.38-1.15 (m, 3H). MS (ESI): $C_{27}H_{31}ClN_4O_3$ requires 494; found 495 $[M+H]^+$. Isomer 2: $^1$H NMR (400 MHz, $CDCl_3$): 8.20 (brs, 1H), 8.16 (d, J=7.8 Hz, 1H), 7.87 (d, J=7.8 Hz, 1H), 7.83-7.76 (m, 1H), 7.67 (t, J=7.8 Hz, 1H), 7.18 (s, 1H), 4.90-4.80 (m, 0.5H), 4.72 (d, J=12.5 Hz, 0.5H), 4.67-4.57 (m, 0.5H), 4.38-4.29 (m, 0.5H), 3.99-3.91 (m, 1H), 3.85-3.72 (m, 1H), 3.48-3.32 (m, 2H), 3.27-3.15 (m, 0.5H), 2.96-2.81 (m, 1.5H), 2.80-2.59 (m, 2H), 2.32 (s, 3H), 2.23-1.78 (m, 4H), 1.70-1.55 (m, 2H), 1.51-1.38 (m, 3H), 1.37-1.17 (m, 3H). MS (ESI): $C_{27}H_{31}ClN_4O_3$ requires 494; found 495 $[M+H]^+$.

Example 36-55

Examples 36-55 were prepared using a similar procedure to that described for Examples 34&35, with the specified reaction base or solvent listed in the table.

E36&E37: N-(5-chloro-2-methyl-3-(((S)-3-methyl-4-((R)-tetrahydrofuran-3-carbonyl)piperazin-1-yl)methyl)phenyl)-6-methylnicotinamide & N-(5-chloro-2-methyl-3-(((S)-3-methyl-4-((S)-tetrahydrofuran-3-carbonyl)piperazin-1-yl)methyl)phenyl)-6-methylnicotinamide E38&E39: N-(5-chloro-2-methyl-3-(((S)-3-methyl-4-((R)-2-methyltetrahydrofuran-2-carbonyl)piperazin-1-yl)methyl)phenyl)-6-methylnicotinamide & N-(5-chloro-2-methyl-3-(((S)-3-methyl-4-((S)-2-methyltetrahydrofuran-2-carbonyl)piperazin-1-yl)methyl)phenyl)-6-methylnicotinamide E40&E41: N-(5-chloro-2-methyl-3-(((S)-3-methyl-4-((S)-tetrahydro-2H-pyran-3-carbonyl)piperazin-1-yl)methyl)phenyl)-3-cyanobenzamide & N-(5-chloro-2-methyl-3-(((S)-3-methyl-4-((R)-tetrahydro-2H-pyran-3-carbonyl)piperazin-1-yl)methyl)phenyl)-3-cyanobenzamide E42&E43: N-(5-chloro-2-methyl-3-(((S)-3-methyl-4-((R)-tetrahydro-2H-pyran-2-carbonyl)piperazin-1-yl)methyl)phenyl)-3-cyanobenzamide & N-(5-chloro-2-methyl-3-(((S)-3-methyl-4-((S)-tetrahydro-2H-pyran-2-carbonyl)piperazin-1-yl)methyl)phenyl)-3-cyanobenzamide E44&E45: N-(5-chloro-2-methyl-3-(((S)-3-methyl-4-((R)-tetrahydro-2H-pyran-2-carbonyl)piperazin-1-yl)methyl)phenyl)-5-fluoronicotinamide & N-(5-chloro-2-methyl-3-(((S)-3-methyl-4-((S)-tetrahydro-2H-pyran-2-carbonyl)piperazin-1-yl)methyl)phenyl)-5-fluoronicotinamide E46&E47: N-(5-chloro-2-methyl-3-(((S)-3-methyl-4-((S)-tetrahydro-2H-pyran-3-carbonyl)piperazin-1-yl)methyl)phenyl)-5-fluoronicotinamide & N-(5-chloro-2-methyl-3-(((S)-3-methyl-4-((R)-tetrahydro-2H-pyran-3-carbonyl)piperazin-1-yl)methyl)phenyl)-5-fluoronicotinamide E48&E49: N-(5-chloro-2-methyl-3-(((S)-3-methyl-4-((R)-tetrahydro-2H-pyran-3-carbonyl)piperazin-1-yl)methyl)phenyl)-2-methylthiazole-5-carboxamide & N-(5-chloro-2-methyl-3-(((S)-3-methyl-4-((S)-tetrahydro-2H-pyran-3-carbonyl)piperazin-1-yl)methyl)phenyl)-2-methylthiazole-5-carboxamide E50&E51: N-(5-chloro-2-methyl-3-(((S)-3-methyl-4-((S)-tetrahydro-2H-pyran-2-carbonyl)piperazin-1-yl)methyl)phenyl)-2-methylthiazole-5-carboxamide & N-(5-chloro-2-methyl-3-(((S)-3-methyl-4-((R)-tetrahydro-2H-pyran-2-carbonyl)piperazin-1-yl)methyl)phenyl)-2-methylthiazole-5-carboxamide E52&E53: N-(5-chloro-2-methyl-3-(((S)-3-methyl-4-((S)-tetrahydro-2H-pyran-3-carbonyl)piperazin-1-yl)methyl)phenyl)-6-methylnicotinamide & N-(5-chloro-2-methyl-3-(((S)-3-methyl-4-((R)-tetrahydro-2H-pyran-3-carbonyl)piperazin-1-yl)methyl)phenyl)-6-methylnicotinamide E54&E55: N-(5-chloro-2-methyl-3-(((S)-3-methyl-4-((R)-tetrahydro-2H-pyran-2-carbonyl)piperazin-1-yl)methyl)phenyl)-6-methylnicotinamide & N-(5-chloro-2-methyl-3-(((S)-3-methyl-4-((S)-tetrahydro-2H-pyran-2-carbonyl)piperazin-1-yl)methyl)phenyl)-6-methylnicotinamide

| | Structure | Solvent/base | Characterization |
|---|---|---|---|
| E36 & E37 | (structure) | DCM/DIPEA | Isomer 1: $^1$H NMR (400 MHz, MeOD-$d_4$): 9.00 (d, J = 1.6 Hz, 1H), 8.29 (dd, J = 8.4 Hz, 2.4 Hz, 1H), 7.48 (d, J = 8.0 Hz, 1H), 7.36 (d, J = 2.4 Hz, 1H), 7.31 (d, J = 2.4 Hz, 1H), 4.75-4.60 (m, 1H), 4.25-4.18 (m, 1H), 4.10-3.71 (m, 5H), 3.55-3.35 (m, 3.5H), 3.01-2.98 (m, 0.5H), 2.90-2.85 (m, 1H), 2.83-2.71 (m, 1H), 2.65 (s, 3H), 2.33 (s, 3H), 2.29-1.94 (m, 4H), 1.39-1.14 (m, 3H). MS (ESI): $C_{25}H_{31}ClN_4O_3$ requires 470; found 471 $[M + H]^+$. Isomer 2: $^1$H NMR (400 MHz, MeOD-$d_4$): 9.01 (d, J = 2.0 Hz, 1H), 8.28 (dd, J = 8.0 Hz, 2.4 Hz, 1H), 7.48 (d, J = 8.0 Hz, 1H), 7.36 (d, J = 2.0 Hz, 1H), 7.32 (s, 1H), 4.67 (brs, 1H), 4.35-4.30 (m, 1H), 3.98-3.74 (m, 5H), 3.57-3.46 (m, 2H), 3.43-3.35 (m, 1.5H), 3.03-2.96 (m, 0.5H), 2.89-2.85 (m, 1H), 2.77-2.72 (m, 1H), 2.64 (s, 3H), 2.32 (s, 3H), 2.27-1.94 (m, 4H), 1.38-1.18 (m, 3H). MS (ESI): $C_{24}H_{31}ClN_4O_3$ requires 470; found 471 $[M + H]^+$. |

| | Structure | Solvent/base | Characterization |
|---|---|---|---|
| E38 & E39 | | DCM/DIPEA | Isomer 1: ¹H NMR (400 MHz, MeOD-d₄): 9.01 (s, 1H), 8.28 (dd, J = 8.0 Hz, 6.0 Hz, 1H), 7.48 (d, J = 8.4 Hz, 1H), 7.36 (d, J = 2.4 Hz, 1H), 7.31 (s, 1H), 5.11 (brs, 0.5H), 4.71 (brs, 0.5H), 4.52-4.48 (m, 0.5H), 4.25-4.20 (m, 0.5H), 3.98-3.90 (m, 1H), 3.89-3.83 (m, 0.5H), 3.73-3.70 (m, 0.5H), 3.50 (s, 2H), 3.43-3.41 (m, 0.5H), 3.07-3.01 (m, 0.5H), 2.86-2.80 (m, 1H), 2.74-2.62 (m, 2H), 2.64 (s, 3H), 2.32 (s, 3H), 2.28-2.18 (m, 1H), 2.10-2.02 (m, 1H), 1.98-1.78 (m, 2H), 1.72-1.65 (m, 1H), 1.47-1.45 (m, 3H), 1.29-1.27 (m, 3H). MS (ESI): $C_{26}H_{33}ClN_4O_3$ requires 484; found 485 [M + H]⁺. Isomer 2: ¹H NMR (400 MHz, MeOD-d₄): 9.01 (s, 1H), 8.28 (dd, J = 8.0 Hz, 5.6 Hz, 1H), 7.48 (d, J = 8.4 Hz, 1H), 7.36 (d, J = 2.4 Hz, 1H), 7.31 (s, 1H), 4.75-4.65 (m, 0.5H), 4.62 (brs, 0.5H), 4.56 (brs, 0.5H), 4.34-4.32 (m, 0.5H), 3.98-3.93 (m, 1H), 3.84-3.78 (m, 1H), 3.49 (s, 2H), 3.28-3.25 (m, 0.5H), 3.03-2.98 (m, 0.5H), 2.84-2.81 (m, 1H), 2.74-2.67 (m, 2H), 2.64 (s, 3H), 2.31 (s, 3H), 2.23-2.18 (m, 1H), 2.14-2.00 (m, 1H), 1.98-1.73 (m, 2H), 1.72-1.60 (m, 1H), 1.50-1.40 (m, 3H), 1.39-1.20 (m, 3H). MS (ESI): $C_{26}H_{33}ClN_4O_3$ requires 484; found 485 [M + H]⁺. |
| E40 & E41 | | DMF/DIPEA | Isomer 1: ¹H NMR (400 MHz, CDCl₃): 8.22 (brs, 1H), 8.18 (d, J = 7.8 Hz, 1H), 7.95-7.78 (m, 3H), 7.69 (t, J = 7.9 Hz, 1H), 7.19 (s, 1H), 4.78-4.67 (m, 0.5H), 4.33 (d, J = 14.8 Hz, 0.5H), 4.20-4.09 (m, 0.5H), 4.00-3.90 (m, 2H), 3.67 (d, J = 13.1 Hz, 0.5H), 3.57-3.30 (m, 4.5H), 2.93-2.59 (m, 3.5H), 2.33 (s, 3H), 2.28-2.13 (m, 1H), 2.09-1.81 (m, 3H), 1.77-1.65 (m, 2H), 1.42-1.15 (m, 3H). MS (ESI): $C_{27}H_{31}ClN_4O_3$ requires 494; found 495 [M + H]⁺. Isomer 2: ¹H NMR (400 MHz, CDCl₃): 8.20 (brs, 1H), 8.15 (d, J = 7.8 Hz, 1H), 7.90-7.75 (m, 3H), 7.67 (td, J = 7.8 Hz, 3.3 Hz, 1H), 7.18 (d, J = 9.3 Hz, 1H), 4.75-4.65 (m, 0.5H), 4.32 (d, J = 13.8 Hz, 0.5H), 4.11-4.02 (m, 0.5H), 3.94 (d, J = 10.8 Hz, 2H), 3.71-3.50 (m, 1.5H), 3.49-3.31 (m, 3.5H), 2.92-2.58 (m, 3.5H), 2.31 (s, 3H), 2.25-2.12 (m, 1H), 2.10-1.62 (m, 5H), 1.39-1.15 (m, 3H). MS (ESI): $C_{27}H_{31}ClN_4O_3$ requires 494; found 495 [M + H]⁺. |
| E42 & E43 | | DMF/DIPEA | Isomer 1: ¹H NMR (400 MHz, CDCl₃): 8.27-8.14 (m, 2H), 8.11-7.91 (m, 1H), 7.87 (d, J = 7.8 Hz, 1H), 7.81-7.72 (m, 1H), 7.66 (t, J = 7.9 Hz, 1H), 7.18 (d, J = 2.0 Hz, 1H), 4.74-4.64 (m, 0.5H), 4.36-4.20 (m, 1H), 4.08-3.96 (m, 2H), 3.73 (d, J = 13.8 Hz, 0.5H), 3.52-3.30 (m, 3.5H), 2.97-2.82 (m, 0.5H), 2.81-2.58 (m, 2H), 2.31 (s, 3H), 2.23-1.46 (m, 7.5H), 1.40-1.17 (m, 3H), 0.94-0.80 (m, 0.5H). MS (ESI): $C_{27}H_{31}ClN_4O_3$ requires 494; found 495 [M + H]⁺. Isomer 2: ¹H NMR (400 MHz, CDCl₃): 8.22 (d, J = 6.3 Hz, 1H), 8.17 (t, J = 6.9 Hz, 1H), 8.01-7.85 (m, 2H), 7.79 (brs, 1H), 7.71-7.64 (m, 1H), 7.18 (dd, J = 9.3 Hz, 1.8 Hz, 1H), 4.75-4.65 (m, 0.5H), 4.30 (d, J = 13.3 Hz, 0.5H), 4.16-4.07 (m, 1H), 4.06-3.98 (m, 1.5H), 3.82 (d, J = 13.1 Hz, 0.5H), 3.53-3.35 (m, 3H), 3.29 (td, J = 12.5 Hz, 2.4 Hz, 0.5H), 2.95-2.85 (m, 0.5H), 2.79-2.58 (m, 2H), 2.31 (s, 3H), 2.26-1.45 (m, 7.5H), 1.39-1.17 (m, 3H), 0.93-0.79 (m, 0.5H). MS (ESI): $C_{27}H_{31}ClN_4O_3$ requires 494; found 495 [M + H]⁺. |

| | Structure | Solvent/base | Characterization |
|---|---|---|---|
| E44 & E45 | 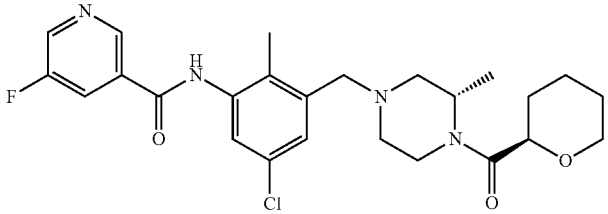 [SMILES: Cc1c(CN2CCN(C(=O)[C@H]3CCCCO3)[C@@H](C)C2)cc(Cl)cc1NC(=O)c1cncc(F)c1] | DCM/DIPEA | Isomer 1: $^1$H NMR (400 MHz, MeOD-d$_4$): 9.01 (s, 1H), 8.71 (d, J = 2.8 Hz, 1H), 8.19-8.16 (m, 1H), 7.38 (d, J = 2.4 Hz, 1H), 7.32 (d, J = 2.0 Hz, 1H), 4.63 (brs, 0.5H), 4.37-4.28 (m, 1H), 4.19-4.18 (m, 1H), 3.99-3.96 (m, 1H), 3.82-3.79 (m, 0.5H), 3.52-3.49 (m, 3H), 3.42-3.38 (m, 0.5H), 3.02-2.98 (m, 0.5H), 2.86 (d, J = 11.2 Hz, 1H), 2.74 (d, J = 11.6 Hz, 1H), 2.32 (s, 3H), 2.28-2.18 (m, 1H), 2.11-2.04 (m, 1H), 1.92 (brs, 1H), 1.69-1.54 (m, 5H), 1.38-1.26 (m, 3H). MS (ESI): C$_{25}$H$_{30}$ClFN$_4$O$_3$ requires 484; found 489[M + H]$^+$.<br>Isomer 2: 1H NMR (400 MHz, MeOD-d$_4$): 9.01 (s, 1H), 8.71 (d, J = 2.8 Hz, 1H), 8.19-8.16 (m, 1H), 7.38 (d, J = 2.0 Hz, 1H), 7.32 (s, 1H), 4.63 (brs, 0.5H), 4.27-4.23 (m, 1H), 4.19-4.17 (m, 1H), 4.00-3.98 (m, 1H), 3.87-3.84 (m, 0.5H), 3.58-3.52 (m, 3H), 3.35-3.33 (m, 0.5H), 3.03-2.97 (m, 0.5H), 2.86-2.82 (m, 1H), 2.76-2.72 (m, 1H), 2.32 (s, 3H), 2.26-2.19 (m, 1H), 2.12-2.04 (m, 1H), 1.92 (brs, 1H), 1.72-1.54 (m, 5H), 1.38-1.26 (m, 3H). MS (ESI): C$_{25}$H$_{30}$ClFN$_4$O$_3$ requires 488; found 489 [M + H]$^+$. |
| E46 & E47 | 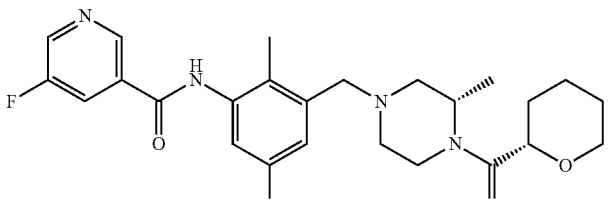 | DCM/DIPEA | Isomer 1: $^1$H NMR (400 MHz, MeOD-d$_4$): 9.10 (s, 1H), 8.71 (d, J = 2.8 Hz, 1H), 8.19-8.15 (m, 1H), 7.38 (d, J = 2.0 Hz, 1H), 7.32 (d, J = 2.0 Hz, 1H), 4.64 (brs, 0.5H), 4.31-4.28 (m, 1H), 3.91-3.80 (m, 2.5H), 3.52-3.38 (m, 4.5H), 2.95-2.71 (m, 3.5H), 2.32 (s, 3H), 2.18-1.66 (m, 6H), 1.38-1.23 (m, 3H). MS (ESI): C$_{25}$H$_{30}$ClFN$_4$O$_3$ requires 488; found 489 [M + H]$^+$.<br>Isomer 2: $^1$H NMR (400 MHz, MeOD-d$_4$): 9.01 (s, 1H), 8.71 (d, J = 2.4 Hz, 1H), 8.19-8.16 (m, 1H), 7.38 (d, J = 2.4 Hz, 1H), 7.32 (d, J = 2.0 Hz, 1H), 4.63 (brs, 0.5H), 4.32-4.29 (m, 1H), 3.92-3.81 (m, 2.5H), 3.55-3.38 (m, 4.5H), 2.93-2.71 (m, 3.5H), 2.32 (s, 3H), 2.26-1.88 (m, 3H), 1.74-1.66 (m, 3H), 1.39-1.22 (m, 3H). MS (ESI): C$_{25}$H$_{30}$ClFN$_4$O$_3$ requires 488; found 489 [M + H]$^+$. |
| E48 & E49 | 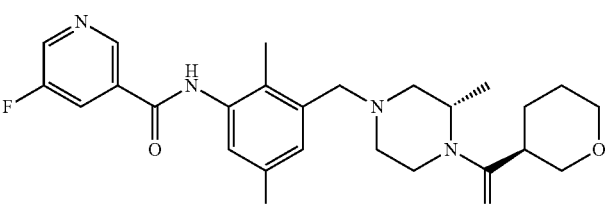 | DCM/DIPEA | Isomer 1: $^1$H NMR (400 MHz, CDCl$_3$): 8.12 (s, 1H), 7.81 (brs, 1H), 7.46 (brs, 1H), 7.16-7.13 (m, 1H), 4.73 (brs, 0.5H), 4.38-4.34 (m, 0.5H), 4.06 (brs, 0.5H), 3.95-3.93 (m, 2H), 3.64-3.52 (m, 2H), 3.48-3.37 (m, 3.5H), 2.87-2.82 (m, 0.5H), 2.79-2.75 (s, 3.5H), 2.73-2.63 (m, 1H), 2.29 (s, 3H), 2.20-2.15 (m, 1H), 2.04-1.99 (m, 1H), 1.88-1.65 (m, 2H), 1.64-1.61 (m, 2H), 1.36 (d, J = 6.4 Hz, 1.5H), 1.25 (s, 1H), 1.20 (d, J = 6.4 Hz, 1.5H). MS (ESI): C$_{24}$H$_{31}$ClN$_4$O$_3$S requires 490; found 491 [M + H]$^+$.<br>Isomer 2: $^1$H NMR (400 MHz, CDCl$_3$): 8.12 (s, 1H), 7.81 (brs, 1H), 7.46 (brs, 1H), 7.14 (brs, 1H), 4.74 (brs, 0.5H), 4.37-4.34 (m, 0.5H), 4.13-4.11 (m, 0.5H), 3.95-3.92 (m, 2H), 3.65-3.62 (m, 0.5H), 3.54-3.34 (m, 5H), 2.89-2.82 (m, 0.5H), 2.79-2.74 (m, 3.5H), 2.70-2.63 (m, 1H), 2.30 (s, 3H), 2.21-2.16 (m, 1H), 2.00-1.96 (m, 1H), 1.88-1.84 (m, 2H), 1.67 (brs, 2H), 1.34 (d, J = 6.4 Hz, 1.5H), 1.25 (brs, 1H), 1.20 (d, J = 6.4 Hz, 1.5H), MS (ESI): C$_{24}$H$_{31}$ClN$_4$O$_3$S requires 490; found 491 [M + H]$^+$. |

-continued

| | Structure | Solvent/base | Characterization |
|---|---|---|---|
| E50 & E51 | | DCM/DIPEA | Isomer 1: ¹H NMR (400 MHz, CDCl₃): 8.12 (s, 1H), 7.81 (brs, 1H), 7.49 (brs, 1H), 7.14 (d, J = 2.4 Hz, 1H), 4.73 (brs, 0.5H), 4.36-4.29 (m, 1H), 4.02-3.99 (m, 2H), 3.73-3.70 (m, 0.5H), 3.45-3.37 (m, 3.5H), 2.94-2.86 (m, 0.5H), 2.78-2.75 (s, 3.5H), 2.63-2.60 (m, 1H), 2.30 (s, 3H), 2.26-2.20 (m, 1H), 2.03-1.58 (m, 6.5H), 1.35-1.22 (m, 4H). MS (ESI): C₂₄H₃₁ClN₄O₃S requires 490; found 491 [M + H]⁺. Isomer 2: ¹H NMR (400 MHz, CDCl₃): 8.12 (s, 1H), 7.84-7.81 (m, 1H), 7.46 (d, J = 3.6 Hz, 1H), 7.15-7.13 (m, 1H), 4.73 (br, 0.5H), 4.39-4.36 (m, 0.5H), 4.11-4.08 (m, 1H), 4.03-3.98 (m, 1.5H), 3.83-3.79 (m, 0.5H), 3.49-3.43 (m, 2H), 3.38-3.26 (m, 1.5H), 2.95-2.87 (m, 0.5H), 2.78-2.71 (s, 3.5H), 2.65-2.62 (m, 1H), 2.30 (s, 3H), 2.25-2.17 (m, 1H), 2.07-1.62 (m, 6.5H), 1.35 (d, J = 6.8 Hz, 1.5H), 1.26-1.21 (m, 2.5H). MS (ESI): C₂₄H₃₁ClN₄O₃S requires 490; found 491 [M + H]⁺. |
| E52 & E53 | | DMF/DIPEA | Isomer 1: ¹H NMR (400 MHz, MeOD-d₄): 9.00 (d, J = 1.6 Hz, 1H), 8.28 (dd, J = 8.4 Hz, 2.4 Hz, 1H), 7.48 (d, J = 7.6 Hz, 1H), 7.36 (d, J = 2.0 Hz, 1H), 7.30 (d, J = 1.6 Hz, 1H), 4.64 (brs, 0.5H), 4.31-4.28 (m, 1H), 3.91-3.79 (m, 2.5H), 3.51-3.36 (m, 4.5H), 2.97-2.70 (m, 3.5H), 2.64 (s, 3H), 2.31 (s, 3H), 2.245-1.66 (m, 6H), 1.38-1.23 (m, 3H). MS (ESI): C₂₆H₃₃ClN₄O₃ requires 484; found 485 [M + H]⁺. Isomer 2: ¹H NMR (400 MHz, MeOD-d₄): 9.01 (d, J = 2.0 Hz, 1H), 8.28 (dd, J = 8.0 Hz, 2.4 Hz, 1H), 7.48 (d, J = 8.0 Hz, 1H), 7.36 (d, J = 2.0 Hz, 1H), 7.31 (d, J = 0.8 Hz, 1H), 4.64 (brs, 0.5H), 4.31-4.28 (m, 1H), 3.92-3.80 (m, 2.5H), 3.55-3.47 (m, 4.5H), 2.93-2.71 (m, 3.5H), 2.64 (s, 3H), 2.31 (s, 3H), 2.25-1.90 (m, 3H), 1.72-1.67 (m, 3H), 1.39-1.23 (m, 3H). MS (ESI): C₂₆H₃₃ClN₄O₃ requires 484; found 485 [M + H]⁺. |
| E54 & E55 | | DMF/DIPEA | Isomer 1: ¹H NMR (400 MHz, MeOD-d₄): 9.02 (d, J = 2.0 Hz, 1H), 8.29 (dd, J = 8.4 Hz, 2.4 Hz, 1H), 7.49 (d, J = 8.0 Hz, 1H), 7.37 (d, J = 2.4 Hz, 1H), 7.32 (d, J = 2.0 Hz, 1H), 4.65 (brs, 0.5H), 4.36-4.28 (m, 1H), 4.20-4.19 (m, 1H), 4.00-3.97 (m, 1H), 3.83-3.79 (m, 0.5H), 3.55-3.52 (m, 3H), 3.39-3.35 (m, 0.5H), 3.04-2.97 (m, 0.5H), 2.87-2.84 (m, 1H), 2.76-2.73 (m, 1H), 2.65 (s, 3H), 2.32 (s, 3H), 2.29-1.93 (m, 3H), 1.70-1.57 (m, 5H), 1.40-1.25 (m, 3H). MS (ESI): C₂₆H₃₃ClN₄O₃ requires 484; found 485 [M + H]⁺. Isomer 2: ¹H NMR (400 MHz, MeOD-d₄): 9.02 (d, J = 2.0 Hz, 1H), 8.29 (dd, J = 8.4 Hz, 2.4 Hz, 1H), 7.49 (d, J = 8.0 Hz, 1H), 7.37 (d, J = 2.0 Hz, 1H), 7.32 (d, J = 2.0 Hz, 1H), 4.65 (brs, 0.5H), 4.36-4.28 (m, 1H), 4.20-4.18 (m, 1H), 3.99-3.98 (m, 1H), 3.83-3.79 (m, 0.5H), 3.57-3.53 (m, 3H), 3.39-3.35 (m, 0.5H), 3.04-2.97 (m, 0.5H), 2.86-2.80 (m, 1H), 2.77-2.75 (m, 1H), 2.65 (s, 3H), 2.33 (s, 3H), 2.29-1.93 (m, 3H), 1.72-1.58 (m, 5H), 1.40-1.25 (m, 3H). MS (ESI): C₂₆H₃₃ClN₄O₃ requires 484; found 485 [M + H]⁺. |

Example 56&57

N-(5-chloro-2-methyl-3-(((S)-3-methyl-4-((R)-tetrahydrofuran-3-carbonyl)piperazin-1-yl)methyl)phenyl)-5-fluoro-6-methylnicotinamide (E56)

N-(5-chloro-2-methyl-3-(((S)-3-methyl-4-((S)-tetrahydrofuran-3-carbonyl)piperazin-1-yl)methyl)phenyl)-5-fluoro-6-methylnicotinamide (E57)

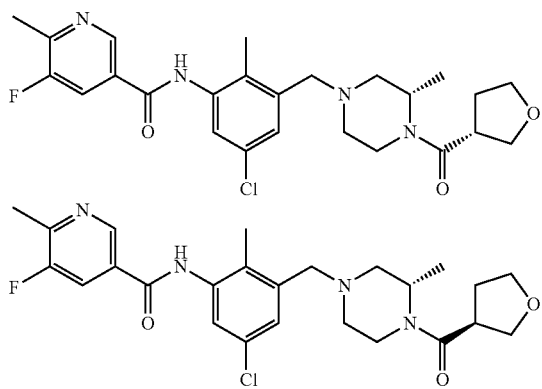

A mixture of HATU (438 mg), DIPEA (0.402 mL), (S)—N-(5-chloro-2-methyl-3-((3-methylpiperazin-1-yl)methyl)phenyl)-5-fluoro-6-methylnicotinamide (D55, 300 mg) and tetrahydrofuran-3-carboxylic acid (89 mg) in DCM (150 mL) was stirred at RT overnight. The mixture was concentrated in vacuo and purified by preparative HPLC to afford the crude product (260 mg), which was separated by chiral HPLC to afford the title compounds (E56 (55 mg) and E57 (50 mg)) as white solids. E56: chiral SFC: column: OJ-H, 4.6×250 mm, 5 um; co-solvent: MeOH (containing 0.1% DEA); column temperature: 36.7° C.; $CO_2$ flow rate: 2.4 mL/min; co-solvent flow rate: 0.6 mL/min; co-solvent: 20%; $t_R$=7.40 min. $^1$H NMR (400 MHz, MeOD-$d_4$): 8.88 (s, 1H), 8.08 (d, J=9.6 Hz, 1H), 7.37 (d, J=2.0 Hz, 1H), 7.32 (s, 1H), 4.68 (brs, 0.5H), 4.34-4.31 (m, 0.5H), 4.25 (brs, 0.5H), 4.04-3.99 (m, 0.5H), 3.96-3.77 (m, 4H), 3.56-3.36 (m, 3.5H), 3.05-2.97 (m, 0.5H), 2.88-2.83 (m, 1H), 2.80-2.75 (m, 1H), 2.61 (brs, 3H), 2.32 (s, 3H), 2.24-2.00 (m, 4H), 1.32-1.28 (m, 3H). $^{19}$F NMR (376 MHz, MeOD-$d_4$): −125.4. MS (ESI): $C_{25}H_{30}ClFN_4O_3$ requires 488; found 489 [M+H]$^+$. E57: chiral SFC: column: OJ-H, 4.6×250 mm, 5 um; co-solvent: MeOH (containing 0.1% DEA); column temperature: 40° C.; $CO_2$ flow rate: 2.4 mL/min; co-solvent flow rate: 0.6 mL/min; co-solvent: 20%; $t_R$=8.51 min. $^1$H NMR (400 MHz, MeOD-$d_4$): 8.88 (s, 1H), 8.08 (d, J=9.6 Hz, 1H), 7.37 (d, J=2.0 Hz, 1H), 7.32 (s, 1H), 4.67 (brs, 0.5H), 4.34-4.31 (m, 1H), 3.98-3.78 (m, 4.5H), 3.53-3.48 (m, 2H), 3.43-3.41 (m, 1.5H), 2.99-2.85 (m, 0.5H), 2.88-2.85 (m, 1H), 2.80-2.75 (m, 1H), 2.61 (brs, 3H), 2.32 (s, 3H), 2.24-2.00 (m, 4H), 1.32-1.28 (m, 3H). $^{19}$F NMR (376 MHz, MeOD-$d_4$): −125.4. MS (ESI): $C_{25}H_{30}ClFN_4O_3$ requires 488; found 489 [M+H]$^+$.

Example 58

N-(5-chloro-2-methyl-3-(((S)-3-methyl-4-((R)-tetrahydrofuran-2-carbonyl)piperazin-1-yl)methyl)phenyl)-3-fluorobenzamide (E58)

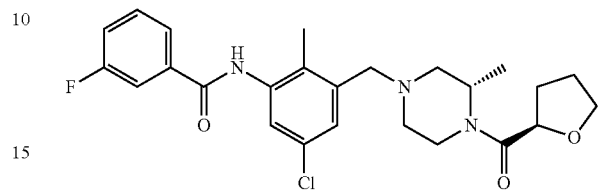

To a mixture of ((S)-4-(3-amino-5-chloro-2-methylbenzyl)-2-methylpiperazin-1-yl)((R)-tetrahydrofuran-2-yl)methanone (D75, 100 mg), DMAP (38.2 mg) in DCM (10 mL) was added 3-fluorobenzoyl chloride (45.1 mg) slowly. The mixture was stirred at 20° C. for 16 hours. The solvent was removed. The residue was purified by preparative HPLC to give the title compound (63 mg) as a white solid. $^1$H NMR (400 MHz, MeOD-$d_4$): 7.83-7.81 (d, J=8.4 Hz, 1H), 7.74-7.71 (d, J=12.0 Hz, 1H), 7.60-7.55 (m, 1H), 7.40-7.32 (m, 3H), 4.74-4.70 (m, 1H), 4.66-4.64 (m, 0.5H), 4.31-4.28 (brs, 0.5H), 4.25-4.15 (m, 0.5H), 4.00-3.82 (m, 2.5H), 3.56-3.48 (m, 2H), 3.39-3.33 (m, 0.5H), 3.06-2.99 (m, 0.5H), 2.89-2.78 (m, 1H), 2.77-2.74 (m, 1H), 2.32 (s, 3H), 2.27-1.94 (m, 6H), 1.40-1.25 (m, 3H). MS (ESI): $C_{25}H_{29}ClFN_3O_3$ requires 473; found 474 [M+H]$^+$.

Example 59-65

Examples 59-65 was prepared using a similar procedure to that described for Example 58.

E59: N-(5-chloro-2-methyl-3-(((S)-3-methyl-4-((S)-tetrahydrofuran-2-carbonyl)piperazin-1-yl)methyl)phenyl)-3-fluorobenzamide E60: 3-chloro-N-(5-chloro-2-methyl-3-(((S)-3-methyl-4-((S)-tetrahydrofuran-2-carbonyl)piperazin-1-yl)methyl)phenyl)benzamide E61: N-(5-chloro-2-methyl-3-(((S)-3-methyl-4-((R)-tetrahydrofuran-2-carbonyl)piperazin-1-yl)methyl)phenyl)-3-fluoro-4-methylbenzamide E62: N-(5-chloro-2-methyl-3-(((S)-3-methyl-4-((S)-tetrahydrofuran-2-carbonyl)piperazin-1-yl)methyl)phenyl)-3-fluoro-4-methylbenzamide E63: N-(5-chloro-2-methyl-3-(((S)-3-methyl-4-((S)-tetrahydrofuran-2-carbonyl)piperazin-1-yl)methyl)phenyl)-3,5-difluorobenzamide E64: N-(5-chloro-2-methyl-3-(((S)-3-methyl-4-((R)-tetrahydrofuran-2-carbonyl)piperazin-1-yl)methyl)phenyl)-3,5-difluorobenzamide E65: 3-chloro-N-(5-chloro-2-methyl-3-(((S)-3-methyl-4-((R)-tetrahydrofuran-2-carbonyl)piperazin-1-yl)methyl)phenyl)benzamide

| | Structure | Characterization |
|---|---|---|
| E59 | 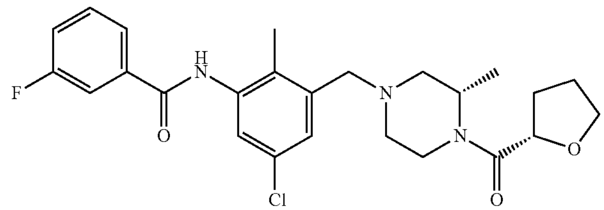 [SMILES: Cc1c(CN2CCN(C(=O)[C@@H]3CCCO3)[C@@H](C)C2)cc(Cl)cc1NC(=O)c1cccc(F)c1] | $^1$H NMR (400 MHz, MeOD-d$_4$): 7.70 (d, J = 8.4 Hz, 1H), 7.62-7.59 (m, 1H), 7.58-7.52 (m, 1H), 7.27-7.18 (m, 3H), 4.70-4.61 (m, 1.5H), 4.35-4.25 (m, 1H), 3.80-3.63 (m, 2.5H), 3.53-3.39 (m, 2H), 3.39-3.31 (m, 0.5H), 3.03-2.95 (m, 0.5H), 2.84-2.76 (m, 1H), 2.73-2.68 (m, 1H), 2.19 (s, 3H), 2.20-1.83 (m, 6H), 1.35-1.14 (m, 3H). MS (ESI): C$_{25}$H$_{29}$ClFN$_3$O$_3$ requires 473; found 474 [M + H]$^+$. |
| E60 | 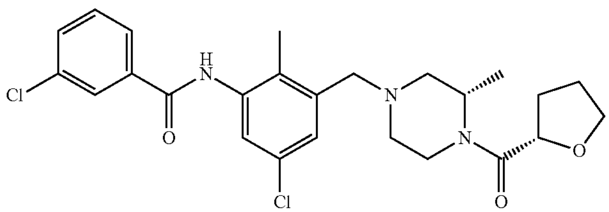 [SMILES: Cc1c(CN2CCN(C(=O)[C@@H]3CCCO3)[C@@H](C)C2)cc(Cl)cc1NC(=O)c1cccc(Cl)c1] | $^1$H NMR (400 MHz, MeOD-d$_4$): 7.99 (s, 1H), 7.91 (d, J = 8.0 Hz, 1H), 7.63-7.61 (m, 1H), 7.53 (t, J = 8.0 Hz, 1H), 7.34 (d, J = 2.0 Hz, 1H), 7.30 (d, J = 2.0 Hz, 1H), 4.81-4.65 (m, 1.5H), 4.32-4.28 (m, 1H), 3.96-3.92 (m, 1H), 3.87-3.81 (m, 1H), 3.78-3.74 (m, 0.5H), 3.55-3.46 (m, 2H), 3.42-3.37 (m, 0.5H), 3.04-2.98 (m, 0.5H), 2.87-2.83 (m, 1H), 2.75-2.73 (m, 1H), 2.30 (s, 3H), 2.25-1.89 (m, 6H), 1.38-1.25 (m, 3H). MS (ESI): C$_{25}$H$_{29}$Cl$_2$N$_3$O$_3$ requires 489; found 490 [M + H]$^+$. |
| E61 | 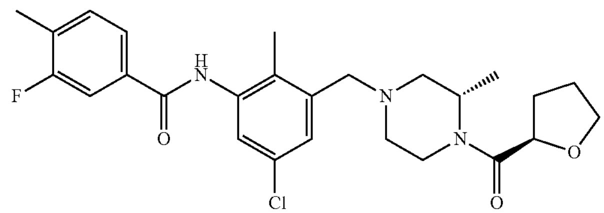 [SMILES: Cc1ccc(C(=O)Nc2cc(Cl)cc(CN3CCN(C(=O)[C@H]4CCCO4)[C@@H](C)C3)c2C)cc1F] | $^1$H NMR (400 MHz, MeOD-d$_4$): 7.72-7.64 (m, 2H), 7.40 (t, J = 8.4 Hz, 1H), 7.32-7.29 (m, 2H), 4.86-4.63 (m, 1.5H), 4.29-4.17 (m, 1H), 3.98-3.80 (m, 2.5H), 3.54-3.46 (m, 2H), 3.37-3.31 (m, 0.5H), 3.04-2.97 (m, 0.5H), 2.87-2.72 (m, 2H), 2.36 (s, 3H), 2.29 (s, 3H), 2.25-1.92 (m, 6H), 1.37-1.23 (m, 3H). MS (ESI): C$_{26}$H$_{31}$ClFN$_3$O$_3$ requires 487; found 488 [M + H]$^+$. |
| E62 | 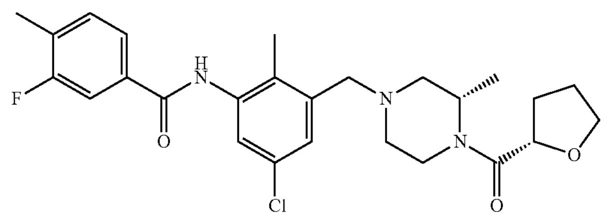 [SMILES: Cc1ccc(C(=O)Nc2cc(Cl)cc(CN3CCN(C(=O)[C@@H]4CCCO4)[C@@H](C)C3)c2C)cc1F] | $^1$H NMR (400 MHz, MeOD-d$_4$): 7.74-7.66 (m, 2H), 7.45-7.40 (m, 1H), 7.35-7.31 (d, J = 9.0 Hz, 2H), 4.76-4.63 (m, 1.5H), 4.39-4.27 (m, 1H), 3.98-3.70 (m, 2.5H), 3.54-3.46 (m, 2H), 3.37-3.31 (m, 0.5H), 3.04-2.97 (m, 0.5H), 2.95-2.72 (m, 2H), 2.36 (s, 3H), 2.29 (s, 3H), 2.25-1.92 (m, 6H), 1.40-1.17 (m, 3H). MS (ESI): C$_{26}$H$_{31}$ClFN$_3$O$_3$ requires 487; found 488 [M + H]$^+$. |
| E63 | 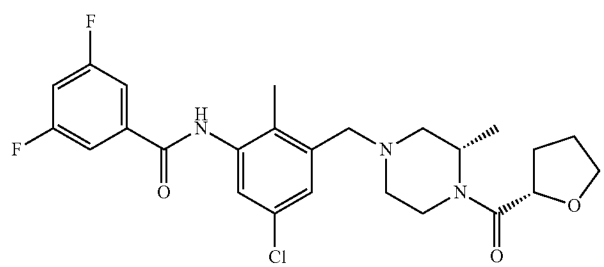 [SMILES: Cc1c(CN2CCN(C(=O)[C@@H]3CCCO3)[C@@H](C)C2)cc(Cl)cc1NC(=O)c1cc(F)cc(F)c1] | $^1$H NMR (400 MHz, MeOD-d$_4$): 7.61 (dd, J = 12.4 Hz, 6.8 Hz, 2H), 7.34 (d, J = 2.4 Hz, 1H), 7.32 (d, J = 2.4 Hz, 1H), 7.28-7.23 (m, 1H), 4.74-4.66 (m, 1.5H), 4.33-4.29 (m, 1H), 3.96-3.93 (m, 1H), 3.87-3.82 (m, 1H), 3.79-3.75 (m, 0.5H), 3.55-3.45 (m, 2H), 3.48-3.37 (m, 0.5H), 3.05-2.98 (m, 0.5H), 2.86-2.83 (m, 1H), 2.73 (d, J = 8.0 Hz, 1H), 2.30 (s, 3H), 2.27-1.92 (m, 6H), 1.38-1.27 (m, 3H). MS (ESI): C$_{25}$H$_{28}$ClF$_2$N$_3$O$_3$ requires 491; found 492 [M + H]$^+$. |
| E64 | 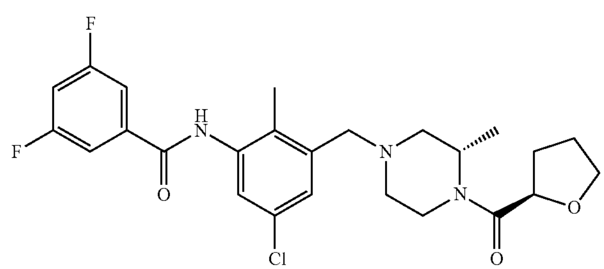 [SMILES: Cc1c(CN2CCN(C(=O)[C@H]3CCCO3)[C@@H](C)C2)cc(Cl)cc1NC(=O)c1cc(F)cc(F)c1] | $^1$H NMR (400 MHz, MeOD-d$_4$): 7.63-7.60 (m, 2H), 7.34-7.31 (m, 2H), 7.28-7.23 (m, 1H), 4.74-4.69 (m, 1H), 4.64 (brs, 0.5H), 4.30-4.28 (m, 0.5H), 4.18 (brs, 0.5H), 3.97-3.94 (m, 1H), 3.88-3.83 (m, 1.5H), 3.53-4.97 (m, 2H), 3.35-3.34 (m, 0.5H), 3.03-2.97 (m, 0.5H), 2.87-2.81 (m, 1H), 2.75-2.73 (m, 1H), 2.30 (s, 3H), 2.26-1.90 (m, 6H), 1.38-1.25 (m, 3H). MS (ESI): C$_{25}$H$_{28}$ClF$_2$N$_3$O$_3$ requires 491; found 492 [M + H]$^+$. |
| E65 | 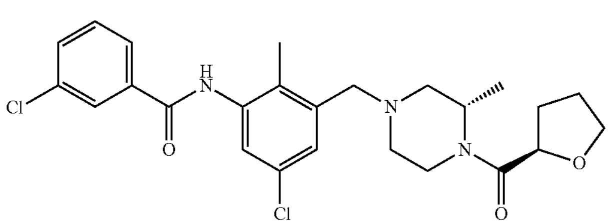 [SMILES: Cc1c(CN2CCN(C(=O)[C@H]3CCCO3)[C@@H](C)C2)cc(Cl)cc1NC(=O)c1cccc(Cl)c1] | $^1$H NMR (400 MHz, MeOD-d$_4$): 7.99 (s, 1H), 7.91 (d, J = 7.8 Hz, 1H), 7.65-7.60 (m, 1H), 7.53 (t, J = 8.0 Hz, 1H), 7.34 (d, J = 1.5 Hz, 1H), 7.32-7.27 (m, 1H), 4.75-4.68 (m, 1H), 4.67-4.58 (m, 0.5H), 4.28 (d, J = 13.5 Hz, 0.5H), 4.22-4.14 (m, 0.5H), 4.00-3.90 (m, 1H), 3.89-3.77 (m, 1.5H), 3.56-3.45 (m, 2H), 3.39-3.33 (m, 0.5H), 3.06-2.96 (m, 0.5H), 2.89-2.79 (m, 1H), 2.74 (d, J = 11.3 Hz, 1H), 2.30 (s, 3H), 2.27-1.87 (m, 6H), 1.41-1.21 (m, 3H). MS (ESI): C$_{25}$H$_{29}$Cl$_2$N$_3$O$_3$ requires 489; found 490 [M + H]$^+$. |

Example 66

N-(5-chloro-2-methyl-3-(((S)-3-methyl-4-((R)-tetrahydrofuran-2-carbonyl)piperazin-1-yl)methyl)phenyl)-3-fluoro-5-methylbenzamide (E66)

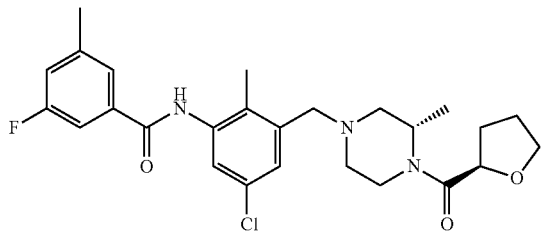 [SMILES: Cc1cc(F)cc(C(=O)Nc2cc(Cl)cc(CN3CCN(C(=O)[C@H]4CCCO4)[C@@H](C)C3)c2C)c1]

A mixture of 3-fluoro-5-methylbenzoic acid (65.7 mg) in sulfurous dichloride (338 mg) was stirred at 80° C. for 1 hour. The mixture was then concentrated in vacuo. The residue was added into a mixture of ((S)-4-(3-amino-5-chloro-2-methylbenzyl)-2-methylpiperazin-1-yl)((R)-tetrahydrofuran-2-yl)methanone (D75, 100 mg), DMAP (38.2 mg) in DCM (8 mL). The mixture was stirred at 20° C. for 16 hours, and then concentrated. The residue was purified by preparative HPLC and chiral HPLC to give the title compound (5 mg) as a white solid. $^1$H NMR (400 MHz, MeOD-d$_4$): 7.66 (s, 1H), 7.50 (d, J=9.6 Hz, 1H), 7.35-7.31 (m, 2H), 7.21 (d, J=9.0 Hz, 1H), 4.76-4.63 (m, 1.5H), 4.40-4.30 (m, 1H), 3.98-3.70 (m, 2.5H), 3.54-3.46 (m, 2H), 3.37-3.31 (m, 0.5H), 3.04-2.97 (m, 0.5H), 2.95-2.73 (m, 2H), 2.46 (s, 3H), 2.29 (s, 3H), 2.25-1.90 (m, 6H), 1.41-1.17 (m, 3H). MS (ESI): $C_{26}H_{31}ClFN_3O_3$ requires 487; found 488 [M+H]$^+$.

Example 67

N-(5-chloro-2-methyl-3-(((S)-3-methyl-4-((S)-tetrahydrofuran-2-carbonyl)piperazin-1-yl)methyl)phenyl)-3-fluoro-5-methylbenzamide (E67)

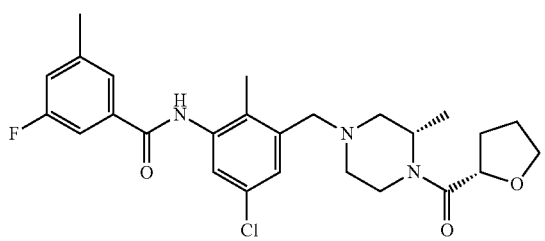 [SMILES: Cc1cc(F)cc(C(=O)Nc2cc(Cl)cc(CN3CCN(C(=O)[C@@H]4CCCO4)[C@@H](C)C3)c2C)c1]

Example 67 was prepared using a similar procedure to that described for Example 66. $^1$H NMR (400 MHz, MeOD-d$_4$): 7.65 (s, 1H), 7.50 (d, J=9.6 Hz, 1H), 7.32 (d, J=9.6 Hz, 2H), 7.21 (d, J=9.0 Hz, 1H), 4.76-4.60 (m, 1.5H), 4.39-4.27 (m, 1H), 3.98-3.70 (m, 2.5H), 3.54-3.46 (m, 2H), 3.37-3.31 (m, 0.5H), 3.04-2.96 (m, 0.5H), 2.87-2.62 (m, 2H), 2.46 (s, 3H), 2.29 (s, 3H), 2.25-1.88 (m, 6H), 1.37-1.13 (m, 3H). MS (ESI): $C_{26}H_{31}ClFN_3O_3$ requires 487; found 488 [M+H]$^+$.

Example 68

N-(5-chloro-2-methyl-3-(((S)-3-methyl-4-((R)-tetrahydrofuran-2-carbonyl)piperazin-1-yl)methyl)phenyl)-5,6-dimethylnicotinamide (E68)

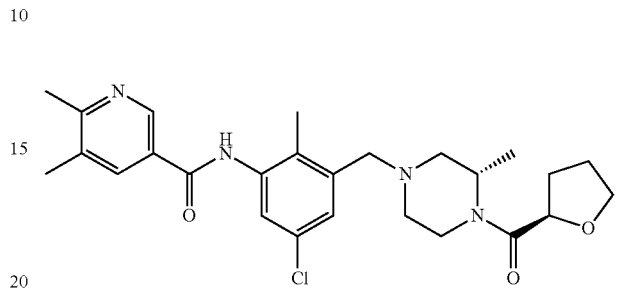

To a solution of 5,6-dimethylnicotinic acid (D3, 55 mg) and one drop of DMF in DCM (5 mL) was added oxalyl chloride (0.080 mL) dropwise under a nitrogen atmosphere. The mixture was stirred at RT for 1 hour, and then concentrated under reduced pressure. The residue was dissolved in DCM (5 mL), to which ((S)-4-(3-amino-5-chloro-2-methylbenzyl)-2-methylpiperazin-1-yl)((R)-tetrahydrofuran-2-yl)methanone (D75, 128 mg) and DIPEA (0.191 mL) were added. The resulting mixture was stirred at RT for 3 hours, and then concentrated in vacuo. The crude product was purified by preparative TLC (eluting with PE:EA=1:3) to give an oil. The oil was purified by preparative HPLC to afford the title compound (20 mg) as a white solid. $^1$H NMR (400 MHz, MeOD-d$_4$): 8.84 (s, 1H), 8.14 (s, 1H), 7.36 (s, 1H), 7.32 (d, J=1.6 Hz, 1H), 4.75-4.70 (m, 1H), 4.69-4.62 (m, 0.5H), 4.33-4.26 (d, 0.5H), 4.22-4.18 (m, 0.5H), 3.98-3.94 (m, 1H), 3.89-3.82 (m, 1.5H), 3.56-3.49 (m, 2H), 3.36-3.34 (m, 0.5H), 3.03-2.98 (m, 0.5H), 2.90-2.84 (m, 1H), 2.77-2.74 (m, 1H), 2.61 (s, 3H), 2.44 (s, 3H), 2.32 (s, 3H), 2.29-1.94 (m, 6H), 1.40-1.25 (m, 3H). MS (ESI): $C_{26}H_{33}ClN_4O_3$ requires 484; found 485 [M+H]$^+$.

Example 69-72

Examples 69-72 were prepared using a similar procedure to that described for Example 68, with the specified reaction base listed in the table.

E69: N-(5-fluoro-2-methyl-3-(((S)-3-methyl-4-((R)-tetrahydrofuran-2-carbonyl)piperazin-1-yl)methyl)phenyl)-5,6-dimethylnicotinamide E70: N-(5-chloro-3-(((S)-3-ethyl-4-((R)-tetrahydrofuran-2-carbonyl)piperazin-1-yl)methyl)-2-methylphenyl)-5-fluoro-6-methylnicotinamide E71: 5-chloro-N-(5-chloro-2-methyl-3-(((S)-3-methyl-4-((R)-tetrahydrofuran-2-carbonyl)piperazin-1-yl)methyl)phenyl)nicotinamide, trifluoroacetic acid salt E72: 5-fluoro-N-(5-fluoro-2-methyl-3-(((S)-3-methyl-4-((R)-tetrahydrofuran-2-carbonyl)piperazin-1-yl)methyl)phenyl)-6-methylnicotinamide

| | Structure | base | Characterization |
|---|---|---|---|
| E69 | 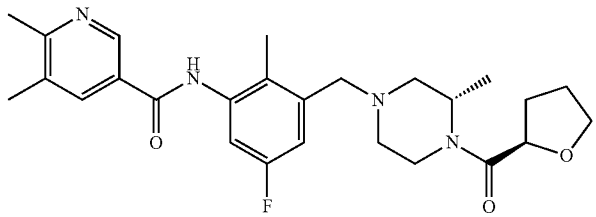 [SMILES: Cc1cc(C(=O)Nc2cc(F)cc(CN3CCN(C(=O)[C@H]4CCCO4)[C@@H](C)C3)c2C)cnc1C] | DIPEA | $^1$H NMR (400 MHz, MeOD-$d_4$): 8.84 (s, 1H), 8.14 (s, 1H), 7.14-7.09 (m, 2H), 4.75-4.70 (m, 1H), 4.69-4.62 (m, 0.5H), 4.32-4.26 (m, 0.5H), 4.20 (brs, 0.5H), 4.00-3.94 (m, 1H), 3.89-3.82 (m, 1.5H), 3.57-3.50 (m, 2H), 3.40-3.36 (m, 0.5H), 3.07-3.01 (m, 0.5H), 2.91-2.83 (m, 1H), 2.78-2.75 (m, 1H), 2.61 (s, 3H), 2.44 (s, 3H), 2.31 (s, 3H), 2.04-1.93 (m, 6H), 1.41-1.26 (m, 3H). MS (ESI): $C_{26}H_{33}FN_4O_3$ requires 468; found 469 $[M + H]^+$. |
| E70 | 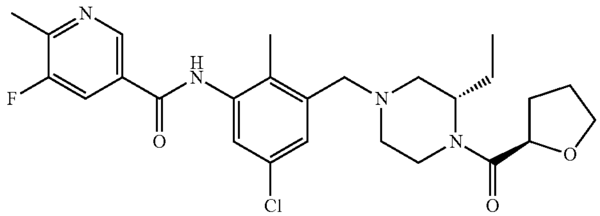 [SMILES: CC[C@H]1CN(Cc2cc(Cl)cc(NC(=O)c3cnc(C)c(F)c3)c2C)CCN1C(=O)[C@H]1CCCO1] | DIPEA | $^1$H NMR (400 MHz, MeOD-$d_4$): 8.89 (s, 1H), 8.09 (dd, J = 10.0 Hz, 1.6 Hz, 1H), 7.37 (d, J = 1.6 Hz, 1H), 7.32 (d, J = 2.0 Hz, 1H), 4.78-4.74 (m, 1H), 4.45-4.32 (m, 1H), 4.00-3.94 (m, 1H), 3.90-3.82 (m, 2H), 3.57-3.47 (m, 2H), 3.31-3.27 (m, 0.5H), 2.99-2.91 (m, 0.5H), 2.88-2.81 (m, 2H), 2.62 (d, J = 3.2 Hz, 3H), 2.31 (d, J = 1.6 Hz, 3H), 2.28-1.70 (m, 8H), 0.89-0.80 (m, 3H). MS (ESI): $C_{26}H_{32}ClFN_4O_3$ requires 502; found 503 $[M + H]^+$. |
| E71 | 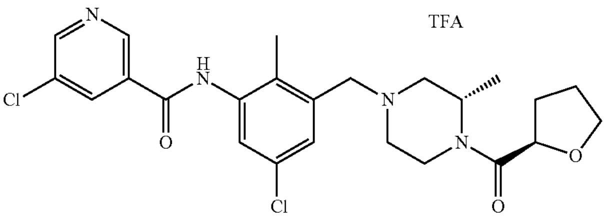 [SMILES: Cc1c(CN2CCN(C(=O)[C@H]3CCCO3)[C@@H](C)C2)cc(Cl)cc1NC(=O)c1cncc(Cl)c1] | TEA | $^1$H NMR (400 MHz, MeOD-$d_4$): 9.06 (d, J = 1.6 Hz, 1H), 8.81 (d, J = 2.0 Hz, 1H), 8.43 (t, J = 2.2 Hz, 1H), 7.56 (s, 2H), 4.80-4.66 (m, 1.5H), 4.57-4.56 (m, 1H), 4.30-4.19 (m, 2.5H), 3.96-3.92 (m, 1H), 3.90-3.84 (m, 1H), 3.53-4.98 (m, 0.5H), 3.38-3.34 (m, 1H), 3.17-2.66 (m, 3H), 2.35 (s, 3H), 2.19-1.92 (m, 4.5H), 1.46-1.31 (m, 3H). $^{19}$F NMR (376 MHz, MeOD-$d_4$): −77.24. MS (ESI): $C_{24}H_{28}Cl_2N_4O_3$ requires 490; found 491 $[M + H]^+$. |
| E72 | 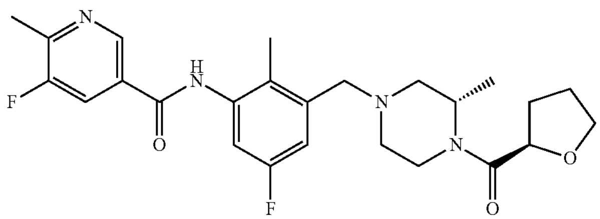 [SMILES: Cc1ncc(C(=O)Nc2cc(F)cc(CN3CCN(C(=O)[C@H]4CCCO4)[C@@H](C)C3)c2C)cc1F] | DIPEA | $^1$H NMR (400 MHz, MeOD-$d_4$): 8.89 (s, 1H), 8.09 (d, J = 10.4 Hz, 1H), 7.15-7.10 (m, 2H), 4.75-4.70 (m, 1H), 4.69-4.62 (m, 0.5H), 4.33-4.26 (m, 0.5H), 4.20 (brs, 0.5H), 4.00-3.94 (m, 1H), 3.89-3.82 (m, 1.5H), 3.57-3.50 (m, 2H), 3.42-3.36 (m, 0.5H), 3.06-3.01 (m, 0.5H), 2.90-2.84 (m, 1H), 2.78-2.75 (m, 1H), 2.62 (d, J = 2.8 Hz, 3H), 2.31 (s, 3H), 2.28-1.93 (m, 6H), 1.41-1.26 (m, 3H). MS (ESI): $C_{25}H_{30}F_2N_4O_3$ requires 472; found 473 $[M + H]^+$. |

Example 73&74

N-(5-chloro-2-methyl-3-(((S)-3-methyl-4-((R)-tetrahydrofuran-3-carbonyl)piperazin-1-yl)methyl)phenyl)-5,6-dimethylnicotinamide & N-(5-chloro-2-methyl-3-(((S)-3-methyl-4-((S)-tetrahydrofuran-3-carbonyl)piperazin-1-yl)methyl)phenyl)-5,6-dimethylnicotinamide (E73&E74)

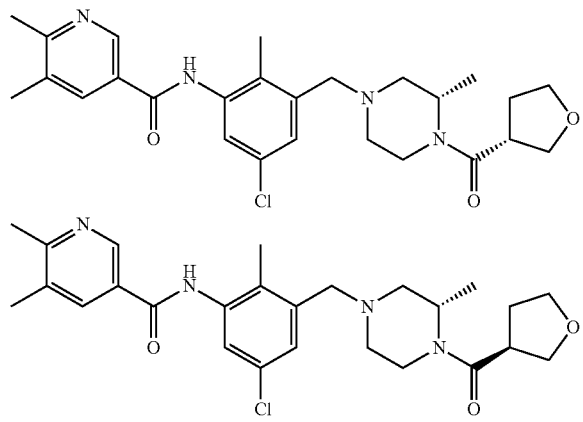

A mixture of 5,6-dimethylnicotinic acid (D3, 0.129 g) in oxalyl dichloride (3.07 mL) was stirred at RT for 1 hour. The mixture was concentrated under vacuum. The residue was added into a mixture of ((S)-4-(3-amino-5-chloro-2-methylbenzyl)-2-methylpiperazin-1-yl)(tetrahydrofuran-3-yl)methanone (D76, 200 mg) and DIPEA (0.147 g) in DCM (20 mL). The mixture was stirred at 20° C. for 16 hours, and then concentrated. The resulting mixture was purified by preparative HPLC and chiral HPLC to afford the title compounds (10 mg and 8 mg) as white solids. Isomer 1: $^1$H NMR (400 MHz, MeOD-$d_4$): 8.82 (d, J=2.0 Hz, 1H), 8.12 (d, J=1.2 Hz, 1H), 7.35 (d, J=2.4 Hz, 1H), 7.30 (d, J=2.0 Hz, 1H), 4.67 (brs, 0.5H), 4.33-4.24 (m, 1H), 4.04-4.00 (0.5H), 3.95-3.76 (m, 4H), 3.55-3.34 (m, 3.5H), 3.03-2.96 (m, 0.5H), 2.86 (d, J=11.6 Hz, 1H), 2.77-2.72 (m, 1H), 2.59 (s, 3H), 2.42 (s, 3H), 2.31 (s, 3H), 2.24-1.98 (m, 4H), 1.38-1.23 (m, 3H). MS (ESI): $C_{26}H_{33}ClN_4O_3$ requires 484; found 485 $[M+H]^+$. Isomer 2: $^1$H NMR (400 MHz, MeOD-$d_4$): 8.82 (d, J=1.6 Hz, 1H), 8.12 (d, J=1.2 Hz, 1H), 7.35 (d, J=2.0 Hz, 1H), 7.31 (s, 1H), 4.66 (brs, 0.5H), 4.34-4.30 (m, 1H), 3.97-3.75 (m, 4.5H), 3.56-3.37 (m, 3.5H), 3.03-2.95 (m, 0.5H), 2.86 (d, J=11.6 Hz, 1H), 2.78-2.72 (m, 1H), 2.59 (s, 3H), 2.42 (s, 3H), 2.31 (s, 3H), 2.26-1.98 (m, 4H), 1.36-1.24 (m, 3H). MS (ESI): $C_{26}H_{33}ClN_4O_3$ requires 484; found 485 $[M+H]^+$.

Example 75&76

5-chloro-N-(5-fluoro-2-methyl-3-(((S)-3-methyl-4-((S)-tetrahydrofuran-3-carbonyl)piperazin-1-yl)methyl)phenyl)-6-methylnicotinamide & 5-chloro-N-(5-fluoro-2-methyl-3-(((S)-3-methyl-4-((R)-tetrahydrofuran-3-carbonyl)piperazin-1-yl)methyl)phenyl)-6-methylnicotinamide (E75&E76)

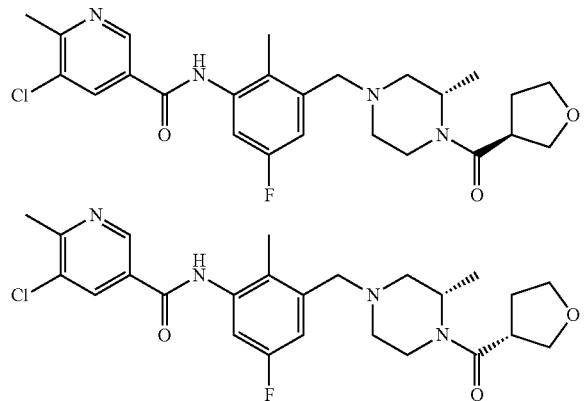

To a solution of 5-chloro-6-methylnicotinic acid (D5, 400 mg) in DCM (2 mL) was added oxalyl chloride (0.612 mL) carefully. The mixture was stirred for 0.5 hour, and then concentrated to afford 5-chloro-6-methylnicotinoyl chloride (500 mg). Part of the residue (113 mg) was added to a solution of ((S)-4-(3-amino-5-fluoro-2-methylbenzyl)-2-methylpiperazin-1-yl)(tetrahydrofuran-3-yl)methanone (D80, 200 mg) and DMAP (219 mg) in DCM (3 mL). The mixture was stirred for 2 hours, and then filtered. After concentration, water was added. The resulting mixture was extracted with EA. The organic phase was dried, concentrated and purified by preparative HPLC to afford the title compounds (6 mg and 12 mg). Isomer 1: $^1$H NMR (400 MHz, MeOD-d$_4$): 8.94 (d, J=1.2 Hz, 1H), 8.36 (d, J=1.6 Hz, 1H), 7.14-7.08 (m, 2H), 4.67 (m, 0.5H), 4.33-4.24 (m, 1H), 4.04-4.00 (m, 0.5H), 3.95-3.76 (m, 4H), 3.56-3.35 (m, 3.5H), 3.04-2.97 (m, 0.5H), 2.87 (d, J=11.2 Hz, 1H), 2.78-2.73 (m, 1H), 2.70 (s, 3H), 2.29 (s, 3H), 2.25-1.98 (m, 4H), 1.39-1.24 (m, 3H). MS (ESI): C$_{25}$H$_{30}$ClFN$_4$O$_3$ requires 488; found 489 [M+H]$^+$. Isomer 2: $^1$H NMR (400 MHz, MeOD-d$_4$): 8.94 (d, J=1.2 Hz, 1H), 8.36 (d, J=1.2 Hz, 1H), 7.14-7.08 (m, 2H), 4.66 (m, 0.5H), 4.33-4.31 (m, 1H), 3.97-3.75 (m, 4.5H), 3.56-3.37 (m, 3.5H), 3.03-2.95 (m, 0.5H), 2.87 (d, J=11.6 Hz, 1H), 2.79-2.73 (m, 1H), 2.70 (s, 3H), 2.29 (s, 3H), 2.27-1.98 (m, 4H), 1.37-1.24 (m, 3H). MS (ESI): C$_{25}$H$_{30}$ClFN$_4$O$_3$ requires 488; found 489 [M+H]$^+$.

Example 77

(S)—N-(5-chloro-2-methyl-3-((3-methyl-4-(tetrahydro-2H-pyran-4-carbonyl)piperazin-1-yl)methyl)phenyl)-6-cyanonicotinamide (E77)

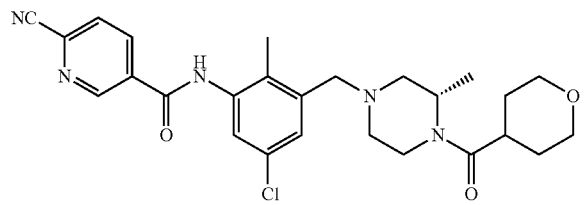 [SMILES: Cc1c(CN2CCN(C(=O)C3CCOCC3)[C@@H](C)C2)cc(Cl)cc1NC(=O)c1ccc(C#N)nc1]

To a solution of (S)-(4-(3-amino-5-chloro-2-methylbenzyl)-2-methylpiperazin-1-yl)(tetrahydro-2H-pyran-4-yl)methanone (D81, 112.7 mg) and 6-cyanonicotinic acid (51.7 mg) in anhydrous DMF (5 mL) were added HATU (178.7 mg) and DIPEA (0.161 mL). The mixture was stirred at RT overnight, and purified by MDAP (basic condition, ACN/H$_2$O (containing 0.05% NH$_3$H$_2$O), ACN %=30%-80%) to afford the title compound (40.7 mg) as an off-white solid. $^1$H NMR (400 MHz, MeOD-d$_4$): 9.23 (s, 1H), 8.50 (dd, J=8.1 Hz, 1.7 Hz, 1H), 8.04 (d, J=8.1 Hz, 1H), 7.39 (d, J=1.7 Hz, 1H), 7.32 (d, J=1.7 Hz, 1H), 4.72-4.54 (m, 1H), 4.37-4.22 (m, 1H), 4.01-3.90 (m, 2H), 3.84 (d, J=13.0 Hz, 0.5H), 3.58-3.44 (m, 4.5H), 3.44-3.36 (m, 0.5H), 3.03-2.82 (m, 2.5H), 2.80-2.68 (m, 1H), 2.32 (s, 3H), 2.28-1.95 (m, 2H), 1.93-1.50 (m, 4H), 1.42-1.17 (m, 3H). MS (ESI): C$_{26}$H$_{30}$ClN$_5$O$_3$ requires 495; found 496 [M+H]$^+$.

Example 78-87

Examples 78-87 were prepared using a similar procedure to that described for Example 77.

E78: (S)—N-(5-chloro-2-methyl-3-((3-methyl-4-(tetrahydro-2H-pyran-4-carbonyl)piperazin-1-yl)methyl)phenyl)-2-cyanoisonicotinamide E79: (S)—N-(5-chloro-2-methyl-3-((3-methyl-4-(tetrahydro-2H-pyran-4-carbonyl)piperazin-1-yl)methyl)phenyl)-5-cyano-6-methylnicotinamide, trifluoroacetic acid salt E80: (S)—N-(5-chloro-2-methyl-3-((3-methyl-4-(tetrahydro-2H-pyran-4-carbonyl)piperazin-1-yl)methyl)phenyl)-3-cyano-4-methylbenzamide, trifluoroacetic acid salt E81: N-(5-chloro-2-methyl-3-(((S)-3-methyl-4-((R)-tetrahydrofuran-2-carbonyl)piperazin-1-yl)methyl)phenyl)-6-(fluoromethyl)nicotinamide E82: N-(5-chloro-2-methyl-3-(((S)-3-methyl-4-((S)-tetrahydrofuran-2-carbonyl)piperazin-1-yl)methyl)phenyl)-6-(fluoromethyl)nicotinamide E83: (S)—N-(5-chloro-2-methyl-3-((3-methyl-4-(tetrahydro-2H-pyran-4-carbonyl)piperazin-1-yl)methyl)phenyl)-6-methoxynicotinamide E84: (S)—N-(5-chloro-2-methyl-3-((3-methyl-4-(tetrahydro-2H-pyran-4-carbonyl)piperazin-1-yl)methyl)phenyl)-5-fluoro-6-methylnicotinamide E85: 5-chloro-N-(5-fluoro-2-methyl-3-(((S)-3-methyl-4-((R)-tetrahydrofuran-2-carbonyl)piperazin-1-yl)methyl)phenyl)-6-methylnicotinamide E86: 5-chloro-N-(5-fluoro-2-methyl-3-(((S)-3-methyl-4-((S)-tetrahydrofuran-2-carbonyl)piperazin-1-yl)methyl)phenyl)-6-methylnicotinamide E87: N-(5-chloro-3-(((S)-3-ethyl-4-((R)-tetrahydrofuran-2-carbonyl)piperazin-1-yl)methyl)-2-methylphenyl)-6-methylnicotinamide

| | Structure | Characterization |
|---|---|---|
| E78 | 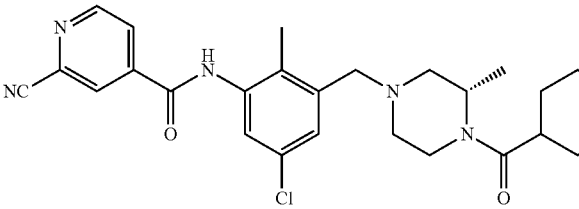 | $^1$H NMR (400 MHz, MeOD-d$_4$): 8.91 (d, J = 4.9 Hz, 1H), 8.36 (s, 1H), 8.14 (d, J = 3.9 Hz, 1H), 7.39 (d, J = 1.5 Hz, 1H), 7.32 (d, J = 1.5 Hz, 1H), 4.72-4.55 (m, 1H), 4.36-4.22 (m, 1H), 4.00-3.90 (m, 2H), 3.84 (d, J = 13.0 Hz, 0.5H), 3.57-3.44 (m, 4.5H), 3.44-3.34 (m, 0.5H), 3.03-2.81 (m, 2.5H), 2.80-2.67 (m, 1H), 2.31 (s, 3H), 2.27-1.96 (m, 2H), 1.94-1.51 (m, 4H), 1.42-1.17 (m, 3H). MS (ESI): C$_{26}$H$_{30}$ClN$_5$O$_3$ requires 495; found 496 [M + H]$^+$. |
| E79 | 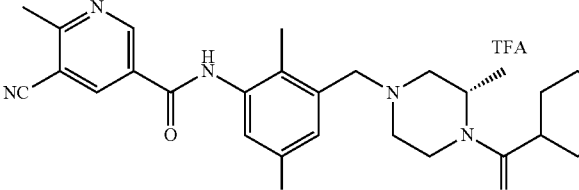 | $^1$H NMR (400 MHz, MeOD-d$_4$): 9.22 (s, 1H), 8.65 (s, 1H), 7.66-7.50 (m, 2H), 4.58-4.44 (m, 2H), 4.24 (d, J = 13.7 Hz, 1H), 4.02-3.88 (m, 2H), 3.64-3.45 (m, 6H), 3.18-1.90 (m, 3H), 2.85 (s, 3H), 2.36 (s, 3H), 1.91-1.52 (m, 4H), 1.52-1.22 (m, 3H). MS (ESI): C$_{27}$H$_{32}$ClN$_5$O$_3$ requires 509; found 510 [M + H]$^+$. |
| E80 | 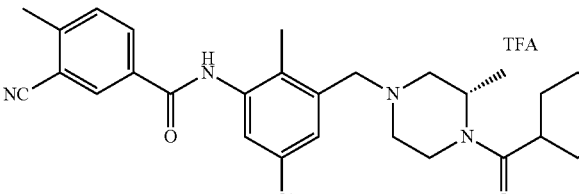 | $^1$H NMR (400 MHz, MeOD-d$_4$): 8.30 (s, 1H), 8.17 (d, J = 7.1 Hz, 1H), 7.63 (d, J = 8.3 Hz, 1H), 7.57 (s, 1H), 7.53 (s, 1H), 4.70-4.51 (m, 1H), 4.43-4.24 (m, 2H), 4.21-4.10 (m, 1H), 4.04-3.92 (m, 2H), 3.64-3.46 (m, 3H), 3.43-3.38 (m, 2H), 3.22-2.88 (m, 3H), 2.65 (s, 3H), 2.35 (s, 3H), 1.92-1.55 (m, 4H), 1.51-1.22 (m, 3H). $^{19}$F NMR (376 MHz, MeOD-d$_4$): −77.2. MS (ESI): C$_{28}$H$_{33}$ClN$_4$O$_3$ requires 508; found 509 [M + H]$^+$. |
| E81 | 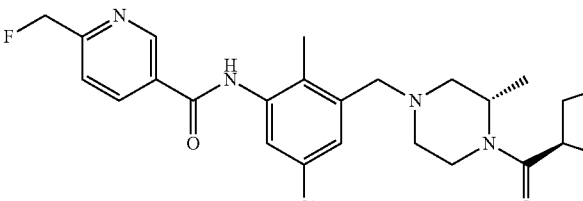 | $^1$H NMR (400 MHz, MeOD-d$_4$): 9.11 (s, 1H), 8.43 (dd, J = 8.0 Hz, 1.8 Hz, 1H), 7.70 (d, J = 8.3 Hz, 1H), 7.38 (s, 1H), 7.34-7.28 (m, 1H), 5.56 (d, J = 46.7 Hz, 2H), 4.75-4.68 (m, 1H), 4.67-4.58 (m, 0.5H), 4.28 (d, J = 12.5 Hz, 0.5H), 4.22-4.14 (m, 0.5H), 3.99-3.90 (m, 1H), 3.89-3.78 (m, 1.5H), 3.58-3.45 (m, 2H), 3.40-3.32 (m, 0.5H), 3.06-2.97 (m, 0.5H), 2.90-2.79 (m, 1H), 2.74 (d, J = 10.8 Hz, 1H), 2.32 (s, 3H), 2.29-1.86 (m, 6H), 1.40-1.21 (m, 3H). MS (ESI): C$_{25}$H$_{30}$ClFN$_4$O$_3$ requires 488; found 489 [M + H]$^+$. |
| E82 | 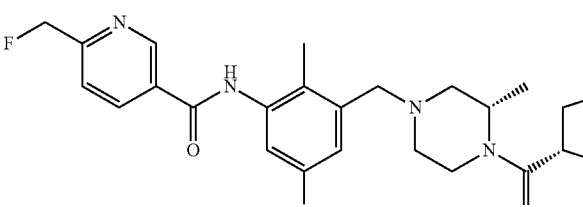 | $^1$H NMR (400 MHz, MeOD-d$_4$): 9.11 (s, 1H), 8.43 (dd, J = 8.2 Hz, 1.9 Hz, 1H), 7.70 (d, J = 8.0 Hz, 1H), 7.38 (d, J = 2.0 Hz, 1H), 7.31 (d, J = 2.0 Hz, 1H), 5.56 (d, J = 46.7 Hz, 2H), 4.75-4.59 (m, 1.5H), 4.39-4.24 (m, 1H), 3.98-3.88 (m, 1H), 3.88-3.80 (m, 1H), 3.77 (d, J = 14.1 Hz, 0.5H), 3.57-3.46 (m, 2H), 3.45-3.35 (m, 0.5H), 3.07-2.95 (m, 0.5H), 2.89-2.79 (m, 1H), 2.73 (d, J = 11.0 Hz, 1H), 2.32 (s, 3H), 2.29-1.89 (m, 6H), 1.41-1.20 (m, 3H). MS (ESI): C$_{25}$H$_{30}$ClFN$_4$O$_3$ requires 488; found 489 [M + H]$^+$. |
| E83 | 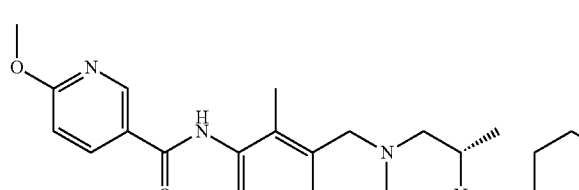 | $^1$H NMR (400 MHz, MeOD-d$_4$): 8.79 (brs, 1H), 8.21 (dd, J = 8.6 Hz, 1.7 Hz, 1H), 7.33 (s, 1H), 7.29 (s, 1H), 6.91 (d, J = 8.8 Hz, 1H), 4.72-4.56 (m, 1H), 4.37-4.18 (m, 1H), 4.00 (s, 3H), 3.98-3.88 (m, 2H), 3.83 (d, J = 13.4 Hz, 0.5H), 3.60-3.45 (m, 4.5H), 3.43-3.34 (m, 0.5H), 3.04-2.71 (m, 2.5H), 2.70-2.68 (m, 1H), 2.30 (s, 3H), 2.26-1.94 (m, 2H), 1.93-1.49 (m, 4H), 1.44-1.14 (m, 3H). MS (ESI): C$_{26}$H$_{33}$ClN$_4$O$_4$ requires 500; found 501 [M + H]$^+$. |
| E84 | 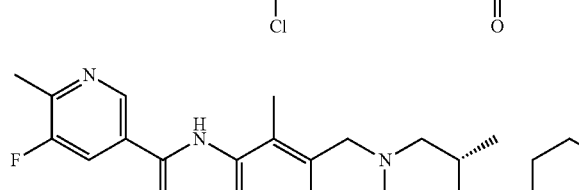 | $^1$H NMR (400 MHz, MeOD-d$_4$): 8.87 (s, 1H), 8.06 (d, J = 10.0 Hz, 1H), 7.35 (s, 1H), 7.31 (s, 1H), 4.66 (brs, 0.5H), 4.33-4.29 (m, 1H), 3.96-3.94 (m, 2H), 3.86-3.82 (m, 0.5H), 3.52-3.36 (m, 4.5H), 2.30-2.84 (m, 2.5H), 2.77-2.71 (m, 1H), 3.29 (d, J = 2.8 Hz, 3H), 2.30 (s, 3H), 2.25-1.97 (m, 2H), 1.91-1.54 (m, 4H), 1.38-1.22 (m, 3H). MS (ESI): C$_{26}$H$_{32}$ClFN$_4$O$_3$ requires 502; found 503 [M + H]$^+$. |

| | Structure | Characterization |
|---|---|---|
| E85 | 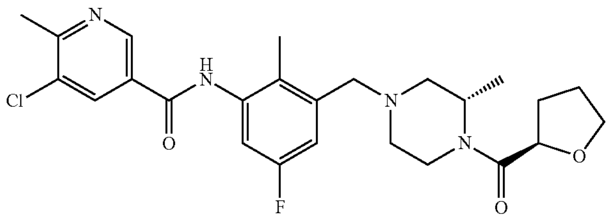 [SMILES: Cc1ncc(C(=O)Nc2cc(F)cc(CN3CCN(C(=O)[C@H]4CCCO4)[C@@H](C)C3)c2C)cc1Cl] | $^1$H NMR (400 MHz, MeOD-$d_4$): 8.94 (s, 1H), 8.36 (s, 1H), 7.16-7.06 (m, 2H), 4.75-4.67 (m, 1H), 4.67-4.58 (m, 0.5H), 4.28 (d, J = 13.3 Hz, 0.5H), 4.22-4.13 (m, 0.5H), 4.00-3.90 (m, 1H), 3.89-3.77 (m, 1.5H), 3.57-3.46 (m, 2H), 3.40-3.32 (m, 0.5H), 3.07-2.96 (m, 0.5H), 2.90-2.80 (m, 1H), 2.79-2.67 (m, 4H), 2.29 (s, 3H), 2.26-1.86 (m, 6H), 1.42-1.21 (m, 3H). MS (ESI): $C_{25}H_{30}ClFN_4O_3$ requires 488; found 489 [M + H]$^+$. |
| E86 | 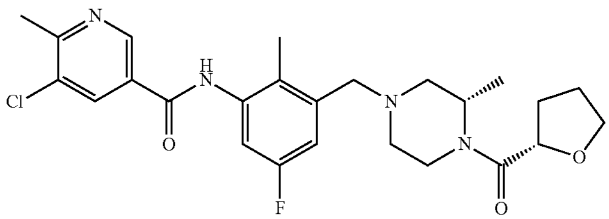 [SMILES: Cc1ncc(C(=O)Nc2cc(F)cc(CN3CCN(C(=O)[C@@H]4CCCO4)[C@@H](C)C3)c2C)cc1Cl] | $^1$H NMR (400 MHz, MeOD-$d_4$): 8.93 (s, 1H), 8.35 (s, 1H), 7.16-7.05 (m, 2H), 4.75-4.58 (m, 1.5H), 4.40-4.25 (m, 1H), 3.98-3.88 (m, 1H), 3.88-3.80 (m, 1H), 3.77 (d, J = 12.8 Hz, 0.5H), 3.57-3.46 (m, 2H), 3.46-3.35 (m, 0.5H), 3.07-2.94 (m, 0.5H), 2.85 (d, J = 10.3 Hz, 1H), 2.77-2.67 (m, 4H), 2.29 (s, 3H), 2.26-1.87 (m, 6H), 1.44-1.21 (m, 3H); MS (ESI): $C_{25}H_{30}ClFN_4O_3$ requires 488; found 489; [M + H]$^+$. |
| E87 | 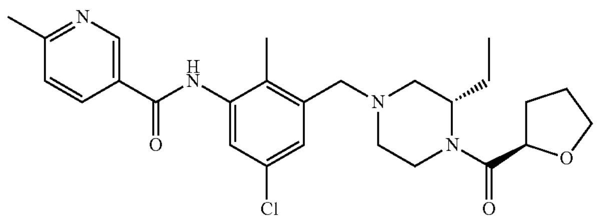 [SMILES: CC[C@H]1CN(Cc2cc(Cl)cc(NC(=O)c3ccc(C)nc3)c2C)CCN1C(=O)[C@H]1CCCO1] | $^1$H NMR (400 MHz, MeOD-$d_4$): 9.02 (s, 1H), 8.29 (dd, J = 8.0 Hz, 2.4 Hz, 1H), 7.49 (d, J = 8.0 Hz, 1H), 7.37 (s, 1H), 7.32 (d, J = 1.6 Hz, 1H), 4.77-4.75 (m, 1H), 4.45-4.32 (m, 1H), 4.02-3.95 (m, 1H), 3.90-3.82 (m, 2H), 3.56-3.47 (m, 2H), 3.28-3.27 (m, 0.5H), 2.99-2.92 (m, 0.5H), 2.89-2.84 (m, 2H), 2.65 (s, 3H), 2.31 (d, J = 1.6 Hz, 3H), 2.28-1.70 (m, 8H), 0.89-0.80 (m, 3H). MS (ESI): $C_{26}H_{33}ClN_4O_3$ requires 484; found 485 [M + H]$^+$. |

Example 88

5-chloro-N-(5-chloro-2-methyl-3-(((S)-3-methyl-4-((S)-tetrahydrofuran-2-carbonyl)piperazin-1-yl)methyl)phenyl)-6-methylnicotinamide (E88)

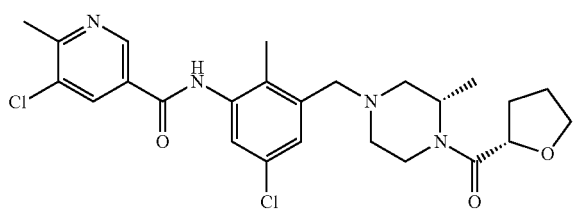 [SMILES: Cc1ncc(C(=O)Nc2cc(Cl)cc(CN3CCN(C(=O)[C@@H]4CCCO4)[C@@H](C)C3)c2C)cc1Cl]

To a solution of ((S)-4-(3-amino-5-chloro-2-methylbenzyl)-2-methylpiperazin-1-yl)((S)-tetrahydrofuran-2-yl)methanone (D74, 100 mg), 5-chloro-6-methylnicotinic acid (D5, 48.8 mg), HATU (162 mg) in DCM (15 mL) was added DIPEA (0.099 mL). The mixture was stirred at RT overnight. Cold water (30 mL) was added and the aqueous layer was extracted with DCM (2×30 mL). The combined organic layers were dried over $Na_2SO_4$, filtered and concentrated in vacuo. The residue was purified by column chromatography (eluting with PE:EA=50% to 100%) and preparative HPLC to give the title compound (26 mg) as a white solid. $^1$H NMR (400 MHz, MeOD-$d_4$): 8.94 (s, 1H), 8.36 (s, 1H), 7.36 (d, J=1.8 Hz, 1H), 7.31 (d, J=1.8 Hz, 1H), 4.74-4.59 (m, 1.5H), 4.37-4.25 (m, 1H), 3.97-3.88 (m, 1H), 3.88-3.80 (m, 1H), 3.80-3.73 (m, 0.5H), 3.55-3.46 (m, 2H), 3.45-3.35 (m, 0.5H), 3.06-2.95 (m, 0.5H), 2.88-2.80 (m, 1H), 2.76-2.72 (m, 1H), 2.70 (s, 3H), 2.31 (s, 3H), 2.27-1.68 (m, 6H), 1.41-1.22 (m, 3H). MS (ESI): $C_{25}H_{30}Cl_2N_4O_3$ requires 504; found 505 [M+H]$^+$.

Example 89

5-chloro-N-(5-chloro-2-methyl-3-(((S)-3-methyl-4-((R)-tetrahydrofuran-2-carbonyl)piperazin-1-yl)methyl)phenyl)-6-methylnicotinamide (E89)

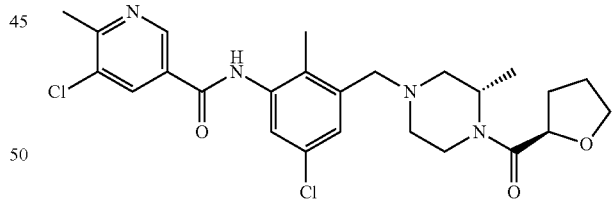

To a mixture of ((S)-4-(3-amino-5-chloro-2-methylbenzyl)-2-methylpiperazin-1-yl)((R)-tetrahydrofuran-2-yl)methanone (D75, 100 mg), 5-chloro-6-methylnicotinic acid (D5, 48.8 mg) and HATU (162 mg) in DCM (10 mL) was added DIPEA (0.099 mL). The mixture was stirred at RT overnight. Cold water (30 mL) was added and the aqueous layer was extracted with DCM (2×30 mL). The combined organic layers were dried over $Na_2SO_4$, filtered and concentrated in vacuo. The residue was purified by column chromatography (eluting with EA:PE=0% to 50%) and preparative HPLC to afford the title compound (10 mg) as a white solid. $^1$H NMR (400 MHz, MeOD-$d_4$): 8.94 (d, J=1.6 Hz, 1H), 8.36 (d, J=1.6 Hz, 1H), 7.36 (s, 1H), 7.32 (d, J=4.2 Hz, 1H), 4.90-4.69 (m, 1H), 4.64-4.62 (m, 0.5H), 4.33-4.20

(m, 1H), 3.97-3.94 (m, 1H), 3.88-3.81 (m, 1.5H), 3.53-4.99 (m, 2H), 3.34-3.33 (m, 0.5H), 3.04-2.99 (m, 0.5H), 2.88-2.81 (m, 1H), 2.75-2.71 (m, 4H), 2.31 (s, 3H), 2.26-1.92 (m, 6H), 1.38-1.25 (m, 3H). MS (ESI): $C_{25}H_{30}Cl_2N_4O_3$ requires 504; found 505 [M+H]$^+$.

Example 90

N-(5-chloro-2-methyl-3-(((S)-3-methyl-4-((S)-tetrahydrofuran-2-carbonyl)piperazin-1-yl)methyl)phenyl)-5,6-dimethylnicotinamide (E90)

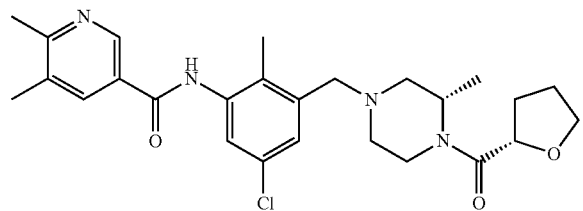 [SMILES: Cc1cc(C(=O)Nc2cc(Cl)cc(CN3CCN(C(=O)[C@@H]4CCCO4)[C@@H](C)C3)c2C)cnc1C]

The mixture of (S)—N-(5-chloro-2-methyl-3-((3-methylpiperazin-1-yl)methyl)phenyl)-5,6-dimethylnicotinamide, 2 hydrochloride acid salt (D89, 100 mg), (S)-tetrahydrofuran-2-carboxylic acid (30.0 mg), DIPEA (66.8 mg) and HATU (147 mg) in DCM (2 mL) was stirred for 2 hours. The mixture was concentrated and purified by preparative HPLC to get the titled compound (10 mg). $^1$H NMR (400 MHz, MeOD-d$_4$): 8.82 (s, 1H), 8.13 (s, 1H), 7.35 (d, J=2.3 Hz, 1H), 7.30 (d, J=2.0 Hz, 1H), 4.73-4.63 (m, 1.5H), 4.35-4.28 (m, 1H), 3.96-3.75 (m, 2.5H), 3.54-3.47 (m, 2H), 3.43-3.37 (m, 0.5H), 3.04-2.98 (m, 0.5H), 2.86-2.83 (m, 1H), 2.74-2.71 (m, 1H), 2.59 (s, 3H), 2.42 (s, 3H), 2.31 (s, 3H), 2.26-1.89 (m, 6H), 1.38-1.25 (m, 3H). MS (ESI): $C_{26}H_{33}ClN_4O_3$ requires 484; found 485 [M+H]$^+$.

Examples 91 & 92

N-(5-chloro-2-methyl-3-(((S)-3-methyl-4-((R)-tetrahydrofuran-3-carbonyl)piperazin-1-yl)methyl)phenyl)-5-cyano-6-methylnicotinamide and N-(5-chloro-2-methyl-3-(((S)-3-methyl-4-((S)-tetrahydrofuran-3-carbonyl)piperazin-1-yl)methyl)phenyl)-5-cyano-6-methylnicotinamide (E91 & E92)

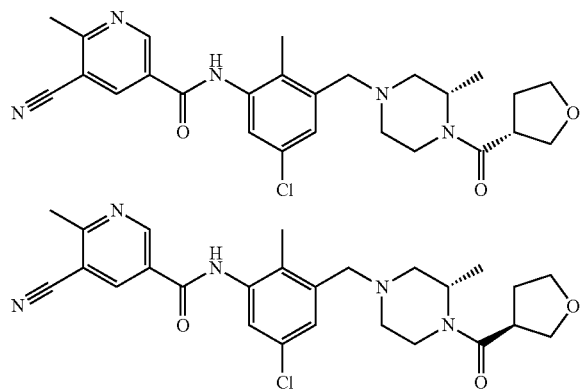

To the solution of (S)—N-(5-chloro-2-methyl-3-((3-methylpiperazin-1-yl)methyl)phenyl)-5-cyano-6-methylnicotinamide (D57, 238 mg) in DMF (3 mL) was added tetrahydrofuran-3-carboxylic acid (83 mg), HATU (273 mg) and TEA (182 mg), the resulting mixture was stirred at RT overnight. The mixture was partitioned between EA and water, the organic layer was washed with brine, dried over anhydrous Na$_2$SO$_4$. After concentration, the mixture was first purified by preparative HPLC and further purified by chiral HPLC to afford the title compounds (56 mg and 54 mg) as yellow solids. Isomer 1: $^1$H NMR (400 MHz, DMSO-d$_6$): 10.27 (s, 1H), 9.21 (d, J=1.8 Hz, 1H), 8.73 (d, J=1.8 Hz, 1H), 7.41 (d, J=1.8 Hz, 1H), 7.29 (s, 1H), 4.56 (brs, 0.5H), 4.22-4.19 (m, 1H), 3.96-3.59 (m, 5H), 3.50-3.44 (m, 2H), 3.30-3.26 (m, 0.5H), 3.22-3.16 (m, 0.5H), 2.84-2.73 (m, 4.5H), 2.66-2.63 (m, 1H), 2.23 (s, 3H), 2.16-1.86 (m, 4H), 1.26-1.11 (m, 3H). MS (ESI): $C_{26}H_{30}ClN_5O_3$ requires 495; found 496 [M+H]$^+$. Isomer 2: $^1$H NMR (400 MHz, DMSO-d$_6$): 10.28 (s, 1H), 9.21 (d, J=1.6 Hz, 1H), 8.73 (d, J=1.6 Hz, 1H), 7.41 (d, J=1.8 Hz, 1H), 7.29 (s, 1H), 4.55 (brs, 0.5H), 4.25-4.19 (m, 1H), 3.96-3.64 (m, 5H), 3.50-3.43 (m, 2H), 3.29-3.25 (m, 0.5H), 3.24-3.18 (m, 0.5H), 2.84-2.74 (m, 4.5H), 2.66-2.63 (m, 1H), 2.23 (s, 3H), 2.18-1.85 (m, 4H), 1.25-1.12 (m, 3H). MS (ESI): $C_{26}H_{30}ClN_5O_3$ requires 495; found 496 [M+H]$^+$.

Examples 93 & 94

N-(5-chloro-2-methyl-3-(((S)-3-methyl-4-((R)-tetrahydrofuran-3-carbonyl)piperazin-1-yl)methyl)phenyl)-5-methoxy-6-methylnicotinamide and N-(5-chloro-2-methyl-3-(((S)-3-methyl-4-((S)-tetrahydrofuran-3-carbonyl)piperazin-1-yl)methyl)phenyl)-5-methoxy-6-methylnicotinamide (E93 & E94)

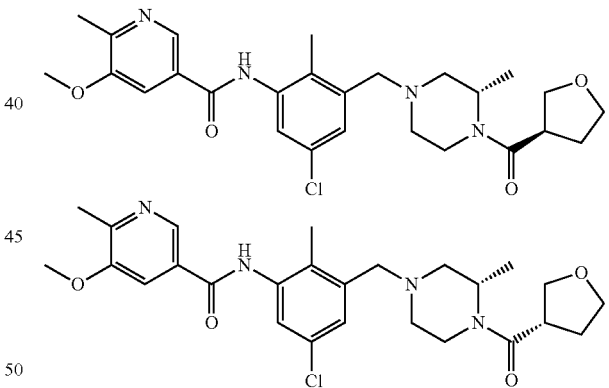

To the mixture of tetrahydrofuran-3-carboxylic acid (17.29 mg) in DCM (20 mL) were added (S)—N-(5-chloro-2-methyl-3-((3-methylpiperazin-1-yl)methyl)phenyl)-5-methoxy-6-methylnicotinamide, 2 hydrochloride acid salt (D90, 60 mg), HATU (67.9 mg), TEA (45.2 mg) and the reaction was stirred at RT overnight. The mixture was partitioned between EA and water, the organic layer was washed with brine, dried over anhydrous Na$_2$SO$_4$. After concentration, the mixture was first purified by preparative HPLC and further purified by chiral HPLC to afford the title compounds (5 mg and 17 mg) as yellow solids. Isomer 1: $^1$H NMR (400 MHz, CDCl$_3$) 8.51 (s, 1H), 7.87 (s, 1H), 7.79 (s, 1H), 7.66 (s, 1H), 7.14 (s, 1H), 4.77 (brs, 0.5H), 4.42-4.39 (m, 0.5H), 4.05-3.81 (m, 7H), 3.65-3.62 (m, 0.5H), 3.51-3.32 (m, 2.5H), 3.20 (brs, 1H), 2.99-2.93 (m, 0.5H), 2.83-2.78 (m, 1H), 2.70-2.67 (m, 1H), 2.54 (s, 3H), 2.31-2.14 (m, 4.5H), 2.05-2.03 (m, 2H), 1.35-1.23 (m, 4H). MS (ESI): $C_{26}H_{33}ClN_4O_4$ requires 500; found 501 [M+H]$^+$. Isomer 2: $^1$H NMR (400 MHz, CDCl$_3$) 8.52 (d, J=1.8 Hz, 1H), 7.86 (s, 1H), 7.82 (s, 1H), 7.67 (d, J=2.0 Hz, 1H), 7.15 (brs, 1H), 4.76 (brs, 0.5H), 4.43-4.40 (m, 0.5H), 4.12-3.84 (m, 7H), 3.62-3.58 (m, 0.5H), 3.51-3.35 (m, 2.5H), 3.24-3.15 (m, 1H), 2.98-2.94 (m, 0.5H), 2.83-2.79 (m, 1H), 2.70-2.67 (m, 1H), 2.54 (s, 3H), 2.31 (s, 3H), 2.24-1.98 (m, 3.5H), 1.37-1.23 (m, 4H). MS (ESI): $C_{26}H_{33}ClN_4O_4$ requires 500; found 501 [M+H]$^+$.

Example 95

N-(5-chloro-2-methyl-3-(((R)-3-methyl-4-((R)-tetrahydrofuran-2-carbonyl)piperazin-1-yl)methyl)phenyl)-5-fluoro-6-methylnicotinamide (E95)

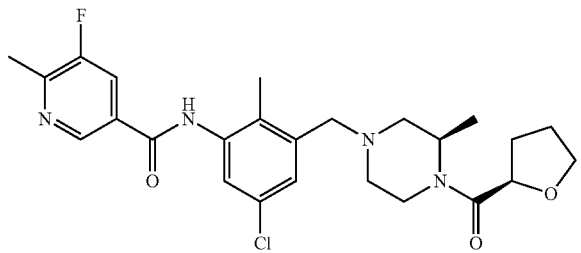 [SMILES: Cc1ncc(C(=O)Nc2cc(Cl)cc(CN3CCN(C(=O)[C@H]4CCCO4)[C@H](C)C3)c2C)cc1F]

The mixture of (R)—N-(5-chloro-2-methyl-3-((3-methylpiperazin-1-yl)methyl)phenyl)-5-fluoro-6-methylnicotinamide, 2 hydrochloride acid salt (D91, 100 mg), (R)-tetrahydrofuran-2-carboxylic acid (25.04 mg), HATU (123 mg) and DIPEA (0.188 mL) in DMF (5 mL) was stirred at RT for 2 hours. The mixture was diluted with water (50 mL) and extracted with EA (3×50 mL). The combined organic layers were washed with brine and dried over Na$_2$SO$_4$. After concentration, the residue was purified by preparative HPLC to afford the title compound (60 mg). $^1$H NMR (400 MHz, MeOD-d$_4$): 8.87 (s, 1H), 8.06 (dd, J=9.8, 1.8 Hz, 1H), 7.36 (d, J=2.3 Hz, 1H), 7.30 (d, J=2.3 Hz, 1H), 4.71-4.65 (m, 1.5H), 4.32-4.28 (m, 1H), 3.95-3.75 (m, 2.5H), 3.54-3.47 (m, 2H), 3.42-3.36 (m, 0.5H), 3.03-2.98 (m, 0.5H), 2.85-2.83 (m, 1H), 2.73-2.71 (m, 1H), 2.60 (d, J=3.0 Hz, 3H), 2.30-1.89 (m, 9H), 1.37-1.24 (m, 3H). MS (ESI): $C_{25}H_{30}ClFN_4O_3$ requires 488; found 489 [M+H]$^+$.

Example 96

N-(5-chloro-2-methyl-3-(((R)-3-methyl-4-((S)-tetrahydrofuran-2-carbonyl)piperazin-1-yl)methyl)phenyl)-5-fluoro-6-methylnicotinamide (E96)

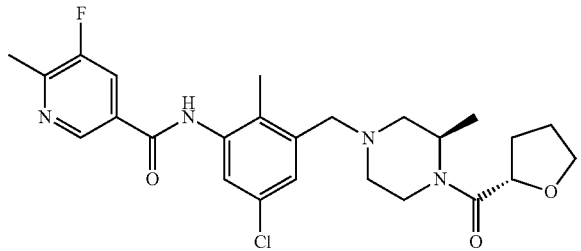 [SMILES: Cc1ncc(C(=O)Nc2cc(Cl)cc(CN3CCN(C(=O)[C@@H]4CCCO4)[C@H](C)C3)c2C)cc1F]

The mixture of (R)—N-(5-chloro-2-methyl-3-((3-methylpiperazin-1-yl)methyl)phenyl)-5-fluoro-6-methylnicotinamide, 2 hydrochloride acid salt (D91, 100 mg), (S)-tetrahydrofuran-2-carboxylic acid (25.04 mg), HATU (123 mg) and DIPEA (0.188 mL) in DMF (5 mL) was stirred at RT for 2 hours. The mixture was diluted with water (50 mL) and extracted with EA (3×50 mL). The combined organic layers were washed with brine and dried over Na$_2$SO$_4$. After concentration, the residue was purified by preparative HPLC to afford the title compound (60 mg). $^1$H NMR (400 MHz, MeOD-d$_4$): 8.87 (s, 1H), 8.06 (dd, J=9.6, 1.2 Hz, 1H), 7.36 (brs, 1H), 7.30 (brs, 1H), 4.72-4.62 (m, 1.5H), 4.29-4.26 (m, 0.5H), 4.18 (brs, 0.5H), 3.98-3.91 (m, 1H), 3.87-3.80 (m, 1.5H), 3.54-3.46 (m, 2H), 3.37-3.33 (m, 0.5H), 3.04-2.98 (m, 0.5H), 2.87-2.81 (m, 1H), 2.74-2.72 (m, 1H), 2.60 (d, J=3.2 Hz, 3H), 2.30-1.91 (m, 9H), 1.38-1.23 (m, 3H). MS (ESI): $C_{25}H_{30}ClFN_4O_3$ requires 488; found 489 [M+H]$^+$.

Example 97

N-(5-chloro-2-methyl-3-(((R)-3-methyl-4-((S)-tetrahydrofuran-3-carbonyl)piperazin-1-yl)methyl)phenyl)-5-fluoro-6-methylnicotinamide (E97)

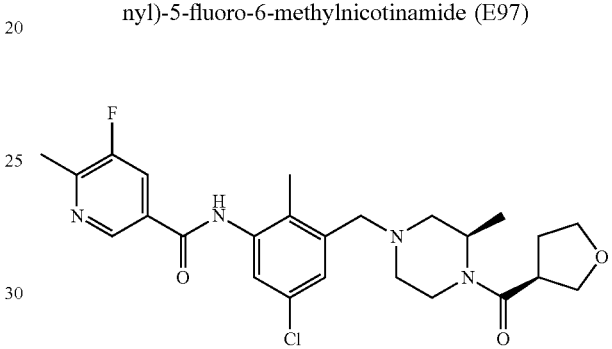

To a solution of (R)—N-(5-chloro-2-methyl-3-((3-methylpiperazin-1-yl)methyl)phenyl)-5-fluoro-6-methylnicotinamide, 2 Trifluoroacetic acid salt (D92, 415 mg) in DMF (4 mL), (S)-tetrahydrofuran-3-carboxylic acid (137.4 mg, 97% ee) solution in DMF (1 mL) was added, then HATU (741.3 mg) and DIPEA (0.55 ml) were added. The reaction mixture was stirred overnight. The mixture was purified by preparative HPLC and further purified by chiral SFC to afford the title compound (20 mg). $^1$H NMR (400 MHz, MeOD-d$_4$): 8.87 (s, 1H), 8.07 (dd, J=9.8, 1.7 Hz, 1H), 7.36 (d, J=2.2 Hz, 1H), 7.31 (d, J=2.0 Hz, 1H), 4.67 (brs, 0.5H), 4.32 (d, J=13.7 Hz, 0.5H), 4.24 (brs, 0.5H), 4.06-3.75 (m, 4.5H), 3.57-3.46 (m, 2H), 3.46-3.34 (m, 1.5H), 3.05-2.95 (m, 0.5H), 2.86 (d, J=11.2 Hz, 1H), 2.79-2.70 (m, 1H), 2.60 (d, J=2.9 Hz, 3H), 2.31 (s, 3H), 2.26-1.97 (m, 4H), 1.40-1.19 (m, 3H). $^{19}$F NMR (376 MHz, MeOD-d$_4$)-126.9. MS (ESI): $C_{25}H_{30}ClFN_4O_3$ requires 488; found 489 [M+H]$^+$.

Example 98

N-(5-chloro-2-methyl-3-(((R)-3-methyl-4-((R)-tetrahydrofuran-3-carbonyl)piperazin-1-yl)methyl)phenyl)-5-fluoro-6-methylnicotinamide (E98)

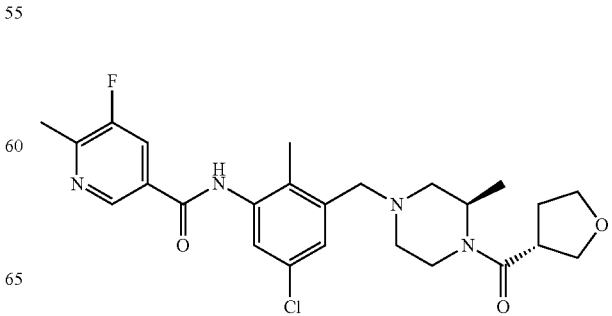

To a solution of (R)—N-(5-chloro-2-methyl-3-((3-methylpiperazin-1-yl)methyl)phenyl)-5-fluoro-6-methylnicotinamide, 2 Trifluoroacetic acid salt (D92, 415 mg) in DMF (4 mL), (R)-tetrahydrofuran-3-carboxylic acid (136.7 mg, 90% ee) solution in DMF (1 mL) was added, then HATU (741.3 mg) and DIPEA (0.55 ml) were added. The reaction mixture was stirred overnight. The mixture was purified by preparative HPLC and further purified by chiral SFC to afford the title compound (65 mg). $^1$H NMR (400 MHz, MeOD-d$_4$) 8.87 (s, 1H), 8.07 (dd, J=9.9, 1.6 Hz, 1H), 7.36 (d, J=2.2 Hz, 1H), 7.31 (d, J=1.7 Hz, 1H), 4.66 (brs, 0.5H), 4.37-4.24 (m, 1H), 3.99-3.72 (m, 4.5H), 3.58-3.46 (m, 2H), 3.45-3.35 (m, 1.5H), 3.05-2.95 (m, 0.5H), 2.86 (d, J=11.5 Hz, 1H), 2.79-2.70 (m, 1H), 2.60 (d, J=2.9 Hz, 3H), 2.31 (s, 3H), 2.28-1.96 (m, 4H), 1.38-1.20 (m, 3H). $^{19}$F NMR (376 MHz, MeOD-d$_4$)-125.4. MS (ESI): $C_{25}H_{30}ClFN_4O_3$ requires 488; found 489 [M+H]$^+$.

Example 99

5-((5-chloro-2-methyl-3-(((S)-3-methyl-4-((R)-tetrahydrofuran-3-carbonyl)piperazin-1-yl)methyl)phenyl)carbamoyl)-3-fluoro-2-methylpyridine 1-oxide (E99)

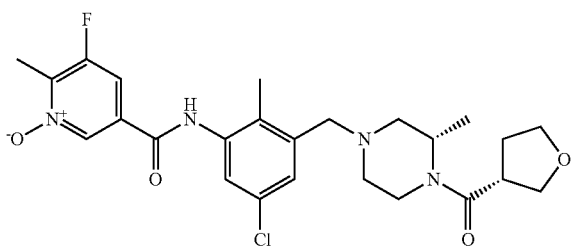

To a solution of (S)-5-((5-chloro-2-methyl-3-((3-methylpiperazin-1-yl)methyl)phenyl)carbamoyl)-3-fluoro-2-methylpyridine 1-oxide, 2 hydrochloride (D96, 280 mg) in DMF (10 mL) was added HATU (333 mg), DIPEA (0.612 mL) and (R)-tetrahydrofuran-3-carboxylic acid (102 mg) at 25° C., the reaction mixture was stirred at 25° C. overnight. The solvent was evaporated under reduced pressure and the residue was dissolved in dichloromethane. The organic layer was washed with water, brine and dried over sodium sulphate. The solvent was concentrated and the residue was purified by column chromatography on silica gel (petroleum ether/ethyl acetate=1/2) to give the title compound (140 mg) as a white solid. MS (ESI): $C_{25}H_{30}ClFN_4O_4$ requires 505; found 505 [M+H]$^+$.

Biological Data

As stated above, the compounds according to Formula I are RORγ modulators, and are useful in the treatment of diseases mediated by RORγ. The biological activities of the compounds according to Formula I can be determined using any suitable assay for determining the activity of a candidate compound as a RORγ modulator, as well as tissue and in vivo models.

Fluorescence Energy Transfer (FRET) Assay

The assays were performed in an assay buffer consisting of 50 mM NaF, 50 mM 3-(N-morpholino)propanesulfonic acid, pH 7.5, 50 μM 3-[(3-cholamidopropyl)dimethylammonio]-propanesulfonate, 0.1 mg/mL bovine serum albumin, and 10 mM dithiothreitol in 384-well plates (Greiner 784076, Longwood, Fla.). The total volume was 10 μL/well.

The europium-labeled SRC1 solution was prepared by adding an appropriate amount of biotinylated SRC and europium labeled streptavidin (PerkinElmer Life and Analytical Sciences, Waltham, Mass.) into assay buffer, with final concentrations of 27 and 3.3 nM, respectively. The allophycocyanin (APC)-labeled-LBD solution was prepared by adding an appropriate amount of biotinylated RORγ-LBD and APC-labeled streptavidin (CR130-100; PerkinElmer Life and Analytical Sciences) at a final concentration of 33 nM each. After 15 min of incubation at room temperature, a 20-fold excess of biotin was added to block the remaining free streptavidin. Equal volumes of europium-labeled SRC- and APC-labeled RORγ-LBD were then mixed with 0.2 μM surrogate agonist N-(2-chloro-6-fluorobenzyl)-N-((2'-methoxy-[1,1'-biphenyl]-4-yl)methyl)benzenesulfonamide (Zhang, W., et al., Mol. Pharmacol. 2012, 82, 583-590) and dispensed into 384-well assay plates at 10 μL volume/well. The 384-well assay plates had 100 nL of test compound in DMSO predispensed into each well. The plates were incubated for 1 h at room temperature and then read on ViewLux (PerkinElmer Life and Analytical Sciences) in LANCE mode configured for europeum-APC labels. Data were collected and analyzed by Activitybase.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL motifs in the co-activator SRC1(2) sequences. Short peptide sequences containing the LXXLL motif mimic the behavior of full-length co-activator.

The assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, thus it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in E. coli strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) was fused in frame to residues 263-518 of the human RORγ sequence.

Protein Purification

Approximately 50 g E. coli cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (Invitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mls. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (>8000×)] against PBS [100 mM NaPhosphate, pH 8 and 150 mM NaCl]. The concentration of RORγ-LBD was approximately 30 uM in PBS. Five-fold molar excess of NHS-LC-Biotin (Pierce) was added in a minimal volume of PBS. This solution was incubated with occasional gentle mixing for 60 minutes at ambient RT. The modified RORγ-LBD was dialyzed against 2 buffer changes—TBS pH 8.0 containing 5 mM DTT, 2 mM EDTA and 2% sucrose—each at least 20 times of the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five. A biotinylated peptide corresponding to amino acid 676 to 700 (CPSSHSSLTERH-KILHRLLQEGSPS) of the co-activator steroid receptor coactivator SRC1(2) was generated using similar method.

Assay

Preparation of Europium labeled SRC1(2) peptide: biotinylated SRC1(2) solution was prepared by adding an appropriate amount of biotinylated SRC1(2) from the 100 uM stock solution to a buffer containing 10 mM of freshly added DTT from solid to give a final concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Preparation of APC labeled RORγ-LBD: biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 ul of the reaction mixtures per well was added to the 384-well assay plates containing 1 ul of test compound per well in 100% DMSO. The plates were incubated for 1 hr and then read on ViewLux in Lance mode for EU/APC.

Jurkat Cell Luciferase Assay

RORγ is known to bind to a CNS (conserved non-coding sequences) enhancer element in the IL17 promoter. In this assay, RORγ activity is indirectly assessed using a luciferase reporter construct which contains the human IL17 promoter having the RORγ-specific CNS enhancer element. Inhibition of RORγ activity by a compound will result in a decrease in luciferase activity of Jurkat cells transfected with the reporter construct.

Materials

Jurkat Cell Line

For the luciferase reporter plasmid, the 3 Kb human IL17 promoter containing the RORγ-specific CNS enhancer element was PCR amplified from human genomic DNA and cloned into a pGL4-Luc2/hygro reporter plasmid sequentially as XhoI-HindIII (1.1 Kb) and KpnI-XhoI (1.9 Kb) fragments. For the 1.1 Kb fragment, PCR was used to amplify human IL17 proximal promoter region from genomic DNA of 293T cells using primers as follows: forward primer, 5'-CTCGAGTAGAGCAGGACAGGGAGGAA-3' (XhoI site is underlined) and reverse primer, 5'-AAGCTTGGATGGATGAGTTTGTGCCT-3' (HindIII site is underlined). The 1.1 kb DNA bands were excised, purified, and inserted into pMD19-T Simple Vector (Takara). After DNA sequencing confirmation, the 1.1 kb DNA was digested with XhoI and HindIII and inserted into XhoI/HindIII sites of pGL4.31 [luc2P/GAL4UAS/Hygro] (Promega) to generate the pIL17-1 kb-luc reporter construct. For the 1.9 Kb fragment, PCR was used to amplify human IL17 promoter region from genomic DNA using primers as follows: forward primer, 5'-GGTACCTGCCCTGCTCTATCCTGAGT-3' (KpnI site is underlined) and reverse primer, 5'-CTCGAGTGGTGAGTGCTGAGAGATGG-3' (XhoI site is underlined). The resulting 1.9 kb DNA bands were excised, gel purified, and cloned into a pMD19-T Simple Vector (Takara). DNA sequencing analysis revealed that there were three point mutations but none of which affected RORγ binding. The 1.9 kb DNA fragment was released by double digestion with KpnI and XhoI and inserted into pIL17-1 kb-luc to generate the luciferase reporter plasmid "pIL17-3 kb-CNS-luc." To overexpress RORγt, the full-length cDNA of human RORγt identical to the published sequence NM_001001523 was cloned into pcDNA3.1 at the KpnI-NotI cloning sites to generate the RORγt overexpression plasmid "CDNA3.1DhRORγ49-8".

The luciferase reporter plasmid and the RORγt overexpression plasmid were transfected into Jurkat cell line and a stable clone was identified. The stable clone was grown in 10% dialyzed FBS in RPMI (1640) with 800 ug/ml geneticin and 400 ug/ml hygromecin.

Assay

Compounds were dissolved in DMSO at three concentrations, 10 mM, 400 uM and 16 uM, and were dispensed into 384-wells assay plate at 40 nl, 12.5 nl, 5 nl respectively. The volume was adjusted with pure DMSO to a give a final uniform volume of 40 nl Jurkat cells described above were counted and centrifuged. The growth medium was discarded and the cells were resuspended with assay medium (phenol red free RPMI) at 1E-6/ml. Cells were added to each of the compounds in the assay plates. Cells were either untreated or treated with CD3 microbeads (Miltenyi Biotec) at 1 ul beads per 500,000 cells. Cells were culture overnight and luciferase assay (Promega) was performed. Data were collected by ViewLux (using luciferase greiner 384 setting).

Th17 Cell Differentiation Assay

ELISA

Mouse CD4+ cells were purified using the CD4+ T Cell Isolation II Kit according to manufacturer's instructions (Miltenyi Biotec). 96 well plates were pre-coated with anti-mCD3 antibody. Un-coated wells were used as controls. CD4+ Cells were resuspended in RPMI 1640 complete medium and were added to the 96-well plates. Cytokine cocktail and the compound were then added to the wells. Antibodies and cytokines (all from R&D Systems) used in the assay were selected from the following: anti-mCD3; anti-mCD28; anti-mIFNγ; anti-mIL4; mIL-6; mIL-23; mIL-1β; hTGF-β1. The culture was incubated at 37° C. for 3 days and supernatants were collected for ELISA. The IL-17 ELISAs were performed according to manufacturer's instructions (R&D Systems). The results were analyzed using Prism software with non-linear regression to determine $pIC_{50}$.

Intracellular Staining

The Th17 differentiation culture described above was maintained for 5 days and cells were analyzed by IL-17 and IFN-γ intracellular staining according to manufacturer's instructions (BD Biosciences).

Assay Data

The data described below represents a mean $pIC_{50}$ value of multiple test results if the test was performed more than once. It is understood that the data illustrated below may have reasonable variation depending on the specific conditions and procedures used by the person conducting the testing.

All exemplified compounds except Examples 97-99 were tested in the FRET assay described above. All tested compounds were found to have a $pIC_{50}$ between 5 and 8. For example, the compounds of Examples 57 and 91 demonstrated $pIC_{50}$ values of approximately 6.9 and 6.6 respectively.

All exemplified compounds except Examples 14, 18, 45, 46, 53, 66, 74, 75, 81, 82, 93, 97, and 98 were tested in the dual FRET assay described above. All tested compounds were found to have a $pIC_{50}$ between 5 and 8. For example, the compounds of Examples 57 and 91 demonstrated $pIC_{50}$ values of approximately 6.7 and 6.1 respectively.

All exemplified compounds except Examples 2-6, 10, 15, 16, 20, 21, 28, 29, 34, 35, 38, 39, 44-55, 63, 64, 68-72, 75-79, 81-84, 87, 89, and 95-99 were tested in the Jurkat cell luciferase assay described above. All tested compounds were found to have a $pIC_{50}$ between 5 and 9. For example, the compounds of Examples 57 and 91 demonstrated $pIC_{50}$ values of approximately 7.6 and 7.9 respectively.

All exemplified compounds except Examples 20, 21, 38, 39, 48-51, 54, 55, 61-64, 66, 67, 77, 79, 81, 82, and 95-99 were tested in the Th17 cell differentiation assay described above. All tested compounds were found to have a $pIC_{50}$ between 6 and 9. For example, the compounds of Examples 57 and 91 demonstrated $pIC_{50}$ values of approximately 7.09 and 7.76 respectively.

EAE Studies

Experimental Autoimmune Encephalomyelitis (EAE) is an animal model of multiple sclerosis. The ability of a test compound to ameliorate EAE can be measured in the EAE studies. Wild-type mice of the C57BL/6 (B6) strain are maintained under pathogen-free conditions. EAE is induced by intravenous injections of 100 ng of pertussis toxin (List Biological Laboratories) and subcutaneous immunization with an emulsion composed of $MOG_{35-55}$ peptide (300 μg/mouse) in PBS and an equal volume of complete Freund's adjuvant containing 5 mg/ml heat-killed *Mycobacterium tuberculosis* H37Ra (Difco Laboratories) on day 0, followed by another intravenous injections of 100 ng of pertussis toxin on day 2 as described previously (Wang et al. (2006) *J. Clin. Invest.* 116: 2434-2441). For treatment of EAE, each compound or vehicle PBS is given orally from day 0 at various doses selected from 3, 10, 30 and 100 mg/kg twice a day. Mice are scored for disease severity daily using a EAE scoring system (Wang et al. (2006) *J. Clin. Invest.* 116: 2434-2441): 0, no overt signs of disease; 1, limp tail or hind limb weakness but not both; 2, limptail and paraparesis (weakness, incomplete paralysis of one or two hind limbs); 3, paraplegia (complete paralysis of two hind limbs); 4, paraplegia with forelimb weakness or paralysis; and 5, moribund state or death. Clinical score data can be expressed as means±S.E.M.

In Vitro Percutaneous Studies

The in vitro percutaneous study is aimed to predict the level of percutaneous penetration obtained for a compound in a topical formulation for psoriasis. This assay coupled with the intrinsic potency of the compound are used to predict the likelihood of success of a compound to engage the target. The higher the ratio of the percutaneous penetration to the intrinsic potency, the higher the ratio of local skin concentration to the intrinsic potency and therefore the higher the chance of a compound to engage the target in a topical formulation.

The compounds can be manufactured in a modified aqueous cream at pH=6.

Aqueous Cream Composition

| Ingredients | % w/w |
| --- | --- |
| Cetostearyl alcohol | 7.2 |
| Cetomacrogol 1000 | 1.8 |
| White soft paraffin | 15.0 |
| Liquid paraffin | 6.0 |
| Water | 57.0 |
| Na2HPO4 | 0.6 |
| Citric Acid | 0.2 |
| Propylene Glycol | 10.0 |
| Methyl paraben | 0.1 |
| Caffeine | 0.1 |
| API#1 | 1.0 |
| API#2 | 1.0 |
| API#3 | 1.0 |

The study can be conducted with dermatomed abdominal human skin sourced from three skin donors using 2 cm2 Franz diffusion cells. The receiving fluid consisted of Bovine serum albumin (4% w/v) in 0.1% w/v sodium azide in Phospate Buffer Saline and can be heated at 37° C. in order to obtain 32° C. at the skin surface. The cream formulation can be applied on the donor side at a 10 mg dose, i.e. 5 mg/cm$^2$. The samples can be taken at the following time points: t=0, 3, 6, 9 and 24 h. The receiver samples can then be assayed using a method based upon protein precipitation with acetonitrile followed by LC/MS/MS analysis. The percutaneous flux (in ng/cm$^2$/hr) can be determined using the individual API (in a multiple composition) that has permeated into the receiver compartment over 24 hrs per cm$^2$.

Imiquimod-Induced Skin Inflammation

Imiquimod is an immune modifying agent that potently activates specific Toll-like receptors (e.g., TLR7) and induces irritation/inflammation of the skin that requires the IL23R/RORγ/IL17 axis of the immune system (van der Fits et al, (2009) *J Immunol*; 182:5836-5845; Gray et al, (2013) *Nature Immunol*; June; 14(6):584-92). The imiquimod-induced skin inflammation model can be used to assess the ability of an RORγ inhibitor to reduce Th17-driven inflammation in mice. For the ear-only skin inflammation model in which ear thickness is measured with digital engineer's calipers (Mitutoyo PK-0505), female wild type C57BL/6NTac mice can be obtained from Taconic (Hudson, N.Y.) at 8 to 12 wk of age and given a daily topical dose of 10 mg of commercially available imiquimod cream (5%) (Aldara; Medicis) distributed over both ears at approximately 11:00 h for up to 4 consecutive days. Alternatively, 72 mg of Aldara is distributed over both ears and the shaved/depiliated back skin of mice at approximately 11:00 h for 3 consecutive days to examine RORγ-dependent gene expression (RNA isolated from both ears using Qiazol followed by clean-up on with the RNeasy protocol (Qiagen, Germantown, Md.); Taqman probe/primer sets for B2M (Mm00437762_m1), IL-17A (Mm00439619_m1), IL-17F (Mm00521423_m1), or IL-22 (Mm00444241_m1) (Thermo Fisher Scientific, Inc., Waltham, Mass.) and ex vivo stimulated (anti-CD3 (2 ug/ml, clone eBio500A2, eBioscience, San Diego, Calif.), anti-CD28 (1 ug/ml, clone 37.51, BD Bioscience, San Jose, Calif.), recombinant mouse IL-13 (20 ng/ml, R&D Systems, Minneapolis, Minn.), and recombinant mouse IL-23 (20 ng/ml, R&D Systems, Minneapolis, Minn.) IL-17A protein expression from whole blood (Meso Scale Discovery, Rockville, Md.). For treatment of the skin inflammation in these models, each compound or vehicle (methylcellulose in water, 1% w/v, Sigma Aldrich, St. Louis, Mo.) is administered via oral gavage at approximately 08:00 h and 16:00 h daily at various doses selected from 1, 3, 10, and 30 mg/kg.

Human Peripheral Blood CD4+ T Cell Cultures and Cytokine Analysis

Human biological samples are cryopreserved human CD4+ T cells which may be purchased from AllCells, LLC and/or Stemcell Technologies, Inc. The CD4+ T cells are differentiated to the Th17 subtype by culturing for 5 days in tissue culture plates coated with anti-CD3 antibody (2 μg/mL) in Iscove's modified Dulbecco's medium (IMDM) containing 10% HI-FBS, 55 μM 2-mercaptoethanol and soluble anti-CD28 (3 μg/mL) in the presence of a Th17 skewing cocktail, including IL-1β (10 ng/mL), IL-6 (30 ng/mL), TGFβ (0.5 ng/mL), IL-21 (10 ng/mL), IL-23 (10 ng/mL), anti-IFNγ (10 μg/mL) and anti-IL-4 (10 μg/mL). To examine compound effects on Th17 polarization, freshly thawed CD4+ cells in IMDM supplemented with all Th17 polarization cocktail constituents (above) are seeded at low cell density (20,000 cells/well) directly into anti-CD3 coated round bottom 96-well plates already containing serially diluted compounds. Cells are incubated undisturbed for 5 days at 37° C. Immediately following culture, supernatant is analyzed for secreted IL-17A and IL-22 protein by MSD electrochemiluminescent cytokine assays (Mesoscale Discovery) and ELISA (Quantikine assay, R&D Systems), respectively. Compound treatment(s) may be performed in triplicate.

Methods of Use

The compounds of Formula I are modulators of RORγ and can be useful in the treatment of diseases mediated by RORγ, particularly autoimmune or inflammatory diseases. Examples of the inflammatory or autoimmune diseases of the invention include multiple sclerosis, rheumatoid arthritis, psoriasis, ankylosing spondylitis, Crohn's disease, inflammatory bowel disease, Sjorgen's syndrome, optic neuritis, chronic obstructive pulmonary disease, asthma, type I diabetes, neuromyelitis optica, Myasthenia Gavis, uveitis, Guillain-Barre syndrome, psoriatic arthritis, Gaves' disease and allergy. Accordingly, in another aspect the invention is directed to methods of treating autoimmune and inflammatory diseases mediated by RORγ.

In a further aspect, the present invention also provides a compound of Formula (I), or a pharmaceutically acceptable salt thereof, for use in therapy.

In a further aspect, the present invention also provides a compound of Formula (I), or a pharmaceutically acceptable salt thereof, for use in the treatment of inflammatory and autoimmune diseases mediated by RORγ.

In a further aspect, the present invention provides a compound of Formula (I), or a pharmaceutically acceptable salt thereof, for use in the treatment of multiple sclerosis.

In a further aspect, the present invention provides a compound of Formula (I), or a pharmaceutically acceptable salt thereof, for use in the treatment of ankylosing spondylitis.

In a further aspect, the present invention is directed to a method of treatment of an inflammatory or autoimmune disease mediated by RORγ, which comprises administering to a human in need thereof, a therapeutically effective amount of a compound of Formula (I), or a pharmaceutically acceptable salt thereof.

In yet a further aspect, the present invention is directed to a method of treating multiple sclerosis, which comprises administering to a human in need thereof, a therapeutically effective amount of a compound of Formula (I), or a pharmaceutically acceptable salt thereof.

In yet a further aspect, the present invention is directed to a method of treating ankylosing spondylitis, which comprises administering to a human in need thereof, a therapeutically effective amount of a compound of Formula (I), or a pharmaceutically acceptable salt thereof.

In a further aspect, the present invention is directed to the use of a compound of Formula (I), or a pharmaceutically acceptable salt thereof, in the manufacture of a medicament for use in the treatment of an inflammatory or autoimmune disease mediated by RORγ.

In a yet further aspect, the present invention is directed to the use of a compound of Formula (I), or a pharmaceutically acceptable salt thereof, in the manufacture of a medicament for use in the treatment of multiple sclerosis.

In a yet further aspect, the present invention is directed to the use of a compound of Formula (I), or a pharmaceutically acceptable salt thereof, in the manufacture of a medicament for use in the treatment of ankylosing spondylitis.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the human lungs whether inhaled through the mouth or through the nasal passages.

Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the individual being treated, the medical history of the individual to be treated, the nature of concurrent therapy, the desired therapeutic effect, and like factors within the knowledge and expertise of the skilled artisan. It will be further understood by such skilled artisans that suitable dosing regimens may require adjustment given an individual's response to the dosing regimen or over time as individual needs change.

Typical daily dosages may vary depending upon the particular route of administration chosen. Typical daily dosages for oral administration range from 0.1 mg to 1000 mg. Typical daily dosages for topical administration range from about 0.001% to about 10% w/w (weight percent) and preferably from about 0.01% to about 1% w/w.

Additionally, the compounds of the invention may be administered as prodrugs. As used herein, a "prodrug" of a compound of the invention is a functional derivative of the compound which, upon administration to an individual, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to an individual. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the individual such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 0.1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the individual by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the individual from one organ, or portion of the body, to another organ, or portion of the body. Certain pharmaceutically-acceptable excipients may be chosen for their ability to enhance compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

The invention claimed is:

1. A compound of Formula I or a pharmaceutically acceptable salt thereof:

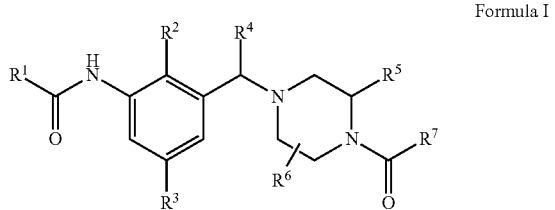

Formula I wherein
R$^1$ is:
5 to 6 membered monocyclic heteroaryl optionally substituted with i) C$_1$-C$_5$ alkyl optionally substituted with CF$_3$ or CN, ii) CH$_2$F; or iii) one to two substituents independently selected from the group consisting of halo, methyl, methoxy and CN; wherein said 5 to 6 membered monocyclic heteroaryl is selected from the group consisting of pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, and tetrazolyl, or N-oxides thereof; or
phenyl substituted with one to two substituents independently selected from the group consisting of CN, halo and methyl;
R$^2$ is C$_1$-C$_3$ alkyl;
R$^3$ is halo,
R$^4$ is H;
R$^5$ is C$_1$-C$_3$ alkyl,
R$^6$ is H or methyl; and
R$^7$ is tetrahydrofuranyl or tetrahydropyranyl, wherein said tetrahydrofuranyl or tetrahydropyranyl is optionally substituted with methyl.

2. The compound or salt according to claim 1, wherein R$^1$ is phenyl substituted with CN.

3. The compound or salt according to claim 1, wherein R$^1$ is phenyl substituted with CN and F.

4. The compound or salt according to any of claim 1, wherein R$^1$ is pyridinyl substituted with i) methyl and F; ii) methyl and Cl; iii) methyl and CN; or iv) CN and F.

5. The compound or salt according to any of claim 1, wherein R$^1$ is pyridinyl substituted with i) methyl and F.

6. The compound or salt according to claim 1, wherein R$^2$ is methyl.

7. The compound or salt according to claim 1, wherein R$^3$ is Cl.

8. The compound or salt according to claim 1, wherein R$^5$ is methyl.

9. The compound or salt according to claim 1, wherein R$^6$ is H.

10. The compound or salt according to claim 1, wherein R$^7$ is tetrahydrofuranyl.

11. The compound or salt according to claim 1, wherein R$^7$ is tetrahydropyranyl.

12. The compound according to claim 1 selected from the group consisting of:
(S)—N-(5-chloro-2-methyl-3-((3-methyl-4-(tetrahydro-2H-pyran-4-carbonyl)piperazin-1-yl)methyl)phenyl)-3-cyanobenzamide;
N-(5-chloro-2-methyl-3-(((S)-3-methyl-4-((R)-tetrahydrofuran-2-carbonyl)piperazin-1-yl)methyl)phenyl)-3-cyano-5-fluorobenzamide,
N-(5-chloro-2-methyl-3-(((S)-3-methyl-4-((S)-tetrahydrofuran-2-carbonyl)piperazin-1-yl)methyl)phenyl)-3-cyano-5-fluorobenzamide,
N-(5-chloro-2-methyl-3-(((S)-3-methyl-4-((R)-tetrahydrofuran-2-carbonyl)piperazin-1-yl)methyl)phenyl)-3-cyanobenzamide;
N-(5-chloro-2-methyl-3-(((S)-3-methyl-4-((R)-tetrahydrofuran-3-carbonyl)piperazin-1-yl)methyl)phenyl)-3-cyanobenzamide;
N-(5-chloro-2-methyl-3-(((S)-3-methyl-4-((S)-tetrahydrofuran-2-carbonyl)piperazin-1-yl)methyl)phenyl)-3-cyanobenzamide;
N-(5-chloro-2-methyl-3-(((S)-3-methyl-4-((S)-tetrahydrofuran-3-carbonyl)piperazin-1-yl)methyl)phenyl)-3-cyanobenzamide,
N-(5-chloro-2-methyl-3-(((S)-3-methyl-4-((R)-tetrahydrofuran-2-carbonyl)piperazin-1-yl)methyl)phenyl)-3-cyano-4-fluorobenzamide;
N-(5-chloro-2-methyl-3-(((S)-3-methyl-4-((S)-tetrahydrofuran-2-carbonyl)piperazin-1-yl)methyl)phenyl)-3-cyano-4-fluorobenzamide,
N-(5-chloro-2-methyl-3-(((S)-3-methyl-4-((R)-tetrahydrofuran-2-carbonyl)piperazin-1-yl)methyl)phenyl)-5-fluoro-6-methylnicotinamide;
N-(5-chloro-2-methyl-3-(((S)-3-methyl-4-((S)-tetrahydrofuran-2-carbonyl)piperazin-1-yl)methyl)phenyl)-5-fluoro-6-methylnicotinamide;

N-(5-chloro-2-methyl-3-(((S)-3-methyl-4-((R)-tetrahydrofuran-2-carbonyl)piperazin-1-yl)methyl)phenyl)-5-cyano-6-methylnicotinamide;

N-(5-chloro-2-methyl-3-(((S)-3-methyl-4-((S)-tetrahydrofuran-2-carbonyl)piperazin-1-yl)methyl)phenyl)-5-cyano-6-methylnicotinamide, N-(5-chloro-2-methyl-3-(((S)-3-methyl-4-((R)-tetrahydrofuran-3-carbonyl)piperazin-1-yl)methyl)phenyl)-5-fluoro-6-methylnicotinamide, N-(5-chloro-2-methyl-3-(((S)-3-methyl-4-((S)-tetrahydrofuran-3-carbonyl)piperazin-1-yl)methyl)phenyl)-5-fluoro-6-methylnicotinamide;

5-chloro-N-(5-chloro-2-methyl-3-(((S)-3-methyl-4-((S)-tetrahydrofuran-2-carbonyl)piperazin-1-yl)methyl)phenyl)-6-methylnicotinamide; and 5-chloro-N-(5-chloro-2-methyl-3-(((S)-3-methyl-4-((R)-tetrahydrofuran-2-carbonyl)piperazin-1-yl)methyl)phenyl)-6-methylnicotinamide or a pharmaceutically acceptable salt thereof.

13. The compound according to claim 1 selected from the group consisting of:

N-(5-chloro-2-methyl-3-(((S)-3-methyl-4-((S)-tetrahydrofuran-2-carbonyl)piperazin-1-yl)methyl)phenyl)-5,6-dimethylnicotinamide;

N-(5-chloro-2-methyl-3-(((S)-3-methyl-4-((R)-tetrahydrofuran-3-carbonyl)piperazin-1-yl)methyl)phenyl)-5-cyano-6-methylnicotinamide, N-(5-chloro-2-methyl-3-(((S)-3-methyl-4-((S)-tetrahydrofuran-3-carbonyl)piperazin-1-yl)methyl)phenyl)-5-cyano-6-methylnicotinamide;

N-(5-chloro-2-methyl-3-(((S)-3-methyl-4-((R)-tetrahydrofuran-3-carbonyl)piperazin-1-yl)methyl)phenyl)-5-methoxy-6-methylnicotinamide;

N-(5-chloro-2-methyl-3-(((S)-3-methyl-4-((S)-tetrahydrofuran-3-carbonyl)piperazin-1-yl)methyl)phenyl)-5-methoxy-6-methylnicotinamide, N-(5-chloro-2-methyl-3-(((R)-3-methyl-4-((R)-tetrahydrofuran-2-carbonyl)piperazin-1-yl)methyl)phenyl)-5-fluoro-6-methylnicotinamide;

N-(5-chloro-2-methyl-3-(((R)-3-methyl-4-((S)-tetrahydrofuran-2-carbonyl)piperazin-1-yl)methyl)phenyl)-5-fluoro-6-methylnicotinamide;

N-(5-chloro-2-methyl-3-(((R)-3-methyl-4-((S)-tetrahydrofuran-3-carbonyl)piperazin-1-yl)methyl)phenyl)-5-fluoro-6-methylnicotinamide, N-(5-chloro-2-methyl-3-(((R)-3-methyl-4-((R)-tetrahydrofuran-3-carbonyl)piperazin-1-yl)methyl)phenyl)-5-fluoro-6-methylnicotinamide; and 5-((5-chloro-2-methyl-3-(((S)-3-methyl-4-((R)-tetrahydrofuran-3-carbonyl)piperazin-1-yl)methyl)phenyl)carbamoyl)-3-fluoro-2-methylpyridine 1-oxide;

or a pharmaceutically acceptable salt thereof.

14. The compound according to claim 1 which is N-(5-chloro-2-methyl-3-(((S)-3-methyl-4-((S)-tetrahydrofuran-3-carbonyl)piperazin-1-yl)methyl)phenyl)-5-fluoro-6-methylnicotinamide, or a pharmaceutically acceptable salt thereof.

15. The compound according to claim 1 which is N-(5-chloro-2-methyl-3-(((S)-3-methyl-4-((R)-tetrahydrofuran-3-carbonyl)piperazin-1-yl)methyl)phenyl)-5-fluoro-6-methylnicotinamide, or a pharmaceutically acceptable salt thereof.

16. A pharmaceutical composition which comprises the compound of Formula I according to claim 1 or a pharmaceutically acceptable salt thereof and a pharmaceutically acceptable carrier or excipient.

17. A method of treating multiple sclerosis comprising administering to a human in need thereof an effective amount of the compound or pharmaceutically acceptable salt according to claim 1.

18. A method of treating ankylosing spondylitis comprising administering to a human in need thereof an effective amount of the compound or pharmaceutically acceptable salt according to claim 1.

19. The pharmaceutical composition according to claim 16, wherein the compound of Formula I is N-(5-chloro-2-methyl-3-(((S)-3-methyl-4-((S)-tetrahydrofuran-3-carbonyl)piperazin-1-yl)methyl)phenyl)-5-fluoro-6-methylnicotinamide or a pharmaceutically acceptable salt thereof.

20. The method of t eating multiple sclerosis according to claim 17, wherein the compound is N-(5-chloro-2-methyl-3-(((S)-3-methyl-4-((S)-tetrahydrofuran-3-carbonyl)piperazin-1-yl)methyl)phenyl)-5-fluoro-6-methylnicotinamide or a pharmaceutically acceptable salt thereof.

21. The method of treating ankylosing spondylitis according to claim 18, wherein the compound of is N-(5-chloro-2-methyl-3-(((S)-3-methyl-4-((S)-tetrahydrofuran-3-carbonyl)piperazin-1-yl)methyl)phenyl)-5-fluoro-6-methylnicotinamide or a pharmaceutically acceptable salt thereof.

* * * * *